(12) United States Patent
Gorczynski et al.

(10) Patent No.: US 7,368,535 B2
(45) Date of Patent: May 6, 2008

(54) CD200 RECEPTORS

(75) Inventors: Reginald M. Gorczynski, Willowdale (CA); Philip Marsden, Toronto (CA)

(73) Assignee: Trillium Therapeutics Inc., Toronto, Ontario (CA)

( * ) Notice: Subject to any disclaimer, the term of this patent is extended or adjusted under 35 U.S.C. 154(b) by 339 days.

(21) Appl. No.: 10/477,525

(22) PCT Filed: May 24, 2002

(86) PCT No.: PCT/CA02/00734

§ 371 (c)(1),
(2), (4) Date: Dec. 22, 2004

(87) PCT Pub. No.: WO02/095030

PCT Pub. Date: Nov. 28, 2002

(65) Prior Publication Data

US 2005/0107314 A1    May 19, 2005

Related U.S. Application Data

(60) Provisional application No. 60/292,950, filed on May 24, 2001, provisional application No. 60/369,862, filed on Apr. 5, 2002.

(51) Int. Cl.
*C07K 14/47* (2006.01)
*C07K 14/725* (2006.01)
*C07K 16/46* (2006.01)
(52) U.S. Cl. .................... 530/350; 530/387.3
(58) Field of Classification Search ............... None
See application file for complete search history.

(56) References Cited

FOREIGN PATENT DOCUMENTS

WO         WO 00/70045          * 11/2000

OTHER PUBLICATIONS

Burgess et al., J Cell Biol. 111:2129-2138, 1990.*
Lazar et al., Mol Cell Biol. 8:1247-1252, 1988.*
Metzler et al., Nature Structural Biol. 1997; 4:527-531.*
Bowie et al., Science, 247:1306-1310, 1990.*
Blazar et al., J. Immunol., 1996, 157: 3250-3259.*
Wright, G.J. et al., *Immunity*, vol. 13, 233-242, Aug. 2000.
Barclay, A.N. et al., GENSEQ, Database Accession No. GSP: AAB48017.

* cited by examiner

*Primary Examiner*—Ilia Ouspenski
(74) *Attorney, Agent, or Firm*—Bereskin & Parr; Micheline Gravelle

(57) ABSTRACT

The present invention relates to CD200 receptor isoforms and modulators thereof and their use in methods of immune modulation and pharmaceutical compositions.

10 Claims, 41 Drawing Sheets

TGCTCTGCTCGTTGTCATTGGTTTGGAGCAAGAGTCTGATGACCGGCTTAGCC
ATCCAACTGGAGGCAGACTGGAGATAAAGATAAAGACGGAGGAATAAGGAA
GAAAAGTCACTCCTGAATTGGTGAACTGAGCATAAACAAAGCTGAGCAAGCT
GGAATCACTGAGTCCACCCAGGGGTTACGAATTGTGTTTCACTAGATTCCACT
CCAGATGCATGCTTTGGGGAGGACTCCGGCTTTGACTTTGCTGATCTTCATCTA
TAATTTTGTGTCTGTGTACACCATAGTGTCTGTACAGATGGGTACAAAGGCTC
GGCTCTGCTGCCGTTCTATTCCACTGACAAAAGCAGTATTAATCACATGGATA
ATAAAGCCCAGAGGCCAGCCTTCCTGCATAATGGCCTACAAAGTAGAAACAA
AGGAGACCAATGAAACCTGCTTGGGCAGGAACATCACCTGGGCCTCCACACC
TGACCACATTCCTGACCTTCAGATCAGTGCGGTGGCCCTCCAGCATGAGGGGA
ATTACTTATGTGAGATAACAACACCTGAAGGGAATTTCCATAAAGTCTATGAC
CTCCAAGTGCTGGTGCCCCTGAAGTAACCTACTTTCTCGGGGAAAATAGAAC
TGCAGTTTGTGAGGCAATGGCAGGCAAGCCTGCTGCACAGATCTCTTGGACTC
CAGATGGGGACTGTGTCACTAAGAGTGAGTCACACAGCAATGGCACTGTGAC
TGTCAGGAGCACTTGCCACTGGGAGCAGAACAATGTGTCTGCTGTGTCCTGCA
TTGTCTCTCATTCGACTGGTAATCAGTCTCTGTCCATAGAACTGAGTAGAGGT
ACCACCAGCACCACCCCTTCCTTGCTGACCATTCTCTACGTGAAAATGGTCCTT
TTGGGGATTATTCTTCTTAAAGTGGGATTTGCTTTCTTCCAGAAGAGAAATGTT
ACCAGAACATGAATATCCAGATTTCTGGAAGCTCATTAGTCTGATGACACATA
CCAGAAAACAGCATTTGTAATCAACTTTCTCATTGGAATCCAGCTTACCCGTC
CCTGCTGTCTTCATGTTTGTTAGACACTCACCTCCAAATTCTTAACTGAGAAGG
GCTCCTGTCTAAAGGAAATATGGGGACAAATTGTGGAGCATAGACCAAAAGA
AAGGCCATCCAGAGACTGCCCCACCTAAGGACCCATCCCATATACAGACACC
AAACCCAGACACTACTGAAGATGCTGCGAAGCGTTTGCTGACAGGAGCCTGTT
ATAGCTGTCTCCTGAGAGGCTCAGCCAGAGCCTGACAAATACATAGGTAGAT
GCTTGCAGCCAACAACTGGACTGAGCAAAAAATCTCCATTGGAGGAGTTAGA
GAAAGGACTGAAGAGGGTGAAAGGGTTTGCAGCCCCATAGGAAGAACAACA
ATATCAACCAACCAGATCTCCCAGAGCTCCCAGGGACTAAATTACCAACCAA
AGGCTACACATGGAAGGACCTATGGCTCCAGCTGCTTGTGTAGCAGTGGATGG
CCTTGTTGGGCATCAGTGGAAGGAGAAACCCTTGGTCCAGTAAAGGCTTGATT
CCCTAGTGTAAGAGAATGCCAGGGCAGTGACGTGGGAGTGAGTAGGTAGGAA
GCATCCTCATAGATGCAGGAGAAAGGAGAATGGAAGAGGGTATTCTGGAGGG
GAAACTGGAAAAGGAGACAACATTTGAAATGTAAATACATAAAATATCCAAT
AAAAAATGTACAGTTGCCAGTCATGTG

CCTGAAGTAACCTACTTTCTCGGGGAAAATAGAACTGCAGTTTGTGAGGCAAT
GGCAGGCAAGCCTGCTGCACAGATCTCTTGGACTCCAGATGGGGACTGTGTCA
CTAAGAGTGAATCACACAGCAATGGCACTGTGACTGTCAAGAGCACGTGCCA
GTGGGAGCAGAATAATGTGTTTGCTGTGTCCTGCTTAGTCTCTCACTTGACTGG
TAACCGGACTCTGTTTATAGAACTGAATCAAGTGTACACCATAGTGTCTGTAC
AGATGGGTACAAAGGCTCGGCTCTGCTGCCGTTCTATTCCACTGACAAAAGCA
GTATTAATCACATGGATAATAAAGCCCAGAGGCCAGCCTTCCTGCATAATGGC
CTACAAAGTAGAAACAAAGGAGACCAATGAAACCTGCTTGGGCAGGAACATC
ACCTGGGCCTCCACACCTGACCACATTCCTGACCTTCAGATCAGTGCGGTGGC
CCTCCAGCATGAGGGGAATTACTTATGTGAGATAACAACACCTGAAGGGAAT
TTCCATAAAGTCTATGACCTCCAAGTGCTGGTGCCCCTGAAGTAACCTACTTT
CTCGGGGAAAATAGAACTGCAGTTTGTGAGGCAATGGCAGGCAAGCCTGCTG
CACAGATCTCTTGGACTCCAGATGGGGACTGTGTCACTAAGAGTGAGTCACAC
AGCAATGGCACTGTGACTGTCAGGAGCACTTGCCACTGGGAGCAGAACAATG
TGTCTGCTGTGTCCTGCATTGTCTCTCATTCGACTGGTAATCAGTCTCTGTCCA
TAGAACTGAGTAGAGGTACCACCAGCACCACCCCTTCCTTGCTGACCATTCTC
TACGTGAAAATGGTCCTTTTGGGGATTATTCTTCTTAAAGTGGGATTTGCTTTC
TTCCAGAAGAGAAATGTTACCAGAACATGAATATCCAGATTTCTGGAAGCTCA
TTAGTCTGATGACACATACCAGAAAACAGCATTTGTAATCAACTTTCTCATTG
GAATCCAGCTTACCCGTCCCTGCTGTCTTCATGTTTGTTAGACACTCACCTCCA
AATTCTTAACTGAGAAGGGCTCCTGTCTAAAGGAAATATGGGGACAAATTGTG
GAGCATAGACCAAAAGAAAGGCCATCCAGAGACTGCCCCACCTAAGGACCCA
TCCCATATACAGACACCAAACCCAGACACTACTGAAGATGCTGCGAAGCGTTT
GCTGACAGGAGCCTGTTATAGCTGTCTCCTGAGAGGCTCAGCCAGAGCCTGAC
AAATACATAGGTAGATGCTTGCAGCCAACAACTGGACTGAGCAAAAAATCTC
CATTGGAGGAGTTAGAGAAGGACTGAAGAGGGTGAAAGGGTTTGCAGCCCC
ATAGGAAGAACAACAATATCAACCAACCAGATCTCCCAGAGCTCCCAGGGAC
TAAATTACCAACCAAAGGCTACACATGGAAGGACCTATGGCTCCAGCTGCTTG
TGTAGCAGTGGATGGCCTTGTTGGGCATCAGTGGAAGGAGAAACCCTTGGTCC
AGTAAAGGCTTGATTCCCTAGTGTAAGAGAATGCCAGGGCAGTGACGTGGGA
GTGAGTAGGTAGGAAGCATCCTCATAGATGCAGGAGAAAGGAGAATGGAAG
AGGGTATTCTGGAGGGGAAACTGGAAAAGGAGACAACATTTGAAATGTAAAT
ACATAAAATATCCAATAAAAAATGTACAGTTGCCAGTCATGTG

AGGACCAAGCTGGAGTCACTGATTCCACTCAGAGGGTTACGATTTGTGCTTAA
CCTGACTCCACTCCAGATGCATGCTTTGGGGAGGACTCTGGCTTTGATGTTACT
CATCTTCATCACTATTTTGGTGCCTGAGTCAAGTTGTTCAGTGAAAGGACGGG
AGGAGATCCCACCGGATGATTCATTTCCTTTTTCAGATGATAATATCTTCCCTG
ATGGAGTGGGCGTCACCATGGAGATTGAGATTATCACTCCAGTGTCTGTACAG
ATAGGTATCAAGGCTCAGCTTTTCTGTCATCCTAGTCCATCAAAAGAAGCAAC
ACTTAGAATATGGGAAATAACTCCCAGAGACTGGCCTTCCTGCAGACTACCCT
ACAGAGCAGAGTTGCAGCAGATCAGTAAAAAAATCTGTACTGAGAGAGGAAC
CACTAGGGTCCCTGCACATCACCAGAGTTCTGACCTTCCCATCAAATCAATGG
CCCTCAAGCATGATGGGCATTACTCATGTCGGATAGAAACAACAGATGGGATT
TTCCAAGAGAGACATAGCATCCAAGTGCCAGGGGAAAATAGAACTGTAGTTT
GTGAGGCAATTGCAAGCAAGCCTGCTATGCAGATCTTGTGGACTCCAGATGAG
GACTGTGTCACTAAGAGTAAATCACACAATGACACCATGATTGTCAGGAGCA
AGTGCCACAGGGAGAAAAACAATGGCCACAGTGTGTTCTGCTTTATCTCCCAT
TTGACTGATAACTGGATTCTCTCCATGGAACAGAATCGAGGTACAACCAGCAT
CCTGCCTTCCTTGCTGAGCATTCTCTATGTGAAACTGGCTGTAACTGTTCTCAT
CGTAGGATTTGCTTTTTTCCAGAAGAGAAATTATTTCAGGTGGATCTAAAGAC
CTTGAAGAAGCCACATCTACATTGACTGAAAACAGTGTCATGACTGTGGAGA
GACGGAATATAGAATGAAACCAATGTCTTCATAGGCCATCTACACTAGCCATT
TACTTTCAACCTCTACATCTGACCTCAAATTCCTGTGACAATTAGGCAAAGCTC
CTGGAATGTGAGCAGACCTCTTGCCTCCACCAATGCAAAGTCTAAGACTGCTA
CAGCATCTGGGACATTTAGAGAAGATTCACATAATTTTTGTAGGCCAGTTAC
CTAGTGTCCTACCAATATATTTCCTAGTAAAAGTTCACGTGCCTTCTTCCACAG
TGGAGCATGTTACTCAGGGGAAACTGAATCTGTGCTCTGGATCTTTGGTCATT
CACATTTGGCTCATCCTAAATGATCTCTTATTCCTTTGGACTTCAAGCTATGTT
TTAGTGACAAAATCACTAATGGCCAAGGTTGAATTTCTCTCTCAACTTAGCAG
AGGCTTGTTCAAAAAGAAAACATCTTTTACCCACTTAGCTTTAGTATTTGTGG
ACCTGCAAAATAAACT

FIGURE 4

CD200R2a variant

MHALGRTPALTLLIFIYNFVSVYTIVSVQMGTKARLCCRSIPLTKAVLITWIIKPRGQPSCIM
AYKVETKETNETCLGRNITWASTPDHIPDLQISAVALQHEGNYLCEITTPEGNFHKVYDL
QVLVPPEVTYFLGENRTAVCEAMAGKPAAQISWTPDGDCVTKSESHSNGTVTVRSTCH
WEQNNVSAVSCIVSHSTGNQSLSIELSRGTTSTTPSLLTILYVKMVLLGIILLKVGFAFFQK
RNVTRT

Transmembrane predictions:TMHMM CD200R2a

ID Sequence
Length:248
Log-odds: 4.341453 bits

| Sequence | TMHMM1.0 | outside | 1 | 8 |
| Sequence | TMHMM1.0 | TMhelix | 9 | 31 |
| Sequence | TMHMM1.0 | inside | 32 | 218 |
| Sequence | TMHMM1.0 | TMhelix | 219 | 241 |
| Sequence | TMHMM1.0 | outside | 242 | 248 |

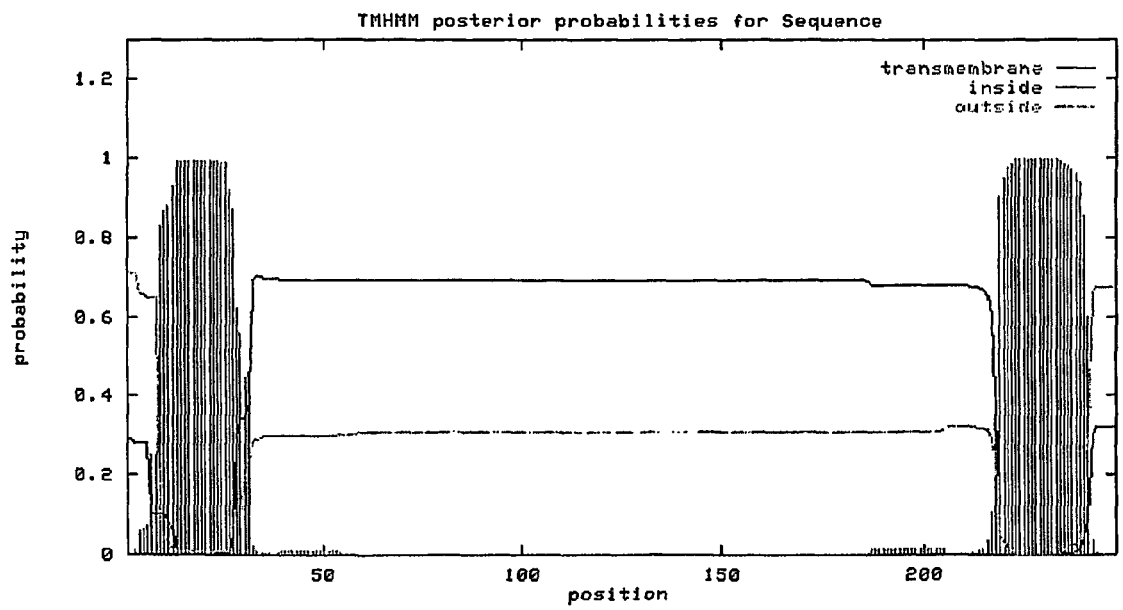

FIGURE 5

CD200R2b variant

*MAGKPAAQISWTPDGDCVTKSESHSNGTVTV*<u>KSTCQWEQNNVFAVSCLVSHLT</u>GNRT
LFIELNQVYTIVSVQMGTKARLCCRSIPLTKAVLITWIIKPRGQPSCIMAYKVETKETNETC
LGRNITWASTPDHIPDLQISAV<u>ALQHEGNYLCEITTPEGNFHKVYDLQVLVPPEVTYFLGE</u>
NRTAVCEA*MAGKPAAQISWTPDGDCVTKSESHSNGTVTV*<u>RSTCHWEQNNVSAVSCIV</u>
<u>SHSTGN</u>QSLSIELSRGTTSTTPSLLTILYVKMVLLGIILLKVGFAFFQKRNVTRT
*Bold/italic:* indicates identical repeat(31aa); <u>underline</u>:indicates conservative substitution(24aa) (through 2<sup>nd</sup>. C-domain nearly to TM domain).

Transmembrane prediction: TMHMM CD200R2b

```
#IDSequence
#Length:291
# Log-odds: 3.609545 bits
Sequence        TMHMM1.0      outside    1     261
Sequence        TMHMM1.0      TMhelix    262   284
Sequence        TMHMM1.0      inside     285   291
```

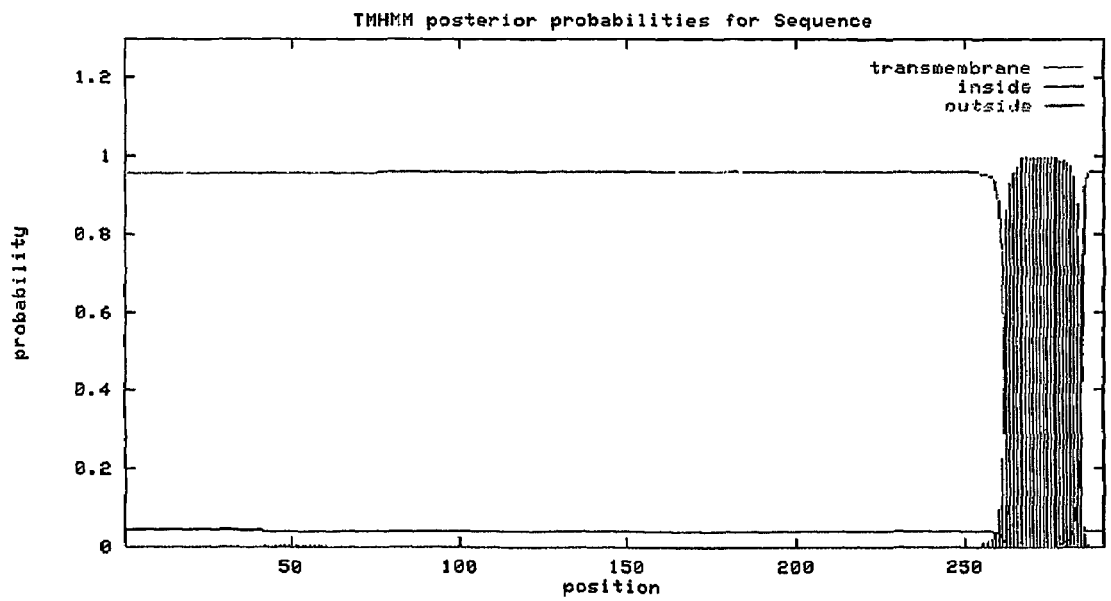

MHALGRTLALMLLIFITILVPESSCSVKGREEIPPDDSFPFSDDNIFPDGVGVTMEIEI
ITPVSVQIGIKAQLFCHPSPSKEATLRIWEITPRDWPSCRLPYRAELQQISKKICTER
GTTRVPAHHQSSDLPIKSMALKHDGHYSCRIETTDGIFQERHSIQVPGENRTVVCE
AIASKPAMQILWTPDEDCVTKSKSHNDTMIVRSKCHREKNNGHSVFCFISHLTDN
WILSMEQNRGTTSILPSLLSILYVKLAVTVLIVGFAFFQKRNYFRWI

Restoration of normoglycemia in diabetic mice by kidney capsule transplantation or pv injection of syngeneic or xenogeneic (LEW rat) islets Anti-CD200R Ig (not F(ab')$_2$ anti-CD200R) synergizes with CD200Fc in promoting normoglycemia following kidney capsule xeno-islet transplantation with CD200Fc Anti-CD200R Ig (not F(ab')₂ anti-CD200R) synergizes with CD200Fc in promoting normoglycemia following pv xeno-islet transplantation with CD200Fc CD200Fc and anti-CD200R Ig block generation of anti-LEW CTL following xeno-islet transplantation under the kidney capsule

SEQUENCE LISTING

<160> NUMBER OF SEQ ID NOS: 20

<210> SEQ ID NO 1
<211> LENGTH: 1764
<212> TYPE: DNA
<213> ORGANISM: Mus musculus
<220> FEATURE:
<221> NAME/KEY: CDS
<222> LOCATION: (214)..(960)
<223> OTHER INFORMATION:

<400> SEQUENCE: 1

```
tgctctgctc gttgtcattg gtttggagca agagtctgat gaccggctta gccatccaac      60
tggaggcaga ctggagataa agataaagac ggaggaataa ggaagaaaag tcactcctga     120
attggtgaac tgagcataaa caaagctgag caagctggaa tcactgagtc cacccagggg     180
ttacgaattg tgtttcacta gattccactc cag atg cat gct ttg ggg agg act     234
                                    Met His Ala Leu Gly Arg Thr
                                    1               5 ccg gct ttg act ttg ctg atc ttc atc tat aat ttt gtg tct gtg tac      282
Pro Ala Leu Thr Leu Leu Ile Phe Ile Tyr Asn Phe Val Ser Val Tyr
        10                  15                  20 acc ata gtg tct gta cag atg ggt aca aag gct cgg ctc tgc tgc cgt      330
Thr Ile Val Ser Val Gln Met Gly Thr Lys Ala Arg Leu Cys Cys Arg
    25                  30                  35 tct att cca ctg aca aaa gca gta tta atc aca tgg ata ata aag ccc      378
Ser Ile Pro Leu Thr Lys Ala Val Leu Ile Thr Trp Ile Ile Lys Pro
40                  45                  50                  55 aga ggc cag cct tcc tgc ata atg gcc tac aaa gta gaa aca aag gag      426
Arg Gly Gln Pro Ser Cys Ile Met Ala Tyr Lys Val Glu Thr Lys Glu
                60                  65                  70 acc aat gaa acc tgc ttg ggc agg aac atc acc tgg gcc tcc aca cct      474
Thr Asn Glu Thr Cys Leu Gly Arg Asn Ile Thr Trp Ala Ser Thr Pro
            75                  80                  85 gac cac att cct gac ctt cag atc agt gcg gtg gcc ctc cag cat gag      522
Asp His Ile Pro Asp Leu Gln Ile Ser Ala Val Ala Leu Gln His Glu
        90                  95                 100 ggg aat tac tta tgt gag ata aca aca cct gaa ggg aat ttc cat aaa      570
Gly Asn Tyr Leu Cys Glu Ile Thr Thr Pro Glu Gly Asn Phe His Lys
    105                 110                 115 gtc tat gac ctc caa gtg ctg gtg ccc cct gaa gta acc tac ttt ctc      618
Val Tyr Asp Leu Gln Val Leu Val Pro Pro Glu Val Thr Tyr Phe Leu
120                 125                 130                 135 ggg gaa aat aga act gca gtt tgt gag gca atg gca ggc aag cct gct      666
Gly Glu Asn Arg Thr Ala Val Cys Glu Ala Met Ala Gly Lys Pro Ala
                140                 145                 150 gca cag atc tct tgg act cca gat ggg gac tgt gtc act aag agt gag      714
Ala Gln Ile Ser Trp Thr Pro Asp Gly Asp Cys Val Thr Lys Ser Glu
            155                 160                 165 tca cac agc aat ggc act gtg act gtc agg agc act tgc cac tgg gag      762
Ser His Ser Asn Gly Thr Val Thr Val Arg Ser Thr Cys His Trp Glu
        170                 175                 180 cag aac aat gtg tct gct gtg tcc tgc att gtc tct cat tcg act ggt      810
Gln Asn Asn Val Ser Ala Val Ser Cys Ile Val Ser His Ser Thr Gly
    185                 190                 195 aat cag tct ctg tcc ata gaa ctg agt aga ggt acc acc agc acc acc      858
Asn Gln Ser Leu Ser Ile Glu Leu Ser Arg Gly Thr Thr Ser Thr Thr
200                 205                 210                 215 cct tcc ttg ctg acc att ctc tac gtg aaa atg gtc ctt ttg ggg att      906
```

-continued

```
Pro Ser Leu Leu Thr Ile Leu Tyr Val Lys Met Val Leu Leu Gly Ile
            220                 225                 230 att ctt ctt aaa gtg gga ttt gct ttc ttc cag aag aga aat gtt acc      954
Ile Leu Leu Lys Val Gly Phe Ala Phe Phe Gln Lys Arg Asn Val Thr
            235                 240                 245 aga aca tgaatatcca gatttctgga agctcattag tctgatgaca cataccagaa      1010
Arg Thr aacagcattt gtaatcaact ttctcattgg aatccagctt acccgtccct gctgtcttca   1070
tgtttgttag acactcacct ccaaattctt aactgagaag ggctcctgtc taaaggaaat   1130
atggggacaa attgtggagc atagaccaaa agaaaggcca tccagagact gccccaccta   1190
aggacccatc ccatatacag acaccaaacc cagacactac tgaagatgct gcgaagcgtt   1250
tgctgacagg agcctgttat agctgtctcc tgagaggctc agccagagcc tgacaaatac   1310
ataggtagat gcttgcagcc aacaactgga ctgagcaaaa atctccatt ggaggagtta    1370 gagaaaggac tgaagagggt gaaagggttt gcagccccat aggaagaaca acaatatcaa   1430
ccaaccagat ctcccagagc tcccagggac taaattacca accaaaggct acacatggaa   1490
ggacctatgg ctccagctgc ttgtgtagca gtggatggcc ttgttgggca tcagtggaag   1550
gagaaaccct tggtccagta aaggcttgat tccctagtgt aagagaatgc cagggcagtg   1610
acgtgggagt gagtaggtag gaagcatcct catagatgca ggagaaagga gaatggaaga   1670
gggtattctg gagggaaac tggaaaagga gacaacattt gaaatgtaaa tacataaaat    1730
atccaataaa aaatgtacag ttgccagtca tgtg                               1764
```

<210> SEQ ID NO 2
<211> LENGTH: 249
<212> TYPE: PRT
<213> ORGANISM: Mus musculus

<400> SEQUENCE: 2

```
Met His Ala Leu Gly Arg Thr Pro Ala Leu Thr Leu Leu Ile Phe Ile
1               5                   10                  15

Tyr Asn Phe Val Ser Val Tyr Thr Ile Val Ser Val Gln Met Gly Thr
            20                  25                  30

Lys Ala Arg Leu Cys Cys Arg Ser Ile Pro Leu Thr Lys Ala Val Leu
        35                  40                  45

Ile Thr Trp Ile Ile Lys Pro Arg Gly Gln Pro Ser Cys Ile Met Ala
    50                  55                  60

Tyr Lys Val Glu Thr Lys Glu Thr Asn Glu Thr Cys Leu Gly Arg Asn
65                  70                  75                  80

Ile Thr Trp Ala Ser Thr Pro Asp His Ile Pro Asp Leu Gln Ile Ser
                85                  90                  95

Ala Val Ala Leu Gln His Glu Gly Asn Tyr Leu Cys Glu Ile Thr Thr
            100                 105                 110

Pro Glu Gly Asn Phe His Lys Val Tyr Asp Leu Gln Val Leu Val Pro
        115                 120                 125

Pro Glu Val Thr Tyr Phe Leu Gly Glu Asn Arg Thr Ala Val Cys Glu
    130                 135                 140

Ala Met Ala Gly Lys Pro Ala Ala Gln Ile Ser Trp Thr Pro Asp Gly
145                 150                 155                 160

Asp Cys Val Thr Lys Ser Glu Ser His Ser Asn Gly Thr Val Thr Val
                165                 170                 175

Arg Ser Thr Cys His Trp Glu Gln Asn Asn Val Ser Ala Val Ser Cys
            180                 185                 190
```

```
Ile Val Ser His Ser Thr Gly Asn Gln Ser Leu Ser Ile Glu Leu Ser
            195                 200                 205

Arg Gly Thr Thr Ser Thr Thr Pro Ser Leu Leu Thr Ile Leu Tyr Val
        210                 215                 220

Lys Met Val Leu Leu Gly Ile Ile Leu Leu Lys Val Gly Phe Ala Phe
225                 230                 235                 240

Phe Gln Lys Arg Asn Val Thr Arg Thr
                245

<210> SEQ ID NO 3
<211> LENGTH: 1982
<212> TYPE: DNA
<213> ORGANISM: Mus musculus
<220> FEATURE:
<221> NAME/KEY: CDS
<222> LOCATION: (52)..(930)
<223> OTHER INFORMATION:

<400> SEQUENCE: 3
cctgaagtaa cctactttct cggggaaaat agaactgcag tttgtgaggc a atg gca      57
                                                         Met Ala
                                                           1 ggc aag cct gct gca cag atc tct tgg act cca gat ggg gac tgt gtc     105
Gly Lys Pro Ala Ala Gln Ile Ser Trp Thr Pro Asp Gly Asp Cys Val
        5                  10                  15 act aag agt gaa tca cac agc aat ggc act gtg act gtc aag agc acg     153
Thr Lys Ser Glu Ser His Ser Asn Gly Thr Val Thr Val Lys Ser Thr
 20                  25                  30 tgc cag tgg gag cag aat aat gtg ttt gct gtg tcc tgc tta gtc tct     201
Cys Gln Trp Glu Gln Asn Asn Val Phe Ala Val Ser Cys Leu Val Ser
 35                  40                  45                  50 cac ttg act ggt aac cgg act ctg ttt ata gaa ctg aat caa gtg tac     249
His Leu Thr Gly Asn Arg Thr Leu Phe Ile Glu Leu Asn Gln Val Tyr
                 55                  60                  65 acc ata gtg tct gta cag atg ggt aca aag gct cgg ctc tgc tgc cgt     297
Thr Ile Val Ser Val Gln Met Gly Thr Lys Ala Arg Leu Cys Cys Arg
             70                  75                  80 tct att cca ctg aca aaa gca gta tta atc aca tgg ata ata aag ccc     345
Ser Ile Pro Leu Thr Lys Ala Val Leu Ile Thr Trp Ile Ile Lys Pro
         85                  90                  95 aga ggc cag cct tcc tgc ata atg gcc tac aaa gta gaa aca aag gag     393
Arg Gly Gln Pro Ser Cys Ile Met Ala Tyr Lys Val Glu Thr Lys Glu
    100                 105                 110 acc aat gaa acc tgc ttg ggc agg aac atc acc tgg gcc tcc aca cct     441
Thr Asn Glu Thr Cys Leu Gly Arg Asn Ile Thr Trp Ala Ser Thr Pro
115                 120                 125                 130 gac cac att cct gac ctt cag atc agt gcg gtg gcc ctc cag cat gag     489
Asp His Ile Pro Asp Leu Gln Ile Ser Ala Val Ala Leu Gln His Glu
                135                 140                 145 ggg aat tac tta tgt gag ata aca aca cct gaa ggg aat ttc cat aaa     537
Gly Asn Tyr Leu Cys Glu Ile Thr Thr Pro Glu Gly Asn Phe His Lys
            150                 155                 160 gtc tat gac ctc caa gtg ctg gtg ccc cct gaa gta acc tac ttt ctc     585
Val Tyr Asp Leu Gln Val Leu Val Pro Pro Glu Val Thr Tyr Phe Leu
        165                 170                 175 ggg gaa aat aga act gca gtt tgt gag gca atg gca ggc aag cct gct     633
Gly Glu Asn Arg Thr Ala Val Cys Glu Ala Met Ala Gly Lys Pro Ala
    180                 185                 190 gca cag atc tct tgg act cca gat ggg gac tgt gtc act aag agt gag     681
Ala Gln Ile Ser Trp Thr Pro Asp Gly Asp Cys Val Thr Lys Ser Glu
```

| | | |
|---|---|---|
| tca cac agc aat ggc act gtg act gtc agg agc act tgc cac tgg gag<br>Ser His Ser Asn Gly Thr Val Thr Val Arg Ser Thr Cys His Trp Glu<br>                 215                      220                   225 | 729 |
| cag aac aat gtg tct gct gtg tcc tgc att gtc tct cat tcg act ggt<br>Gln Asn Asn Val Ser Ala Val Ser Cys Ile Val Ser His Ser Thr Gly<br>  230                            235                      240 | 777 |
| aat cag tct ctg tcc ata gaa ctg agt aga ggt acc acc agc acc acc<br>Asn Gln Ser Leu Ser Ile Glu Leu Ser Arg Gly Thr Thr Ser Thr Thr<br>          245                      250                      255 | 825 |
| cct tcc ttg ctg acc att ctc tac gtg aaa atg gtc ctt ttg ggg att<br>Pro Ser Leu Leu Thr Ile Leu Tyr Val Lys Met Val Leu Leu Gly Ile<br>260                       265                      270 | 873 |
| att ctt ctt aaa gtg gga ttt gct ttc ttc cag aag aga aat gtt acc<br>Ile Leu Leu Lys Val Gly Phe Ala Phe Phe Gln Lys Arg Asn Val Thr<br>275                       280                      285                      290 | 921 |
| aga aca tga atatccagat tctggaagc tcattagtct gatgacacat<br>Arg Thr | 970 |
| accagaaaac agcatttgta atcaactttc tcattggaat ccagcttacc cgtccctgct | 1030 |
| gtcttcatgt ttgttagaca ctcacctcca aattcttaac tgagaagggc tcctgtctaa | 1090 |
| aggaaatatg gggacaaatt gtggagcata gaccaaaaga aaggccatcc agagactgcc | 1150 |
| ccacctaagg acccatccca tatacagaca ccaaacccag acactactga agatgctgcg | 1210 |
| aagcgtttgc tgacaggagc ctgttatagc tgtctcctga gaggctcagc cagagcctga | 1270 |
| caaatacata ggtagatgct tgcagccaac aactggactg agcaaaaaat ctccattgga | 1330 |
| ggagttagag aaaggactga agagggtgaa agggtttgca gccccatagg aagaacaaca | 1390 |
| atatcaacca accagatctc ccagagctcc cagggactaa attaccaacc aaaggctaca | 1450 |
| catggaagga cctatggctc cagctgcttg tgtagcagtg gatggccttg ttgggcatca | 1510 |
| gtggaaggag aaacccttgg tccagtaaag gcttgattcc ctagtgtaag agaatgccag | 1570 |
| ggcagtgacg tgggagtgag taggtaggaa gcatcctcat agatgcagga gaaaggagaa | 1630 |
| tggaagaggg tattctggag gggaaactgg aaaaggagac aacatttgaa atgtaaatac | 1690 |
| ataaaatatc caataaaaaa tgtacagttg ccagtcatgt gaaaaaaaaa aaaaaaaaa | 1750 |
| aaaaaaaggg cggccgcaag cttattccct ttagtgaggg ttaattttag cttggcactg | 1810 |
| gccgtcgttt tacaacgtcg tgactgggaa aaccctggcg ttacccaact taatcgcctt | 1870 |
| gcagcacatc ccccttttcgc cagctggcgt aatagcgaag aggcccgcac cgatcgccct | 1930 |
| tcccaacagt tgcgcagcct gaatggcgaa tgggacgcgc cctgtagcgg cg | 1982 |

<210> SEQ ID NO 4
<211> LENGTH: 292
<212> TYPE: PRT
<213> ORGANISM: Mus musculus

<400> SEQUENCE: 4

Met Ala Gly Lys Pro Ala Ala Gln Ile Ser Trp Thr Pro Asp Gly Asp
1                5                    10                   15

Cys Val Thr Lys Ser Glu Ser His Ser Asn Gly Thr Val Thr Val Lys
                20                    25                    30

Ser Thr Cys Gln Trp Glu Gln Asn Asn Val Phe Ala Val Ser Cys Leu
          35                    40                    45

Val Ser His Leu Thr Gly Asn Arg Thr Leu Phe Ile Glu Leu Asn Gln
    50                    55                    60

```
Val Tyr Thr Ile Val Ser Val Gln Met Gly Thr Lys Ala Arg Leu Cys
 65                  70                  75                  80

Cys Arg Ser Ile Pro Leu Thr Lys Ala Val Leu Ile Thr Trp Ile Ile
                 85                  90                  95

Lys Pro Arg Gly Gln Pro Ser Cys Ile Met Ala Tyr Lys Val Glu Thr
            100                 105                 110

Lys Glu Thr Asn Glu Thr Cys Leu Gly Arg Asn Ile Thr Trp Ala Ser
        115                 120                 125

Thr Pro Asp His Ile Pro Asp Leu Gln Ile Ser Ala Val Ala Leu Gln
    130                 135                 140

His Glu Gly Asn Tyr Leu Cys Glu Ile Thr Thr Pro Glu Gly Asn Phe
145                 150                 155                 160

His Lys Val Tyr Asp Leu Gln Val Leu Val Pro Pro Glu Val Thr Tyr
                165                 170                 175

Phe Leu Gly Glu Asn Arg Thr Ala Val Cys Glu Ala Met Ala Gly Lys
            180                 185                 190

Pro Ala Ala Gln Ile Ser Trp Thr Pro Asp Gly Asp Cys Val Thr Lys
        195                 200                 205

Ser Glu Ser His Ser Asn Gly Thr Val Thr Val Arg Ser Thr Cys His
    210                 215                 220

Trp Glu Gln Asn Asn Val Ser Ala Val Ser Cys Ile Val Ser His Ser
225                 230                 235                 240

Thr Gly Asn Gln Ser Leu Ser Ile Glu Leu Ser Arg Gly Thr Thr Ser
                245                 250                 255

Thr Thr Pro Ser Leu Leu Thr Ile Leu Tyr Val Lys Met Val Leu Leu
            260                 265                 270

Gly Ile Ile Leu Leu Lys Val Gly Phe Ala Phe Phe Gln Lys Arg Asn
        275                 280                 285

Val Thr Arg Thr
    290

<210> SEQ ID NO 5
<211> LENGTH: 1449
<212> TYPE: DNA
<213> ORGANISM: Mus musculus
<220> FEATURE:
<221> NAME/KEY: CDS
<222> LOCATION: (70)..(894)
<223> OTHER INFORMATION:

<400> SEQUENCE: 5
aggaccaagc tggagtcact gattccactc agagggttac gatttgtgct taacctgact      60 ccactccag atg cat gct ttg ggg agg act ctg gct ttg atg tta ctc atc     111
           Met His Ala Leu Gly Arg Thr Leu Ala Leu Met Leu Leu Ile
             1               5                  10 ttc atc act att ttg gtg cct gag tca agt tgt tca gtg aaa gga cgg       159
Phe Ile Thr Ile Leu Val Pro Glu Ser Ser Cys Ser Val Lys Gly Arg
 15                  20                  25                  30 gag gag atc cca ccg gat gat tca ttt cct ttt tca gat gat aat atc       207
Glu Glu Ile Pro Pro Asp Asp Ser Phe Pro Phe Ser Asp Asp Asn Ile
                 35                  40                  45 ttc cct gat gga gtg ggc gtc acc atg gag att gag att atc act cca       255
Phe Pro Asp Gly Val Gly Val Thr Met Glu Ile Glu Ile Ile Thr Pro
            50                  55                  60 gtg tct gta cag ata ggt atc aag gct cag ctt ttc tgt cat cct agt       303
Val Ser Val Gln Ile Gly Ile Lys Ala Gln Leu Phe Cys His Pro Ser
        65                  70                  75
```

| | | |
|---|---|---|
| cca tca aaa gaa gca aca ctt aga ata tgg gaa ata act ccc aga gac<br>Pro Ser Lys Glu Ala Thr Leu Arg Ile Trp Glu Ile Thr Pro Arg Asp<br>      80                        85                    90 | | 351 |
| tgg cct tcc tgc aga cta ccc tac aga gca gag ttg cag cag atc agt<br>Trp Pro Ser Cys Arg Leu Pro Tyr Arg Ala Glu Leu Gln Gln Ile Ser<br>95                      100                   105                110 | | 399 |
| aaa aaa atc tgt act gag aga gga acc act agg gtc cct gca cat cac<br>Lys Lys Ile Cys Thr Glu Arg Gly Thr Thr Arg Val Pro Ala His His<br>               115                    120                   125 | | 447 |
| cag agt tct gac ctt ccc atc aaa tca atg gcc ctc aag cat gat ggg<br>Gln Ser Ser Asp Leu Pro Ile Lys Ser Met Ala Leu Lys His Asp Gly<br>          130                    135                  140 | | 495 |
| cat tac tca tgt cgg ata gaa aca aca gat ggg att ttc caa gag aga<br>His Tyr Ser Cys Arg Ile Glu Thr Thr Asp Gly Ile Phe Gln Glu Arg<br>               145                    150                   155 | | 543 |
| cat agc atc caa gtg cca ggg gaa aat aga act gta gtt tgt gag gca<br>His Ser Ile Gln Val Pro Gly Glu Asn Arg Thr Val Val Cys Glu Ala<br>          160                    165                  170 | | 591 |
| att gca agc aag cct gct atg cag atc ttg tgg act cca gat gag gac<br>Ile Ala Ser Lys Pro Ala Met Gln Ile Leu Trp Thr Pro Asp Glu Asp<br>175                    180                   185                190 | | 639 |
| tgt gtc act aag agt aaa tca cac aat gac acc atg att gtc agg agc<br>Cys Val Thr Lys Ser Lys Ser His Asn Asp Thr Met Ile Val Arg Ser<br>               195                    200                   205 | | 687 |
| aag tgc cac agg gag aaa aac aat ggc cac agt gtg ttc tgc ttt atc<br>Lys Cys His Arg Glu Lys Asn Asn Gly His Ser Val Phe Cys Phe Ile<br>          210                    215                  220 | | 735 |
| tcc cat ttg act gat aac tgg att ctc tcc atg gaa cag aat cga ggt<br>Ser His Leu Thr Asp Asn Trp Ile Leu Ser Met Glu Gln Asn Arg Gly<br>               225                    230                   235 | | 783 |
| aca acc agc atc ctg cct tcc ttg ctg agc att ctc tat gtg aaa ctg<br>Thr Thr Ser Ile Leu Pro Ser Leu Leu Ser Ile Leu Tyr Val Lys Leu<br>          240                    245                  250 | | 831 |
| gct gta act gtt ctc atc gta gga ttt gct ttt ttc cag aag aga aat<br>Ala Val Thr Val Leu Ile Val Gly Phe Ala Phe Phe Gln Lys Arg Asn<br>255                    260                   265                270 | | 879 |
| tat ttc agg tgg atc taaagacctt gaagaagcca catctacatt gactgaaaac<br>Tyr Phe Arg Trp Ile<br>               275 | | 934 |
| agtgtcatga ctgtggagag acggaatata gaatgaaacc aatgtcttca taggccatct | | 994 |
| acactagcca tttactttca acctctacat ctgacctcaa attcctgtga caattaggca | | 1054 |
| aagctcctgg aatgtgagca gacctcttgc ctccaccaat gcaaagtcta agactgctac | | 1114 |
| agcatctggg acatttagag aagattcaca taatttttg taggccagtt acctagtgtc | | 1174 |
| ctaccaatat atttcctagt aaaagttcac gtgccttctt ccacagtgga gcatgttact | | 1234 |
| caggggaaac tgaatctgtg ctctggatct ttggtcattc acatttggct catcctaaat | | 1294 |
| gatctcttat tcctttggac ttcaagctat gttttagtga caaaatcact aatggccaag | | 1354 |
| gttgaatttc tctctcaact tagcagaggc ttgttcaaaa agaaaacatc ttttacccac | | 1414 |
| ttagctttag tatttgtgga cctgcaaaat aaact | | 1449 |

<210> SEQ ID NO 6
<211> LENGTH: 275
<212> TYPE: PRT
<213> ORGANISM: Mus musculus

<400> SEQUENCE: 6

Met His Ala Leu Gly Arg Thr Leu Ala Leu Met Leu Leu Ile Phe Ile

```
                1               5                  10                  15
Thr Ile Leu Val Pro Glu Ser Ser Cys Ser Val Lys Gly Arg Glu Glu
                    20                  25                  30

Ile Pro Pro Asp Asp Ser Phe Pro Phe Ser Asp Asp Asn Ile Phe Pro
                    35                  40                  45

Asp Gly Val Gly Val Thr Met Glu Ile Glu Ile Ile Thr Pro Val Ser
                    50                  55                  60

Val Gln Ile Gly Ile Lys Ala Gln Leu Phe Cys His Pro Ser Pro Ser
 65                 70                  75                  80

Lys Glu Ala Thr Leu Arg Ile Trp Glu Ile Thr Pro Arg Asp Trp Pro
                    85                  90                  95

Ser Cys Arg Leu Pro Tyr Arg Ala Glu Leu Gln Gln Ile Ser Lys Lys
                    100                 105                 110

Ile Cys Thr Glu Arg Gly Thr Thr Arg Val Pro Ala His His Gln Ser
                    115                 120                 125

Ser Asp Leu Pro Ile Lys Ser Met Ala Leu Lys His Asp Gly His Tyr
                    130                 135                 140

Ser Cys Arg Ile Glu Thr Thr Asp Gly Ile Phe Gln Glu Arg His Ser
145                 150                 155                 160

Ile Gln Val Pro Gly Glu Asn Arg Thr Val Val Cys Glu Ala Ile Ala
                    165                 170                 175

Ser Lys Pro Ala Met Gln Ile Leu Trp Thr Pro Asp Glu Asp Cys Val
                    180                 185                 190

Thr Lys Ser Lys Ser His Asn Asp Thr Met Ile Val Arg Ser Lys Cys
                    195                 200                 205

His Arg Glu Lys Asn Asn Gly His Ser Val Phe Cys Phe Ile Ser His
                    210                 215                 220

Leu Thr Asp Asn Trp Ile Leu Ser Met Glu Gln Asn Arg Gly Thr Thr
225                 230                 235                 240

Ser Ile Leu Pro Ser Leu Leu Ser Ile Leu Tyr Val Lys Leu Ala Val
                    245                 250                 255

Thr Val Leu Ile Val Gly Phe Ala Phe Phe Gln Lys Arg Asn Tyr Phe
                    260                 265                 270

Arg Trp Ile
        275

<210> SEQ ID NO 7
<211> LENGTH: 23
<212> TYPE: DNA
<213> ORGANISM: artificial sequence
<220> FEATURE:
<223> OTHER INFORMATION: CD200R2 anti-sense primer

<400> SEQUENCE: 7
tcaggaatgt ggtcaggtgt gga                                          23

<210> SEQ ID NO 8
<211> LENGTH: 24
<212> TYPE: DNA
<213> ORGANISM: Artificial Sequence
<220> FEATURE:
<223> OTHER INFORMATION: CD200R3 anti-sense primer

<400> SEQUENCE: 8
ctccctgtgg cacttgctcc tgac                                         24

<210> SEQ ID NO 9
```

```
<211> LENGTH: 23
<212> TYPE: DNA
<213> ORGANISM: Artificial Sequence
<220> FEATURE:
<223> OTHER INFORMATION: CD200R2 anti-sense primer

<400> SEQUENCE: 9
tggtctcctt tgtttctact ttg                                             23

<210> SEQ ID NO 10
<211> LENGTH: 23
<212> TYPE: DNA
<213> ORGANISM: Artificial Sequence
<220> FEATURE:
<223> OTHER INFORMATION: CD200R3 anti-sense primer

<400> SEQUENCE: 10
cttgcaattg cctcacaaac tac                                             23

<210> SEQ ID NO 11
<211> LENGTH: 21
<212> TYPE: DNA
<213> ORGANISM: Artificial Sequence
<220> FEATURE:
<223> OTHER INFORMATION: R2RT-PCR-S sense primer

<400> SEQUENCE: 11
ggagaccaat gaaacctgct t                                               21

<210> SEQ ID NO 12
<211> LENGTH: 21
<212> TYPE: DNA
<213> ORGANISM: Artificial Sequence
<220> FEATURE:
<223> OTHER INFORMATION: R2RT-PCR-AS antisense primer

<400> SEQUENCE: 12
aataatcccc aaaaggacca t                                               21

<210> SEQ ID NO 13
<211> LENGTH: 21
<212> TYPE: DNA
<213> ORGANISM: Artificial Sequence
<220> FEATURE:
<223> OTHER INFORMATION: R3RT-PCR-AS sense primer

<400> SEQUENCE: 13
catctgggac atttagagaa g                                               21

<210> SEQ ID NO 14
<211> LENGTH: 21
<212> TYPE: DNA
<213> ORGANISM: Artificial Sequence
<220> FEATURE:
<223> OTHER INFORMATION: R3RT-PCR-AS antisense primer

<400> SEQUENCE: 14
ttgaagtcca aaggaataag a                                               21

<210> SEQ ID NO 15
<211> LENGTH: 24
<212> TYPE: PRT
<213> ORGANISM: Artificial Sequence
<220> FEATURE:
<223> OTHER INFORMATION: CD200R1

<400> SEQUENCE: 15
```

```
Ser Thr Pro Asp His Ser Pro Glu Leu Gln Ile Ser Ala Val Thr Leu
1               5                   10                  15

Gln His Glu Gly Thr Tyr Thr Cys
            20
```

<210> SEQ ID NO 16
<211> LENGTH: 19
<212> TYPE: PRT
<213> ORGANISM: Artificial Sequence
<220> FEATURE:
<223> OTHER INFORMATION: CD200R2a

<400> SEQUENCE: 16

```
Cys Glu Ala Met Ala Gly Lys Pro Ala Ala Gln Ile Ser Trp Thr Pro
1               5                   10                  15

Asp Gly Asp
```

<210> SEQ ID NO 17
<211> LENGTH: 19
<212> TYPE: PRT
<213> ORGANISM: Artificial Sequence
<220> FEATURE:
<223> OTHER INFORMATION: CD200R2b

<400> SEQUENCE: 17

```
Lys Pro Arg Gly Gln Pro Ser Cys Ile Met Ala Tyr Lys Val Glu Thr
1               5                   10                  15

Lys Glu Thr
```

<210> SEQ ID NO 18
<211> LENGTH: 21
<212> TYPE: PRT
<213> ORGANISM: Artificial Sequence
<220> FEATURE:
<223> OTHER INFORMATION: CD200R3a

<400> SEQUENCE: 18

```
Cys Ser Val Lys Gly Arg Glu Glu Ile Pro Pro Asp Asp Ser Phe Pro
1               5                   10                  15

Phe Ser Asp Asp Asn
            20
```

<210> SEQ ID NO 19
<211> LENGTH: 24
<212> TYPE: PRT
<213> ORGANISM: Artificial Sequence
<220> FEATURE:
<223> OTHER INFORMATION: CD200R3b

<400> SEQUENCE: 19

```
Leu Gln Gln Ile Ser Lys Lys Ile Cys Thr Glu Arg Gly Thr Thr Arg
1               5                   10                  15

Val Pro Ala His His Gln Ser Ser
            20
```

<210> SEQ ID NO 20
<211> LENGTH: 21
<212> TYPE: PRT
<213> ORGANISM: Artificial Sequence
<220> FEATURE:
<223> OTHER INFORMATION: CD200R1

<400> SEQUENCE: 20

```
-continued

Cys Thr Lys Ala Tyr Lys Lys Glu Thr Asn Glu Thr Lys Glu Thr Asn
1               5                   10                  15
Cys Thr Asp Glu Arg
            20
```

CD200 RECEPTORS

FIELD OF THE INVENTION

The present invention relates to CD200 receptor molecules and modulators of CD200 receptors as well as methods and compositions for immune modulation using the CD200 receptor molecules and modulators thereof.

BACKGROUND OF THE INVENTION

The immune system protects the body from infectious agents and disease and is critical to our survival. However, in certain instances, the immune system can be the cause of illness. One example is in autoimmune disease wherein the immune system attacks its own host tissues, in many instances causing debilitating illness and sometimes resulting in death. Examples of autoimmune diseases include multiple sclerosis, type 1 insulin-dependent diabetes mellitus, lupus erythematosus and arthritis. A second example where the immune system can cause illness is during tissue or organ transplantation. Except in the cases of genetically identical animals, such as monozygotic twins, tissue and organ transplants are rejected by the recipient's immune system as foreign. The immune reaction against transplants is even more pronounced in transplantation across species or xenotransplantation. A third example where the immune system harms the host is during an allergic reaction where the immune system is activated by a generally innocuous antigen causing inflammation and in some cases tissue damage. A fourth example where the immune system is involved is in fetal loss.

In order to inhibit the detrimental immune reactions during transplantation, autoimmune disease and allergic reactions, immunosuppressive drugs (such as cyclosporin A, tacrolimas, and corticosteroids) or antibody therapies (such as anti-T cell antibodies) are generally administered. Unfortunately, these non-specific modes of immunosuppression generally have undesirable side effects. For example, cyclosporin may cause decreased renal function, hypertension, toxicity and it must be administered for the life of the patient. Corticosteroids may cause decreased resistance to infection, painful arthritis, osteoporosis and cataracts. The anti-T cell antibodies may cause fever, hypertension, diarrhea or sterile meningitis and are quite expensive.

In view of the problems associated with immunosuppression, there has been an interest in developing methods or therapies that induce unresponsiveness or tolerance in the host to a transplant, to "self" tissues in autoimmune disease and to harmless antigens associated with allergies. The inventors have been studying the mechanisms involved in transplant rejection and have developed methods for inducing a state of antigen-specific immunological tolerance in transplantation. In particular, in animal allograft models, the inventors have demonstrated that graft survival, such as renal and skin allograft survival, can be increased if the recipient animal is given a pre-transplant infusion via the portal vein of irradiated spleen cells from the donor animal (2,3). In contrast, a pre-transplant infusion via the tail vein does not prolong graft survival. Increased graft survival was further shown to be in turn associated with increased expression of a number of distinct mRNAs (4), one of which encodes CD200 (previously called OX2), a molecule expressed on the surface of dendritic cells (5).

The CD200 protein (also known as OX2) has a high degree of homology to molecules of the immunoglobulin gene family, which includes molecules important in lymphocyte antigen recognition and cell-cell interaction (e.g. CD4, CD8, ICAMs, VCAMs), as well as adhesion receptor molecules (NCAMs) in the nervous system. However, prior to the present inventors, the function of the CD200 protein was largely unknown. The present inventors showed subsequently that infusion of anti-CD200 monoclonal antibodies from the time of transplantation blocks the protective effect of pv immunization in mice receiving renal allografts (4) and rats receiving SIT (6), and the polarization to type-2 cytokine production seen in these models (4, 6). A soluble immunoadhesin, in which the extracellular domain of CD200 was linked to a murine IgG2aFc region, inhibited T-cell allostimulation and type-1 cytokine production (IL-2, IFNγ) in vitro and in vivo (1). Since the intracellular domain of CD200 lacks signalling motifs, or any docking sites for adapter molecules which might engage an intracellular signalling cascade, the present inventors suggest that these and other data (4,7,25) are consistent with the idea that engagement of a receptor for CD200 (CD200R) by CD200 may deliver key immunoregulatory signals (36).

T-cells are activated after concomitant engagement of TCRs with antigen presented on APC in association with MHC molecules and the delivery of costimulatory signals resulting from the interaction of several ligand:coreceptor complexes (8-11). Major positive costimulatory interactions include the following: CD40L with CD40, and CD28 with CD80/CD86; CTLA4 interactions with CD80/CD86 may deliver a negative signal (12-17). While positive costimulatory signals are clearly important in T-cell triggering, blocking this costimulation alone, and/or facilitating signalling via CTLA4, has not reproducibly induced tolerance. This may reflect the need for other molecules (such as CD200) in active immunoregulation (4). In recent studies the inventors reported that dendritic cells (DC) expressing CD200, triggered an immunoregulatory function leading to increased allograft survival. Moreover, these cells were physically distinguishable from those DC with optimal allostimulatory capacity (7).

Early attempts to characterize CD200R by Preston et al. (18) were performed by constructing a soluble chimeric protein with the extracellular domains of CD200 engineered onto domains 3+4 of rat CD4 antigen. In order to detect weak interactions, the chimeric protein was coupled to fluorescent covaspheres to ensure an avid display of CD200. These CD200 covaspheres were reported to bind to macrophages but not other cell types. The specificity of the interaction was documented by inhibition studies using Fab fragments of the CD200 monoclonal antibody (mAb). Using site-directed mutagenesis this group further reported results suggesting that the ligand-binding domain of CD200 was in the $NH_2$-terminal domain of the extracellular region of CD200.

Recently, Barclay et al. reported several forms of the CD200R (WO 00/70045, published Nov. 23, 2000).

SUMMARY OF THE INVENTION

The present inventors have studied the CD200 receptor (CD200R) and revealed evidence for a family of CD200Rs. The present inventors have now determined the full length sequence for three isoforms of the murine CD200 receptor called CD200R2a, CD200R2b and CD200R3a.

Accordingly, in one aspect, the present invention provides an isolated CD200R2a, CD200R2b or CD200R3a or a homolog or analog thereof. In one embodiment, the present invention provides an isolated CD200R2a having the nucleic acid shown in FIG. 1 (SEQ ID NO:1) or a homolog or analog thereof. In another embodiment, the present invention provides an isolated CD200R2b having the nucleic acid sequence found in FIG. 2 (SEQ ID NO:3) or a homolog or analog thereof. In a further embodiment, the present invention provides an isolated CD200R3a having the nucleic acid shown in FIG. 3 (SEQ ID NO:5) or a homolog or analog thereof.

In another aspect, the invention includes a method of immune modulation comprising administering an effective amount of an CD200R2a, CD200R2b or CD200R3a molecule to a cell or animal in need thereof.

In one embodiment, the CD200 receptor may be co-administered with a CD200 peptide or a nucleic acid sequence coding for a CD200 peptide. Preferably, a CD200 peptide is administered and more preferably, the CD200 peptide is a soluble fusion protein, such as CD200:Fc.

The inventors have also prepared antibodies to the different isoforms of CD200R. Accordingly, the present invention includes an antibody that binds to CD200R2a, CD200R2b or CD200R3a.

The present inventors have also shown that administering cross-linking antibodies to a CD200 receptor enhances immune suppression as seen by prolonged graft survival and the prevention of autoimmune disease. Accordingly, the present invention provides a method of suppressing an immune response comprising administering an effective amount of a CD200 receptor agonist to a cell or animal in need thereof.

In one embodiment, the agonist is an antibody that crosslinks a CD200 receptor such as a whole anti-CD200 receptor Ig. Accordingly, the present invention provides a method of suppressing an immune response comprising administering an effective amount of an antibody that crosslinks a CD200 receptor to a cell or animal in need thereof. In a specific embodiment, the antibody binds a CD200R selected from CD200R2a, CD200R2b or CD200R3a.

The inventors have also shown that administering antibody fragments (e.g. Fab or F(ab')$_2$ fragments) that bind to a CD200 receptor inhibits the immune suppression caused by CD200. Accordingly, in another aspect, the present invention provides a method of inhibiting immune suppression by administering an effective amount of a CD200 receptor antagonist to a cell or animal in need thereof. Preferably, the antagonist is an agent that inhibits the interaction of the CD200 receptor with CD200.

An agent that inhibits the interaction of the CD200 receptor and CD200 may be an antibody that binds to the CD200 receptor. Accordingly, the invention includes a method of inhibiting immune suppression comprising administering an effective amount of an antibody that binds to an CD200 receptor to a cell or animal in need thereof. The antibody is preferably an antibody fragment such as an F(ab')$_2$ or Fab fragment.

In yet another aspect, the present invention includes screening methods for identifying substances which are capable of modulating CD200 receptors. In particular, the methods may be used to identify substances which are capable of binding to and augmenting or attenuating the effects of CD200 or the CD200 receptors (i.e. agonists). Alternatively, the methods may be used to identify substances which are capable of binding to CD200 receptor and which inhibit the effects of CD200 or a CD200 receptor (i.e. antagonists).

Accordingly, the invention provides a method of identifying substances which bind with a CD200 receptor, comprising the steps of:

(a) reacting the CD200 receptor and a test substance, under conditions which allow for formation of a complex, and (b) assaying for complexes of the CD200 receptor and the test substance, for free substance, and for non-complexed CD200 receptor, wherein the presence of complexes indicates that the test substance is capable of binding the CD200 receptor. In a specific embodiment the CD200R is selected from CD200R2a, CD200R2b or CD200R3a.

The invention also includes screening assays for identifying agonists or antagonists of a CD200R comprising the steps of:

(a) incubating a test substance with a CD200R; and (b) determining whether the test substance activates or inhibits the function of the CD200R.

In another embodiment, agonists and/or antagonists of the binding of CD200 to its receptor can be identified. Therefore the invention also contemplates a method for assaying for an agonist or antagonist of the binding of CD200 with its receptor or other CD200 ligands such as antibodies to CD200. The agonist or antagonist may be an endogenous physiological substance or it may be a natural or synthetic substance. Accordingly the invention provides a method for identifying an antagonist or agonist of CD200 binding comprising the steps of:

(a) reacting CD200, a known binding target, preferably an CD200 receptor, and a potential antagonist or agonist; and (b) determining the amount of CD200 bound to the binding target and comparing this with a control in the absence of the antagonist or agonist.

The present invention also includes the pharmaceutical compositions comprising any of the above molecules that modulate CD200 reeptors for use in immune modulation. The pharmaceutical compositions can further comprise an CD200 peptide, preferably CD200:Fc, or nucleic acid encoding a CD200 peptide. The pharmaceutical compositions can further comprise a suitable diluent or carrier.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 (and SEQ ID NO:1) shows the nucleic acid sequence of CD200R2a.

FIG. 2 (and SEQ ID NO:3) shows the nucleic acid sequence of CD200R2b.

FIG. 3 (and SEQ ID NO:5) shows the nucleic acid sequence of CD200R3a.

FIG. 4 (and SEQ ID NO:2) shows the amino acid sequence of CD200R2a and the transmembrane prediction.

FIG. 5 (and SEQ ID NO:4) shows the amino add sequence of CD200R2b and the transmembrane prediction.

FIG. 6 (and SEQ ID NO:6) shows the amino acid sequence of CD200R3a.

DETAILED DESCRIPTION OF THE INVENTION

I. CD200 Receptors

Figure 7:
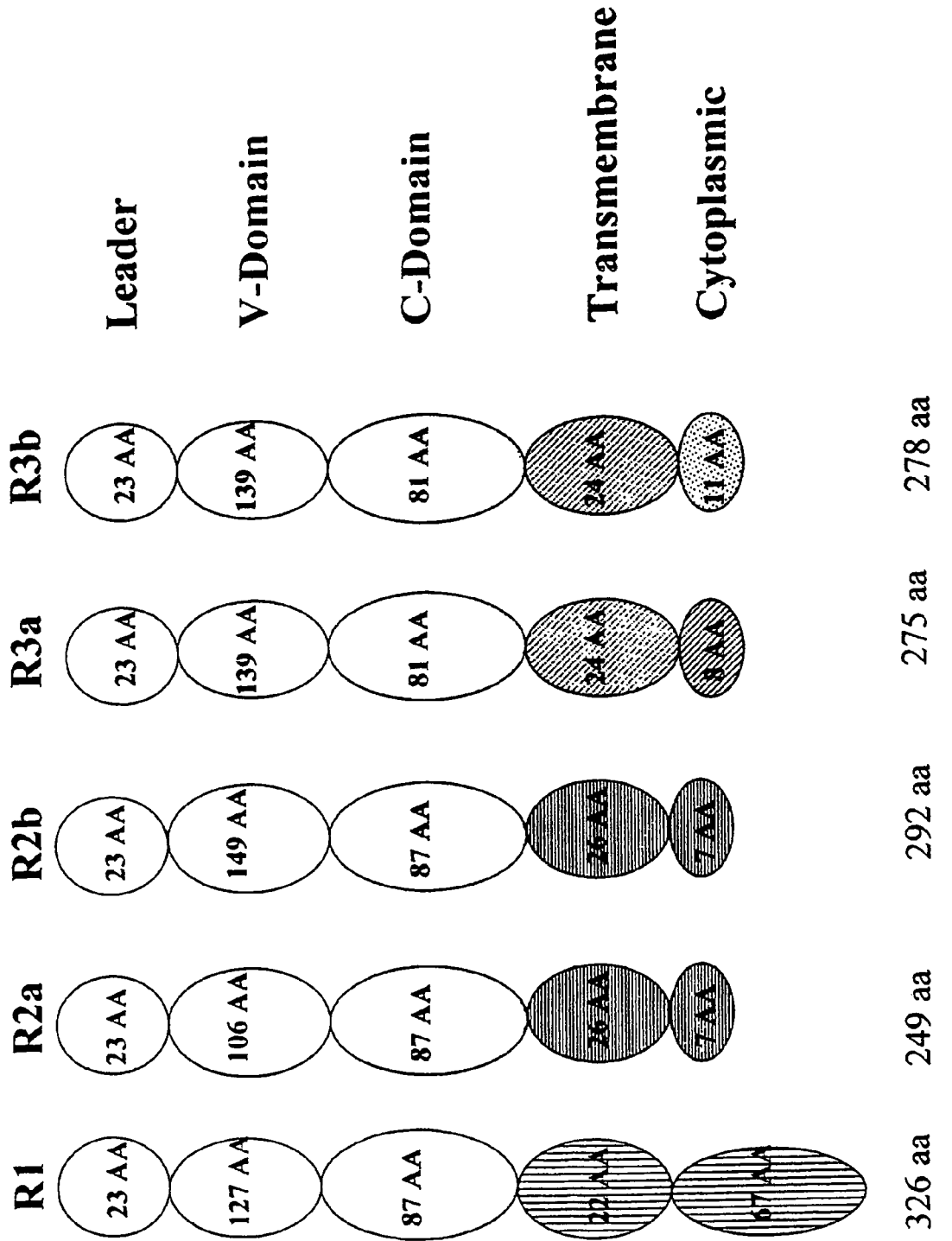
FIG. 7 is a schematic diagram showing the structure of some of the CD200 receptor isoforms.

As hereinbefore mentioned, the present inventors have sequenced several murine isoforms of the CD200 receptor (CD200R) termed CD200R2a, CD200R2b and CD200R3a. The inventors are the first to determine the full length sequence of CD200R2a and CD200R2b and the first to determine that there are two isoforms of the CD200R2 receptor. The inventors are also the first to identify and sequence a novel isoform of CD200R3, namely CD200R3a.

Accordingly, the present invention provides an isolated CD200R2a having a nucleic acid sequence encoding a protein having the amino acid sequence shown in FIG. 4 (SEQ ID NO:2), or a homolog or analog thereof. The present invention also provides an isolated CD200R2b having a nucleic acid sequence encoding a protein having the amino acid sequence shown in FIG. 5 (SEQ ID NO:4) or a homolog or analog thereof. In a further embodiment, the present invention provides an isolated CD200R3a having a nucleic acid sequence encoding a protein having the amino add sequence shown in FIG. 6 (SEQ ID NO:6) or a homolog or analog thereof.

The term "isolated" refers to a nucleic add substantially free of cellular material or culture medium when produced by recombinant DNA techniques or chemical precursors or other chemicals when chemically synthesized.

The term "nucleic add sequence" refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic add sequences of the present invention may be ribonucleic (RNA) or deoxyribonucleic adds (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thio-alkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

The term "homolog" as used herein includes sequences that are homologous to the sequences shown herein including the homologous sequence from other species including human and other mammals.

In a preferred embodiment, the CD200R2a nucleic acid sequence comprises:

(a) a nucleic add sequence as shown in FIG. 1 (SEQ ID NO:1), wherein T can also be U;

(b) a nucleic add sequence that is complimentary to a nucleic add sequence of (a);

(c) a nucleic add sequence that has substantial sequence homology to a nucleic add sequence of (a) or (b);

(d) a nucleic add sequence that is an analog of a nucleic acid sequence of (a), (b) or (c); or (e) a nucleic acid sequence that hybridizes to a nucleic acid sequence of (a), (b), (c) or (d) under stringent hybridization conditions.

In a preferred embodiment, the CD200R2b nucleic add sequence comprises:

(a) a nucleic acid sequence as shown in FIG. 2 (SEQ ID NO:3), wherein T can also be U;

(b) a nucleic acid sequence that is complimentary to a nucleic acid sequence of (a);

(c) a nucleic acid sequence that has substantial sequence homology to a nucleic add sequence of (a) or (b);

(d) a nucleic acid sequence that is an analog of a nucleic add sequence of (a), (b) or (c); or (e) a nucleic add sequence that hybridizes to a nucleic add sequence of (a), (b), (c) or (d) under stringent hybridization conditions.

In a preferred embodiment, the CD200R3a nucleic add sequence comprises:

(a) a nucleic acid sequence as shown in FIG. 3 (SEQ ID NO:5), wherein T can also be U;

(b) a nucleic acid sequence that is complimentary to a nucleic acid sequence of (a);

(c) a nucleic acid sequence that has substantial sequence homology to a nucleic acid sequence of (a) or (b);

(d) a nucleic acid sequence that is an analog of a nucleic add sequence of (a), (b) or (c); or (e) a nucleic acid sequence that hybridizes to a nucleic acid sequence of (a), (b), (c) or (d) under stringent hybridization conditions.

The term "sequence that has substantial sequence homology" means those nucleic add sequences which have slight or inconsequential sequence variations from the sequences in (a) or (b), i.e., the sequences function in substantially the same manner and/or are the homologous sequences from other species. The variations may be attributable to local mutations or structural modifications. Nucleic acid sequences having substantial homology include nucleic acid sequences having at least 65%, more preferably at least 85%, and most preferably 90-95% identity with the nucleic acid sequences as shown in FIG. 1, 2 or 3.

The term "sequence that hybridizes" means a nucleic acid sequence that can hybridize to a sequence of (a), (b), (c) or (d) under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The term "a nucleic acid sequence which is an analog" means a nucleic acid sequence which has been modified as compared to the sequence of (a), (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence shown in FIG. 1, 2 or 3 with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in FIG. 1, 2 or 3. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

The CD200R isoforms of the invention are likely differentially expressed in different tissues. They may also bind to ligands other than CD200.

The present invention also includes the CD200R proteins. Accordingly, in one embodiment, the present invention provides an isolated CD200R2a protein having an amino acid sequence shown in FIG. 4 (SEQ ID NO:2) or an analog, homolog or fragment thereof. In another embodiment, the present invention provides an isolated CD200R2b having an amino acid sequence shown in FIG. 5 (SEQ ID NO:4) or an analog, homolog or fragment thereof. In a further embodiment, the present invention provides an isolated CD200R3a protein having an amino add sequence shown in FIG. 6 (SEQ ID NO:6) or an analog, homolog or fragment thereof.

Within the context of the present invention, a protein of the invention may include various structural forms of the primary protein which retain biological activity. For example, a protein of the invention may be in the form of acidic or basic salts or in neutral form. In addition, individual amino acid residues may be modified by oxidation or reduction.

In addition to the full length amino acid sequence, the protein of the present invention may also include truncations of the protein, and analogs, and homologs of the protein and truncations thereof as described herein. Truncated proteins or fragments may comprise peptides of at least 5, preferably 10 and more preferably 15 amino acid residues of the sequence shown in FIG. 4, 5 or 6.

The invention further provides polypeptides comprising at least one functional domain or at least one antigenic determinant of a CD200R2a, CD200R2b or CD200R3a protein.

Analogs of the protein of the invention and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences of the invention. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence of the CD200R2a, CD200R2b or CD200R3a protein as described herein. Such homologs are proteins whose amino acid sequences are comprised of amino acid sequences that hybridize under stringent hybridization conditions (see discussion of stringent hybridization conditions herein) with a probe used to obtain a protein of the invention. Homologs of the protein include the protein from other species including humans. Homologs of a protein of the invention will have the same regions which are characteristic of the protein.

A homologous protein includes a protein with an amino acid sequence having at least 70%, preferably 80-95% identity with the amino acid sequence of the CD200R2a, CD200R2b or CD200R3a protein.

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein to produce fusion proteins. For example, the CD200R2a, CD200R2b or CD200R3a cDNA sequence is inserted into a vector that contains a nucleotide sequence encoding another peptide (e.g. GST-glutathione succinyl transferase). The fusion protein is expressed and recovered from prokaryotic (e.g. bacterial or baculovirus) or eukaryotic cells. The fusion protein can then be purified by affinity chromatography based upon the fusion vector sequence and the CD200R2a, CD200R2b or CD200R3a protein obtained by enzymatic cleavage of the fusion protein.

The proteins of the invention (including analogs, etc.) may be prepared using recombinant DNA methods. Accordingly, nucleic acid molecules of the present invention having a sequence which encodes a protein of the invention may be incorporated according to procedures known in the art into an appropriate expression vector which ensures good expression of the protein. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic add.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence of the invention. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, $\beta$-galactosidase, chloramphenicol acetyltransferase, or firefly luciferase. Transcription of the selectable marker gene is monitored by changes in the concentration of the selectable marker protein such as $\beta$-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. Accordingly, the invention includes a host cell comprising a recombinant expression vector of the invention. The term "transformed host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Suitable host cells include a wide variety of prokaryotic and eukaryotic host cells. For example, the proteins of the invention may be expressed in bacterial cells such as *E. coli, Pseudomonas, Bacillus subtillus*, insect cells (using baculovirus), yeast cells or mammalian cells. Other suitable host cells can be found in Goeddel, Gene Expression Technology: Methods in Enzymology 185, Academic Press, San Diego, Calif. (1991).

As an example, to produce CD200R2a, CD200R2b or CD200R3a proteins recombinantly, for example, *E. coli* can be used using the T7 RNA polymerase/promoter system using two plasmids or by labeling of plasmid-encoded proteins, or by expression by infection with M13 Phage mGPI-2. *E. coli* vectors can also be used with Phage lamba regulatory sequences, by fusion protein vectors (e.g. lacZ and trpE), by maltose-binding protein fusions, and by glutathione-S-transferase fusion proteins.

Alternatively, the CD200R2a, CD200R2b or CD200R3a protein can be expressed in insect cells using baculoviral vectors, or in mammalian cells using vaccinia virus. For expression in mammalian cells, the cDNA sequence may be ligated to heterologous promoters, such as the simian virus (SV40) promoter in the pSV2 vector and introduced into cells, such as COS cells to achieve transient or long-term expression. The stable integration of the chimeric gene construct may be maintained in mammalian cells by biochemical selection, such as neomycin and mycophoenolic acid.

The CD200R2a, CD200R2b or CD200R3a DNA sequence can be altered using procedures such as restriction enzyme digestion, fill-in with DNA polymerase, deletion by exonuclease, extension by terminal deoxynucleotide transferase, ligation of synthetic or cloned DNA sequences, site-directed sequence alteration with the use of specific oligonucleotides together with PCR.

The cDNA sequence or portions thereof, or a mini gene consisting of a cDNA with an intron and its own promoter, is introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. The endogenous CD200R2a or CD200R2b or CD200R3a gene promoter can also be used. Different promoters within vectors have different activities which alters the level of expression of the cDNA. In addition, certain promoters can also modulate function such as the glucocorticoid-responsive promoter from the mouse mammary tumor virus.

Some of the vectors listed contain selectable markers or neo bacterial genes that permit isolation of cells by chemical selection. Stable long-term vectors can be maintained in cells as episomal, freely replicating entities by using regulatory elements of viruses. Cell lines can also be produced which have integrated the vector into the genomic DNA. In this manner, the gene product is produced on a continuous basis.

Vectors are introduced into recipient cells by various methods including calcium phosphate, strontium phosphate, electroporation, lipofection, DEAE dextran, microinjection, or by protoplast fusion. Alternatively, the cDNA can be introduced by infection using viral vectors.

CD200R2a, CD200R2b or CD200R3a proteins may also be isolated from cells or tissues, including mammalian cells or tissues, in which the protein is normally expressed.

The protein may be purified by conventional purification methods known to those in the art, such as chromatography methods, high performance liquid chromatography methods or precipitation. For example, an anti-CD200R2a, anti-CD200R2b or CD200R3a antibody (as described below) may be used to isolate a CD200R2a, CD200R2b or CD200R3a protein, which is then purified by standard methods.

The proteins of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

II. Uses

The present invention includes all uses of the nucleic acid molecule and CD200R2a, CD200R2b or CD200R3a proteins of the invention including, but not limited to, the preparation of antibodies and antisense oligonucleotides, the preparation of peptide mimetics, the preparation of experimental systems to study these isoforms of CD200R, screening assays for the isolation of substances that modulate expression and/or activity of these isoforms of CD200R as well as the use of these isoforms of CD200R (nucleic acid sequences and proteins) and modulators thereof in diagnostic and therapeutic applications. Some of the uses are further described below.

(a) Antibodies

The isolation of the CD200R2a, CD200R2b or CD200R3a protein enables the preparation of antibodies specific for CD200R2a, CD200R2b or CD200R3a. Accordingly, the present invention provides an antibody that binds to a CD200R2a, CD200R2b and/or CD200R3a protein. Antibodies to the various isoforms of CD200R may be useful therapeutically as discussed in greater detail in Section III. Antibodies may be used advantageously to monitor the expression of CD200R2a, CD200R2b or CD200R3a or to detect a particular isoform. Antibodies can be prepared which bind a distinct epitope in an unconserved region of one of the isoforms which would allow one to distinguish between them and other isoforms of the CD200R. An unconserved region of the protein is one that does not have substantial sequence homology to other proteins.

The preparation of antibodies to the CD200Rs are described in Example 2. Other antibodies can be prepared using techniques known in the art. Conventional methods can be used to prepare the antibodies. For example, by using a peptide of CD200R2a, CD200R2b or CD200R3a polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for CD200R2a, CD200R2b or CD200R3a as described herein.

The term "antibody" as used herein is intended to include fragments thereof which also specifically bind with CD200R2a, CD200R2b or CD200R3a or peptide thereof. Antibodies can be fragmented using conventional techniques and the fragments screened for utility in the same manner as described above. For example, $F(ab')^2$ fragments can be generated by treating antibody with pepsin. The resulting $F(ab')_2$ fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of CD200R2a, CD200R2b or CD200R3a antigens of the invention (See, for example, Morrison et al., Proc. Natl. Acad. Sci. U.S.A. 81,6851 (1985); Takeda et al., Nature 314,452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against CD200R2a, CD200R2b or CD200R3a proteins may also be generated by screening expression libraries encoding immunoglobulin genes, or portions thereof, expressed in bacteria with peptides produced from the nucleic acid molecules of CD200R2a, CD200R2b or CD200R3a. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, can be used to produce antibodies or fragments thereof.

(b) Antisense Oligonucleotides

Isolation of a nucleic acid molecule encoding CD200R2a, CD200R2b or CD200R3a enables the production of antisense oligonucleotides that can modulate the expression and/or activity of CD200R2a, CD200R2b or CD200R3a.

Accordingly, the present invention provides an antisense oligonucleotide that is complimentary to a nucleic acid sequence encoding CD200R2a, CD200R2b or CD200R3a.

The term "antisense oligonucleotide" as used herein means a nucleotide sequence that is complimentary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The antisense oligonucleotides may be introduced into tissues or cells using techniques in the art including vectors (retroviral vectors, adenoviral vectors and DNA virus vectors) or physical techniques such as microinjection. The antisense oligonucleotides may be directly administered in vivo or may be used to transfect cells in vitro which are then administered in vivo. In one embodiment, the antisense oligonucleotide may be delivered to macrophages and/or endothelial cells in a liposome formulation.

(c) Peptide Mimetics

The present invention also includes peptide mimetics of the CD200 receptor proteins of the invention. Such peptides may include competitive inhibitors, enhancers, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino adds corresponding to a peptide of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides derived from the CD200 receptor isoforms may also be used to identify lead compounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds that can be tested for predicted properties as related to the target molecule. The activity of the lead compounds can be evaluated using assays similar to those described herein.

Information about structure-activity relationships may also be obtained from co-crystallization studies. In these studies, a peptide with a desired activity is crystallized in association with a target molecule, and the X-ray structure of the complex is determined. The structure can then be compared to the structure of the target molecule in its native state, and information from such a comparison may be used to design compounds expected to possess.

(d) Screening Assays

The present invention also includes screening assays for identifying agents that modulate CD200 receptors such as CD200R2a, CD200R2b and CD200R3a. Agents that modulate include agents that stimulate a CD200 receptor (i.e. CD200R agonists) and agents that inhibit a CD200 receptor (CD200R antagonists).

In accordance with one embodiment, the invention enables a method for screening candidate compounds for their ability to modulate the activity of a CD200 receptor. The method comprises providing an assay system for assaying the outcome of CD200 receptor signalling, assaying the signalling activity in the presence or absence of the candidate or test compound and determining whether the compound has increased or decreased CD200 receptor signalling.

Accordingly, the present invention provides a method for identifying a compound that modulates a CD200 receptor comprising:

(a) incubating a test compound with a CD200 receptor protein or a nucleic acid encoding a CD200 receptor protein; and (b) determining the effect of the compound on CD200 receptor protein activity or expression and comparing with a control (i.e. in the absence of the test substance), wherein a change in the CD200 receptor protein activity or expression as compared to the control indicates that the test compound modulates a CD200 receptor.

A change in CD200 receptor activity includes a change in signalling through the receptor or a change in function that is associated with signalling through the receptor in a cell.

For example, as described herein, stimulating a CD200 receptor can result in the release of cytokines that are associated with immune suppression. Therefore, one can measure cytokine levels to determine whether or not CD200 receptor activity is modulated by a test compound. An example of a cytokine assay is described in reference 103 which describes that stimulation of a CD200 receptor on macrophages stimulates the release of IL-6 and TNF-α.

In accordance with a further embodiment, test compounds can also be tested for their ability to increase or decrease expression of a CD200 receptor. The method comprises putting a cell with a candidate compound, wherein the cell expresses a CD200 receptor. In one embodiment, the present invention enables culture systems in which cell lines which express the CD200 receptor gene are incubated with candidate compounds to test their effects on CD200 receptor expression. Such culture systems can be used to identify compounds which upregulate or downregulate CD200 receptor expression or its function, through the interaction with other proteins. The cells used in the assay can either endogenously express a CD200 receptor or can be modified to recombinantly express a CD200 receptor.

After a period of incubation in the presence of a selected test compound(s), the expression of a CD200 receptor can be examined by quantifying the levels of CD200 receptor mRNA using standard Northern blotting procedure, as described in the examples included herein, to determine any changes in expression as a result of the test compound. Cell lines transfected with constructs expressing CD200 receptor can also be used to test the function of compounds developed to modify the protein expression.

(i) Agonists

In one embodiment, the screening assay can be used to identify CD200 receptor agonists. The term "CD200 receptor agonist" as used herein means any agent that can bind, crosslink or ligate a CD200 receptor and result in the stimulation of the receptor. Stimulating a CD200 receptor includes stimulating the signalling through the receptor or stimulating a function of a cell that is associated with signalling through the receptor. For example, the stimulation of the receptor by the agonist will result in a similar (or improved) suppression of an immune response as is seen when the natural ligand for the receptor, CD200, is administered.

Accordingly, the present invention provides a method of identifying a CD200R agonist comprising the steps of:
 (a) incubating a test substance with a CD200R; and
 (b) determining whether or not the test substance stimulates a CD200R, wherein stimulation of the CD200R indicates that the test compound is a CD200R agonist.

In one embodiment, the CD200R is selected from CD200R2a, CD200R2b or CD200R3a.

Determining whether or not a test compound stimulates a CD200R (and is useful as a CD200R agonist) can be assessed by observing the effects of the test substance on cells bearing the receptor as compared to a control in the absence of a test substance. As an example, the test substance can be assessed for its ability to suppress an immune response, to induce the production of immune inhibitory cytokines (type-2 cytokines) or to inhibit the production of immune stimulatory cytokines (type-1 cytokines). The ability of a test substance to inhibit an immune response can be tested in a variety of in vitro and in vivo assays including, but not limited to, inhibiting a mix lymphocyte reaction; inhibiting a cytotoxic T lymphocyte (CTL) response; inhibiting interleukin-2 production or inhibiting interferon-γ production. Cytokine and CTL assays are described in Example 2.

One can also test a CD200 agonist for its ability to treat or prevent a disease wherein it is desirable to suppress an immune response including, but not limited to, preventing transplant rejection, treating an autoimmune disease or preventing fetal loss. One skilled in the art can readily determine whether or not the CD200R agonist is useful in preventing or inhibiting transplant rejection. Many animal models can be used to assess transplantation including the rat islet xenograft model described in Example 6.

One skilled in the art can also readily determine whether or not a CD200R agonist would be useful in preventing autoimmune disease. In particular, several animal models are available including the model described in Example 7 wherein a collagen induced arthritis model is described. Further, many other autoimmune animal models are available, including, but not limited to, experimental allergic encephalomyelitis which is an animal model for multiple sclerosis, animal models of inflammatory bowel disease (induced by immunization, or developing in cytokine-knockout mice), and models of autoimmune myocarditis and inflammatory eye disease.

One of skill in the art can also determine whether or not a particular CD200 receptor agonist is useful in preventing fetal loss. For example, a potential CD200 receptor agonist can be tested for its ability to prevent fetal loss in an animal model. For example, one could use a murine model of cytokine induced abortion in abortion-prone CBA×DBA/2 or mice pre-immunized with anti-phospholipid may also be used.

(ii) Antagonists

In another embodiment, the screening assay can be used to identify CD200 receptor antagonists. The term "CD200 receptor antagonist" as used herein means any agent that can inhibit the activation or stimulation of a CD200 receptor. Inhibiting a CD200 receptor includes inhibiting signalling through the receptor and inhibiting a function of a cell that is associated with the receptor. For example, the inhibition of the receptor by the antagonist can block the binding of CD200 to the receptor and therefore inhibit the function of CD200. Accordingly, a CD200R antagonist will inhibit the immune suppression caused by CD200.

Accordingly, the present invention provides a screening assay for identifying an antagonist of a CD200 receptor comprising the steps of:
 (a) incubating a test substance with a CD200 receptor; and
 (b) determining whether or not the test substance inhibits the CD200 receptor.

One skilled in the art will appreciate that many methods can be used in order to determine whether or not a test substance can inhibit a CD200R. For example, one can test whether or not the potential antagonist interferes with the binding of CD200 and a CD200R. One can also test the antagonist to determine if it inhibits the suppression of the immune response caused by CD200. One of skill in the art can readily determine whether or not a potential antagonist is effective in inhibiting CD200. For example, the potential antagonist can be tested in in vitro assays to determine if the function or activity of CD200 is inhibited. The potential antagonist can also be tested for its ability to induce an immune response using in vitro immune assays including, but not limited to, enhancing a cytotoxic T cell response; inducing interleukin-2 (IL-2) production; inducing IFNγ production; inducing a Th1 cytokine profile; inhibiting IL-4 production; inhibiting TGFβ production; inhibiting IL-10 production; inhibiting a Th2 cytokine profile and any other assay that would be known to one of skill in the art to be useful in detecting immune activation.

Preventing immune suppression caused by CD200 can also be tested a wide range of conditions wherein it is desirable to prevent immune suppression or enhance an immune response including, but not limited to, bacterial and viral infections and cancer. In particular, a potential antagonist can be tested in an animal model to see if it can prevent or inhibit the proliferation or growth of a tumor cell. One of skill in the art can determine whether a potential antagonist is useful in inhibiting tumor cell growth. One can test the potential antagonist for its ability to induce an immune response using known in vitro assays. In addition, the potential antagonist can be tested in an animal model wherein the potential antagonist is administered to an animal with cancer.

In a further embodiment, the screening assay can be used to identify CD200 receptor ligands. Accordingly, the invention provides a method of identifying substances which bind with a CD200 receptor, comprising the steps of:

(a) reacting the CD200 receptor and a test substance, under conditions which allow for formation of a complex, and (b) assaying for complexes of the CD200 receptor and the test substance, for free substance, and for non-complexed CD200 receptor, wherein the presence of complexes indicates that the test substance is capable of binding the CD200 receptor. In a specific embodiment the CD200R is selected from CD200R2a, CD200R2b or CD200R3a.

In another embodiment, agonists and/or antagonists of the binding of CD200 to its receptor can be identified. Therefore the invention also contemplates a method for assaying for an agonist or antagonist of the binding of CD200 with its receptor or other CD200 ligands such as antibodies to CD200. The agonist or antagonist may be an endogenous physiological substance or it may be a natural or synthetic substance. Accordingly the invention provides a method for identifying an antagonist or agonist of CD200 binding comprising the steps of:

(a) reacting CD200, a known binding target, preferably an CD200 receptor, and a potential antagonist or agonist; and (b) determining the amount of CD200 bound to the binding target and comparing this with a control in the absence of the antagonist or agonist.

In all of the above screening assays, the test compound can be any compound which one wishes to test including, but not limited to, proteins, peptides, nucleic acids (including RNA, DNA, antisense oligonucleotide, peptide nucleic acids), carbohydrates, organic compounds, small molecules, natural products, library extracts, bodily fluids and other samples that one wishes to test for modulators of a CD200 receptor.

The CD200 receptor is generally immobilized in the above assays. Preferably, the CD200 receptor is expressed on the surface of a cell.

The screening methods of the invention include high-throughput screening applications. For example, a high-throughput screening assay may be used which comprises any of the methods according to the invention wherein aliquots of cells transfected with a CD200 receptor are exposed to a plurality of test compounds within different wells of a multi-well plate. Further, a high-throughput screening assay according to the invention involves aliquots of transfected cells which are exposed to a plurality of candidate factors in a miniaturized assay system of any kind. Another embodiment of a high-throughput screening assay could involve exposing a transfected cell population simultaneously to a plurality of test compounds.

The method of the invention may be "miniaturized" in an assay system through any acceptable method of miniaturization, including but not limited to multi-well plates, such as 24, 48, 96 or 384-wells per plate, micro-chips or slides. The assay may be reduced in size to be conducted on a micro-chip support, advantageously involving smaller amounts of reagent and other materials. Any miniaturization of the process which is conducive to high-throughput screening is within the scope of the invention.

The invention extends to any compounds or modulators of a CD200 receptor identified using the screening method of the invention. The term "modulator of a CD200 receptor" as used herein means a test compound or substance that can modulate the function or activity of a CD200 receptor including the CD200R2a, CD200R2b and CD200R3a isoforms described herein. The term includes both test compounds or substances that can activate or enhance the function or activity of a CD200 receptor as well as test compounds or substances that can inhibit or suppress the function or activity of a CD200 receptor. Such modulators include, but are not limited to, proteins, peptides, nucleic adds (including RNA, DNA, genes, antisense oligonucleotides, peptide nucleic adds), carbohydrates, organic compounds, small molecules and natural products.

The invention also includes a pharmaceutical composition comprising a modulator of a CD200 receptor identified using the screening method of the invention in admixture with a suitable diluent or carrier. The invention further includes a method of preparing a pharmaceutical composition for use in modulating an immune response comprising mixing a modulator of a CD200 receptor identified according to the screening assay of the invention with a suitable diluent or carrier.

The present invention also includes all business applications of the screening assay of the invention including conducting a drug discovery business. Accordingly, the present invention also provides a method of conducting a drug discovery business comprising:

(a) providing one or more assay systems for identifying a modulator of a CD200 receptor;

(b) conducting therapeutic profiling of modulators identified in step (a), or further analogs thereof, for efficacy and toxicity in animals; and (c) formulating a pharmaceutical preparation including one or more modulators identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

The present invention also provides a method of conducting a target discovery business comprising:

(a) providing one or more assay systems for identifying modulators of a CD200 receptor;

(b) (optionally) conducting therapeutic profiling of modulators identified in step (a) for efficacy and toxicity in animals; and (c) licensing, to a third party, the rights for further drug development and/or sales for modulators identified in step (a), or analogs thereof.

(e) Experimental Systems

Eukaryotic expression systems can be used for many studies of the CD200R2a, CD200R2b or CD200R3a gene and gene product(s) including determination of proper expression and post-translational modifications for full biological activity, identifying regulatory elements located in the 5' region of the CD200R2a, CD200R2b or CD200R3a gene and their role in tissue regulation of protein expression, production of large amounts of the normal and mutant protein for isolation and purification, to use cells expressing the CD200R2a, CD200R2b or CD200R3a protein as a functional assay system for antibodies generated against the protein or to test effectiveness of pharmacological agents.

Using the techniques mentioned, the expression vectors containing the CD200R2a, CD200R2b or CD200R3a cDNA sequence or portions thereof can be introduced into a variety of mammalian cells from other species or into non-mammalian cells.

The recombinant cloning vector, according to this invention, comprises the selected DNA of the DNA sequences of this invention for expression in a suitable host. The DNA is operatively linked in the vector to an expression control sequence in the recombinant DNA molecule so that CD200R protein can be expressed. The expression control sequence may be selected from the group consisting of sequences that control the expression of genes of prokaryotic or eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of SV40, promoters derived from polyoma, adenovirus, retrovirus, baculovirus, simian virus, 3-phosphoglycerate kinase promoter, yeast acid phosphatase promoters, yeast alpha-mating factors and combinations thereof.

Expression of the CD200R2a, CD200R2b or CD200R3a gene in heterologous cell systems may also be used to demonstrate structure-function relationships as well as to provide cell lines for the purposes of drug screening. CD200R2a, CD200R2b or CD200R3a DNA sequence into a plasmid expression vector to transfect cells is a useful method to test the proteins influence on various cellular biochemical parameters including the identification of substrates as well as activators and inhibitors of the phosphatase. Plasmid expression vectors containing either the entire coding sequence for CD200R2a, CD200R2b or CD200R3a or for portions thereof, can be used in in vitro mutagenesis experiments that will identify portions of the protein crucial for regulatory function.

The DNA sequence can be manipulated in studies to understand the expression of the gene and its product. The changes in the sequence may or may not alter the expression pattern in terms of relative quantities, tissue-specificity and functional properties.

(f) Diagnostic Assays

The isolation of CD200 receptor isoforms allows the detection of these molecules in cells and the diagnosis of conditions involving an increase or decrease in CD200R2a, CD200R2b or CD200R3a activity or expression of these isoforms.

Accordingly, the present invention provides a method of detecting a CD200R2a, CD200R2b or CD200R3a protein or nucleic acid in a sample (including an absence) comprising assaying the sample for (a) a nucleic acid molecule encoding a CD200R2a, CD200R2b or CD200R3a protein or a fragment thereof or (b) a CD200R2a, CD200R2b or CD200R3a protein or a fragment thereof.

(i) Nucleic Acid Molecules

The nucleic acid molecules encoding CD200R2a, CD200R2b or CD200R3a as described herein or fragments thereof, allow those skilled in the art to construct nucleotide probes for use in the detection of nucleotide sequences encoding CD200R2a, CD200R2b or CD200R3a or fragments thereof in samples, preferably biological samples such as cells, tissues and bodily fluids. The probes can be useful in detecting the presence of a condition associated with CD200R2a, CD200R2b or CD200R3a or monitoring the progress of such a condition. Accordingly, the present invention provides a method for detecting a nucleic acid molecules encoding CD200R2a, CD200R2b or CD200R3a comprising contacting the sample with a nucleotide probe capable of hybridizing with the nucleic acid molecule to form a hybridization product, under conditions which permit the formation of the hybridization product, and assaying for the hybridization product.

Example of probes that may be used in the above method include fragments of the nucleic acid sequences shown in FIG. 1, 2 or 3. A nucleotide probe may be labelled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labelled antibody, fluorescent compounds, enzymes, antibodies specific for a labelled antigen, and chemiluminescence. An appropriate label may be selected having regard to the rate of hybridization and binding of the probe to the nucleic acid to be detected and the amount of nucleic acid available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes, preferably in human cells, that hybridize to the nucleic acid molecule of the present invention preferably, nucleic acid molecules which hybridize to the nucleic acid molecule of the invention under stringent hybridization conditions as described herein.

Nucleic acid molecules encoding a CD200R2a, CD200R2b or CD200R3a protein can be selectively amplified in a sample using the polymerase chain reaction (PCR) methods and cDNA or genomic DNA. It is possible to design synthetic oligonucleotide primers from the nucleotide sequence shown in FIG. 1, 2 or 3 for use in PCR. A nucleic acid can be amplified from cDNA or genomic DNA using oligonucleotide primers and standard PCR amplification techniques. The amplified nucleic acid can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

(ii) Proteins

The CD200R2a, CD200R2b or CD200R3a protein may be detected in a sample using antibodies that bind to the protein as described in detail above. Accordingly, the present invention provides a method for detecting a CD200R2a, CD200R2b or CD200R3a protein comprising contacting the sample with an antibody that binds to CD200R2a, CD200R2b or CD200R3a which is capable of being detected after it becomes bound to the CD200R2a, CD200R2b or CD200R3a in the sample.

Antibodies specifically reactive with CD200R2a, CD200R2b or CD200R3a or derivatives thereof, such as enzyme conjugates or labeled derivatives, may be used to detect CD200R2a, CD200R2b or CD200R3a in various biological materials, for example they may be used in any known immunoassays which rely on the binding interaction between an antigenic determinant of CD200R2a, CD200R2b or CD200R3a and the antibodies. Examples of such assays are radioimmunoassays, enzyme immunoassays (e.g. ELISA), immunofluorescence, immunoprecipitation, latex agglutination, hemagglutination and histochemical tests. Thus, the antibodies may be used to detect and quantify CD200R2a, CD200R2b or CD200R3a in a sample in order to determine its role in particular cellular events or pathological states, and to diagnose and treat such pathological states.

In particular, the antibodies of the invention may be used in immuno-histochemical analyses, for example, at the cellular and sub-subcellular level, to detect CD200R2a, CD200R2b or CD200R3a to localise it to particular cells and tissues and to specific subcellular locations, and to quantitate the level of expression.

Cytochemical techniques known in the art for localizing antigens using light and electron microscopy may be used to detect CD200R2a, CD200R2b or CD200R3a. Generally, an antibody of the invention may be labelled with a detectable substance and CD200R2a, CD200R2b or CD200R3a may be localised in tissue based upon the presence of the detectable substance. Examples of detectable substances include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine I-125, I-131 or 3-H. Antibodies may also be coupled to electron dense substances, such as ferritin or colloidal gold, which are readily visualised by electron microscopy.

Indirect methods may also be employed in which the primary antigen-antibody reaction is amplified by the introduction of a second antibody, having specificity for the antibody reactive against CD200R2a, CD200R2b or CD200R3a. By way of example, if the antibody having specificity against CD200R2a, CD200R2b or CD200R3a is a rabbit IgG antibody, the second antibody may be goat anti-rabbit gamma-globulin labelled with a detectable substance as described herein.

Where a radioactive label is used as a detectable substance, CD200R2a, CD200R2b or CD200R3a may be localized by autoradiography. The results of autoradiography may be quantitated by determining the density of particles in the autoradiographs by various optical methods, or by counting the grains.

III. Therapeutic Methods (a) CD200 Receptors

As previously stated, the present inventors have demonstrated that the CD200 peptide is a potent immune modulator capable of suppressing an immune response as described in WO 99/24565, which is incorporated herein by reference in its entirety. In summary, the CD200 molecule is useful in modulating many immune responses as an immunosuppressant or in inducing immune tolerance, including but not limited to inducing tolerance to transplantations, preventing graft versus host disease, inhibiting fetal loss, treating autoimmune diseases, allergies and inflammatory conditions. As a result, it is expected that the CD200R molecules described herein may also be involved in immune modulation. Consequently, the present invention includes methods of modulating an immune response caused by CD200 using the isoforms of CD200R described herein.

Accordingly, the present invention provides a method of modulating an immune response comprising administering an effective amount of a CD200R2a, CD200R2b or CD200R3a to a cell or animal in need thereof. The present invention also includes a use of an effect amount of CD200R2a, CD200R2b or CD200R3a to modulate an immune response or for the manufacture of a medicament to modulate an immune response.

The term "modulate an immune response" as used herein refers to the suppression, including inducing immune tolerance, or activation of an immune response.

The term "effective amount" as used herein means an amount effective, at dosages and for periods of time necessary to achieve the desired results. Effective amounts of a molecule may vary according to factors such as the disease state, age, sex, weight of the animal. Dosage regima may be adjusted to provide the optimum therapeutic response. For example, several divided doses may be administered daily or the dose may be proportionally reduced as indicated by the exigencies of the therapeutic situation.

The term "animal" as used herein includes all members of the animal kingdom which express CD200, preferably humans.

The term "a cell" includes a single cell as well as a plurality or population of cells. Administering an agent to a cell includes both in vitro and in vivo administrations.

The immune responses that may be modulated include modulating graft rejection, fetal loss, autoimmunity, allergy, tumor rejection, skin disorders and all inflammatory diseases.

The CD200R molecules of the invention for use in the therapeutic methods may be prepared as a soluble fusion protein. The fusion protein may contain the extracellular domain of the CD200R molecule linked to an immunoglobulin (Ig) Fc Region. The CD200R molecule fusion may be prepared using techniques known in the art. Generally, a DNA sequence encoding the extracellular domain of CD200R molecule is linked to a DNA sequence encoding the Fc of the Ig and expressed in an appropriate expression system where the CD200R molecule—FcIg fusion protein is produced. The CD200R molecule peptide may be obtained as described herein, such as using recombinant DNA techniques. The CD200R molecule peptide may also be modified to contain amino add substitutions, insertions and/or deletions that do not alter the immunomodulation properties of the peptide. Conserved amino acid substitutions involve replacing one or more amino acids of the CD200R molecule amino acid sequence with amino acids of similar charge, size, and/or hydrophobicity characteristics. When only conserved substitutions are made the resulting analog should be functionally equivalent to the CD200R molecule peptide. Non-conserved substitutions involve replacing one or more amino acids of the CD200R molecule amino acid sequence with one or more amino adds which possess dissimilar charge, size, and/or hydrophobicity characteristics.

The CD200R molecule peptide may be modified to make it more therapeutically effective or suitable. For example, the CD200R molecule peptide may be cyclized as cyclization allows a peptide to assume a more favourable conformation. Cyclization of the CD200R molecule peptides may be achieved using techniques known in the art. In particular, disulphide bonds may be formed between two appropriately spaced components having free sulfhydryl groups. The bonds may be formed between side chains of amino acids, non-amino acid components or a combination of the two. In addition, the CD200R molecule peptide or peptides of the present invention may be converted into pharmaceutical salts by reacting with inorganic acids including hydrochloric acid, sulphuric acid, hydrobromic acid, phosphoric add, etc., or organic acids including formic add, acetic acid, propionic acid, glycolic add, lactic acid, pyruvic acid, oxalic add, succinic acid, malic acid, tartaric acid, citric add, benzoic acid, salicylic acid, benzenesulphonic acid, and tolunesulphonic acids.

(b) CD200 Receptor Modulators

The present invention also includes methods of modulating an immune response by modulating a CD200 receptor. The present inventors have demonstrated that administering whole antibodies that bind to and crosslink a CD200 receptor enhances the immune suppression caused by CD200. This is demonstrated in Examples 4 and 6 wherein prolongation of graft survival is seen following administration of whole antibodies to CD200R. This is further demonstrated in Example 7 wherein whole antibodies to CD200 receptor prevent autoimmune disease. Importantly, the inventors have demonstrated that they can ameliorate an established autoimmune disease, such as arthritis.

Accordingly, the present invention provides a method of modulating an immune response by administering an effective amount of an agent that modulates a CD200 receptor to a cell or animal in need thereof. The present invention also provides a use of an effective amount of an agent that modulates a CD200 receptor to modulate an immune response. The present invention further provides a use of an effective amount of an agent that modulates a CD200 receptor for the manufacture of a medicament to modulate an immune response.

The term "agent that modulates a CD200 receptor" includes any agent that can stimulate or activate the receptor (i.e. CD200 receptor agonists) as well as any agent that can inhibit or suppress the receptor (i.e. CD200 receptor antagonists).

(i) Immune Suppression

In one aspect, the present invention provides a method of suppressing an immune response comprising administering an effective amount of a CD200 receptor agonist to a cell or animal in need thereof. The present invention also includes a use of a CD200 receptor agonist to suppress an immune response. The present invention further includes a use of a CD200 receptor agonist for the manufacture of a medicament to suppress an immune response.

Any CD200R agonist that is useful in suppressing an immune response can be used including antibodies, peptide mimetics, small molecules, CD200 proteins and fragments thereof, soluble CD200, soluble CD200Rs and modulators identified according to the screening assays described herein. In one embodiment, the CD200R agonist is an antibody that crosslinks a CD200 receptor such as a whole anti-CD200 receptor immunoglobulin. In a specific embodiment, the antibody binds to a CD200R1 or CD200R3 receptor.

Suppression of an immune response with a CD200R agonist has utility in a wide range of therapeutic applications including any condition wherein one would want to suppress an immune response such as transplantation, autoimmune disease, fetal loss, allergy, cancer, skin disorders and all inflammatory diseases including Crohn's disease, colitis and irritable bowel syndrome.

The present inventors have shown that administering an antibody against a CD200R is useful in preventing transplant rejection. Accordingly, in one embodiment, the present invention provides a method of suppressing an immune response to a transplanted organ or tissue in a recipient animal comprising administering an effective amount of a CD200R agonist to a recipient animal. The invention also includes a use of a CD200R agonist to prevent transplant rejection or for the manufacture of a medicament to prevent transplant rejection. The CD200R agonist may be co-administered with other immune suppressants including, but not limited to, CD200, preferably a soluble form of CD200 such as CD200:Fc, anti-inflammatory agents and immune suppressive cytokines.

The recipient can be any member of the animal kingdom including rodents, pigs, cats, dogs, ruminants, non-human primates and preferably humans. The organ or tissue to be transplanted can be from the same species as the recipient (allograft) or can be from another species (xenograft). The tissues or organs can be any tissue or organ including heart, liver, kidney, lung, pancreas, pancreatic islets, brain tissue, cornea, bone, intestine, skin and heamatopoietic cells.

The method of the invention may be also used to prevent graft versus host disease wherein the immune cells in the transplant mount an immune attack on the recipient's immune system. This can occur when the tissue to be transplanted contains immune cells such as when bone marrow or lymphoid tissue is transplanted when treating leukemias, aplastic anemias and enzyme or immune deficiencies, for example.

Accordingly, in another embodiment, the present invention provides a method of preventing or inhibiting graft versus host disease in a recipient animal receiving an organ or tissue transplant comprising administering an effective amount of a CD200R agonist to the organ or tissue prior to the transplantation in the recipient animal. The invention includes a use of an effective amount of a CD200R to prevent or inhibit graft versus host disease or for the manufacture of a medicament to prevent or inhibit graft versus host disease.

As mentioned previously, the inventors have demonstrated that administering antibodies to a CD200R can ameliorate an autoimmune disease such as diabetes and arthritis. Accordingly, in another embodiment, the present invention provides a method of preventing or treating an autoimmune disease comprising administering an effective amount of a CD200R agonist to an animal in need thereof. The invention also includes a use of a CD200R agonist to prevent autoimmune disease or for the manufacture of a medicament to prevent autoimmune disease.

The autoimmune disease may be any autoimmune disease including, but not limited to, arthritis, type 1 insulin-dependent diabetes mellitus, adult respiratory distress syndrome, inflammatory bowel disease, dermatitis, meningitis, thrombotic thrombocytopenic purpura, Sjögren's syndrome, encephalitis, uveitis, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernidous anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, tissue specific autoimmunity, degenerative autoimmunity delayed hypersensitivities, autoimmune complications of AIDS, atrophic gastritis, ankylosing spondylitis and Addison's disease.

In one embodiment, the autoimmune disease is arthritis. Accordingly, the present invention provides a method of preventing or treating arthritis comprising administering an effective amount of a CD200R agonist to a cell or animal in need thereof. The present invention also includes a use of a CD200R agonist to prevent or treat arthritis or for the manufacture of a medicament to prevent or treat arthritis.

In another embodiment, the autoimmune disease is diabetes. Accordingly, the present invention provides a method of preventing or treating diabetes comprising administering an effective amount of a CD200R agonist to a cell or animal in need thereof. The present invention also includes a use of a CD200R agonist to prevent or treat diabetes or for the manufacture of a medicament to prevent or treat diabetes.

In a further embodiment, the present invention provides a method of preventing or treating an allergy comprising administering an effective amount of a CD200R agonist to an animal having or suspected of having an allergy. The invention includes a use of an effective amount of a CD200R agonist to prevent or treat an allergy or for the manufacture of a medicament to prevent or treat an allergy.

Allergies that may be prevented or treated using the methods of the invention include, but are not limited to, hay fever, asthma, atopic eczema as well as allergies to poison oak and ivy, house dust mites, bee pollen, nuts, shellfish, penicillin and numerous others.

It has previously been shown that there is an association between levels of CD200 expression and fertility. In particular it has been shown that low levels (or no levels) of CD200 is related to fetal loss. Further, administering a CD200:Fc fusion protein prevented fetal loss (WO 99/24565 published May 20, 1999, which is incorporated herein by reference). Accordingly, CD200R agonists may be useful in modulating fertility.

Accordingly, the present invention provides a method of preventing, reducing or inhibiting fetal loss comprising administering an effective amount of a CD200R agonist to an animal in need thereof. The invention includes a use of an effective amount of a CD200R agonist to prevent or inhibit fetal loss or for the manufacture of a medicament to prevent or inhibit fetal loss.

(ii) Inhibiting Immune Suppression

The inventors have demonstrated in Examples 4, 5 and 7 that administering an antibody fragment to a CD200 receptor, such as an F(ab')$_2$ anti-CD200R, blocks the engagement of CD200 with its receptor and inhibits the activity of CD200.

Accordingly, in other aspect the present invention provides a method of inhibiting immune suppression comprising administering an effective amount of CD200 receptor antagonist. The present invention also includes a use of a CD200R antagonist to inhibit immune suppression or for the manufacture of a medicament to inhibit immune suppression.

The CD200R antagonist can be any agent that can block the activation or stimulation of a CD200R such as an antibody fragment, small molecule, peptide mimetic, peptide or an antisense oligonucleotide to a CD200 receptor. In one embodiment, the antagonist is an antibody fragment that binds to the CD200 receptor but does not activate or crosslink the receptor. In a specific embodiment, the antibody fragment is an F(ab')$_2$ or Fab fragment.

There are many conditions wherein one might want to prevent immune suppression including the prevention and treatment of infections (including viral, bacterial and fungal infections) and cancer as well as inducing fetal loss.

It was demonstrated that inhibiting CD200 inhibits tumor growth (WO 02/11762, published Feb. 14, 2002, which is incorporated herein by reference). Therefore, inhibiting a CD200R may also be useful in inhibiting or preventing tumor cell growth. The present invention provides a method of inhibiting, preventing or reducing tumor cell growth comprising administering an effective amount of a CD200R antagonist to a cell or an animal in need thereof. Preferably, the animal is an animal with cancer, more preferably human. The invention also provides a use of an effective amount of a CD200R antagonist to prevent or reduce tumor cell growth or for the manufacture of a medicament to prevent or reduce tumor cell growth.

The term "inhibiting or reducing tumor cell growth" means that the CD200R antagonist causes an inhibition or reduction in the growth or metastasis of a tumor as compared to the growth observed in the absence of the antagonist. The CD200R antagonist may also be used prophylactically to prevent the growth of tumor cells.

The tumor cell can be any type of cancer including, but not limited to, hematopoietic cell cancers (including leukemias and lymphomas), colon cancer, lung cancer, kidney cancer, pancreas cancer, endometrial cancer, thyroid cancer, oral cancer, laryngeal cancer, hepatocellular cancer, bile duct cancer, squamous cell carcinoma, prostate cancer, breast cancer, cervical cancer, colorectal cancer, melanomas and any other tumors which are antigenic or weakly antigenic. This could include, for example, EBV-induced neoplasms, and neoplasms occurring in immunosuppressed pateints, e.g. transplant patients, AIDS patients, etc.

VI. Induction of Suppressor Cells

The inventors have demonstrated in Example 8 that culturing bone marrow cells in the presence of monoclonal antibodies to CD200R led to the generation of suppressive dendritic cells (DCs). These suppressive DCs induce the development of antigen-specific suppressor T cells. Further, when infused in vivo, the suppressive DCs produce decreased rejection of an allograft.

Accordingly, the present invention provides a method of preparing suppressive antigen presenting cells comprising culturing a starting cell population in the presence of an effective amount of an agent that crosslinks or stimulates a CD200 receptor.

The starting population can be any population of cells that contains antigen presenting cells or precursors thereof. In one embodiment, the starting cell population contains bone marrow cells. The antigen presenting cells are preferably dendritic cells. The agent that stimulates or crosslinks the CD200 receptor is preferably an antibody.

The present invention also includes a method of preparing suppressive T cells comprising culturing a cell population containing T cells or precursors thereof in the presence of suppressive antigen presenting cells prepared according to the above method.

The invention further includes a method of suppressing an immune response comprising administering an effective amount of a population of suppressive antigen presenting cells or suppressive T cells prepared according to the above methods, to a cell or animal in need thereof.

V. Pharmaceutical Compositions

The present invention includes pharmaceutical compositions containing the CD200R molecules and modulators of a CD200R of the invention. In one embodiment, the present invention includes a pharmaceutical composition comprising one or more of CD200R2a, CD200R2b or CD200R3a in admixture with a suitable diluent or carrier.

The present invention also includes pharmaceutical compositions comprising a CD200R agonist or CD200 antagonist of the invention. Accordingly, in one embodiment, the present invention provides a pharmaceutical composition for use in suppressing an immune response comprising an effective amount of a CD200R agonist in admixture with a suitable diluent or carrier. The compositions comprising CD200R agonists can include other immune suppressants including, but not limited to, CD200, preferably soluble forms of CD200 such as CD200:Fc, cytokines with immune suppressive activity, and anti-inflammatory agents.

In another embodiment, the present invention provides a pharmaceutical composition for use in preventing immune suppression comprising an effective amount of a CD200R antagonist in admixture with a suitable diluent or carrier. The compositions comprising CD200R antagonists can also include other agents including immune stimulants, cytokines with immune stimulatory activity and anti-cancer agents.

The present invention also includes pharmaceutical compositions containing antibodies that bind to CD200 receptors, including the novel CD200R molecules of the invention. Accordingly, the present invention provides a pharmaceutical composition comprising an antibody that binds to a CD200 receptor in admixture with a suitable diluent or carrier. In one embodiment, the pharmaceutical composition is for enhancing immune suppression and comprises an antibody that activates or crosslinks a CD200 receptor. In another embodiment, the composition is for preventing immune suppression caused by CD200 and comprises an antibody that inhibits the interaction of CD200 with its receptor but does not cause activation of the receptor.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions. The CD200 receptor or ligand is preferably injected in a saline solution either intravenously, intraperitoneally or subcutaneously.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other immune modulatory agents.

A pharmaceutical composition comprising the nucleic acid molecules of the invention may be used in gene therapy to modulate the immune response. Recombinant molecules comprising a nucleic acid sequence encoding a CD200R molecule of the invention, or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The nucleic acid molecules of the invention may also be applied extracellularly such as by direct injection into cells. The nucleic acid molecules encoding a CD200R molecule are preferably prepared as a fusion with a nucleic acid molecule encoding an immunoglobulin (Ig) Fc region. As such, the CD200R molecule will be expressed in vivo as a soluble fusion protein.

The following non-limiting examples are illustrative of the present invention:

EXAMPLES

Example 1

Isolation of Novel CD200 Receptors

The present inventors have isolated and sequenced several isoforms of the murine CD200 receptor which are designated CD200R2a, CD200R2b or CD200R3a herein. The cDNA sequences of the receptors were determined and are provided in FIGS. 1-3 (SEQ ID Nos:1, 3 and 5). The amino acid sequence of each is shown in FIGS. 4-6 (SEQ ID Nos: 2, 4 and 6).

Methods

Complementary DNA clone isolation and 5'-RACE. Using the BLASTn algorithm the inventors searched murine EST public databases using full length cDNA sequences for murine CD200R (Genbank accession number AF231393), hereafter referred to as CD200R1, using the BLASTn algorithm. For 5'-rapid amplification of cDNA ends total cellular RNA (1 µg) derived from murine brain, heart and spleen was reverse transcribed with a gene-specific anti-sense primers using SuperScript II reverse transcriptase (Life Technologies), as described (140). RNase H was used to remove template RNA. First round PCR was performed for each tissue by combining a generic sense primer with a CD200R2 gene-specific anti-sense primer 5'-TCA GGA ATG TGG TCA GGT GTG GA-3' (SEQ ID NO:7) or the CD200R3 gene-specific anti-sense primer 5'-CTC CCT GTG GCA CTT GCT CCT GAC-3' (SEQ ID NO:8). A second round of amplification was performed using a nested generic sense primer and a CD200R2 gene-specific anti-sense primer 5'-TGG TCT CCT TTG TTT CTA CTT TG-3' (SEQ ID NO:9) or a CD200R3 gene-specific anti-sense primer 5'-CTT GCA ATT GCC TCA CAA ACT AC-3' (SEQ ID NO:10). PCR products were subcloned into pCR11 (Invitrogen) and subjected to DNA sequence analysis with an ABI PRISM 377 automated DNA sequencer (Applied Biosystems, Perkin-Elmer Cetus) as described (141).

Genomic characterization. Bacterial artificial chromosome clones for CD200R2 and R3 were isolated from the RPCI-22 library. This library was generated using female murine 129S6/SvEvTac strain diploid genomic DNA that had been treated with EcoRI methylase, partially digested with EcoRI and subcloned into the EcoRI site of the vector pBACe3.6 (average clone insert size 155 kb) (Roswell Park Cancer Institute, Buffalo, N.Y.) (142). Complementary DNA (cDNA) probes represented murine CD200R1 (980 bp open reading frame), CD200R2 (Genbank Est AA516706, 470 bp EcoRI/KpnI fragment) and CD200R3 (Genbank Est AA545986, 450 bp BspHI/EcoRI fragment). Gel-purified cDNA probes were labeled to a specific activity of >$10^9$ cpm/mg with [$\alpha$-$^{32}$P]dCTP by the random primer labeling method as described. Six overlapping BAC clones were mapped with BamHI, HindIII, EcoRI, NotI, and SalI on a CHEF m DR mapping system (Bio-Rad). Southern blots were hybridized with [$\gamma$-$^{32}$P]ATP-labeled primers specific for CD200R1, CD200R2 and CD200R3. High molecular weight BAC DNA was digested with various restriction enzymes and subcloned into the multiple cloning site of pBluescript SK (−), and subjected to DNA sequence analysis. All exonic sequences and exon-intron boundaries were determined on both strands of genomic DNA.

Reverse transcription PCR (RT-PCR). First strand cDNA was synthesized using random primers and SuperScript II reverse transcriptase (Life Technologies) with total cellular RNA (5 µg) derived from varied normal murine tissues (Clontech): heart, brain, spleen, lung, liver, skeletal muscle, kidney, testis, thymus, small intestine, bone marrow) as described (142). Multiple independent isolations of RNA were utilized. For CD200R2 PCR amplifications were performed using the R2RT-PCR-S sense primer (5'-GGA GAC CAA TGA AAC CTG CTT-3') (SEQ ID NO:11) and the R2RT-PCR-AS antisense primer (5'-AAT AAT CCC CAA AAG GAC CAT-3') (SEQ ID NO:12) under well-characterized semi-quantitative conditions in a total volume of 100 µl for 25-30 cycles (annealing temperature 55.8° C., 487 bp amplicon). For CD200R3 PCR amplifications were performed using the R3RT-PCR-S sense primer (5'-CAT CTG GGA CAT TTA GAG AAG-3') (SEQ ID NO:13) and the R3RT-PCR-AS antisense primer (5'-TTG AAG TCC AAA GGA ATA AGA-3') (SEQ ID NO:14) under well-characterized semi-quantitative conditions in a total volume of 100 µl for 25-30 cycles (annealing temperature 53.4° C., 483 bp amplicon). Murine GAPDH was amplified to normalize for first-strand cDNA efficiency but did not affect results. PCR products were hybridized with [$\gamma$-$^{32}$P]ATP-labeled oligonucleotides positioned internally to flanking PCR primers and Southerns analyzed using a Phosphoimager with ImageQuant software (Molecular Dynamics). Experiments were performed on at least three independent occasions. Northern blot analysis. Multiple tissue northern blots representing 2 µg of size-fractionated oligo-dT purified RNA from varied normal murine tissues (heart, brain, spleen, lung, liver, skeletal muscle, kidney, testis) was hybridized according to the manufacturer's directions using published methods (143). Complementary DNA (cDNA) probes represented murine CD200R1 (981 bp open reading frame), CD200R2 (750 bp open reading frame for R2a) and CD200R3 (837 bp open reading frame for R3b). Gel-purified cDNA probes were labeled to a specific activity of ≧$10^9$ cpm/µg with [$\alpha$-$^{32}$P]dCTP by the random primer labeling method as described. Hybridization was carried out with 106 cpm/ml for 1 hr. Membranes were washed under high stringency conditions and radioactive signals recorded using a Molecular Dynamics PhosphorImager (Sunnyvale, Calif.) and quantitated using ImageQuant software 4.2 for Windows NT (Molecular Dynamics).

Results

The inventors determined that unique members of the murine CD200R family exist by performing low stringency searches of the public murine EST databases. Their analyses identified sequences that were highly related to, but not identical with, murine CD200R sequences reported by others (Genbank accession number AF231393) and hereafter referred to as CD200R1. Sequence analyses were performed on a variety of CD200R1-like clones, (i) full sequencing of plasmid cDNA clones corresponding to CD200R1-like EST sequences, (ii) clones generated from 5'-RACE using RNA isolated from a variety of murine tissues, and (iii) subclones of genomic BAC sequences. Two highly related CD200R cDNAs and genes were identified and named CD200R2 and CD200R3. Importantly, analyses of cDNA plasmid clones derived from EST and 5'-RACE strategies revealed additional RNA diversity.

CD200R2 exhibited 5'-mRNA diversity that altered the amino-terminus of the open reading frame. Characterization and analysis of the CD200R2a and CD200R2b mRNA transcripts indicated open reading frames of 750 nt and 879 nt which predicted a proteins of 249 and 292 amino acids with a calculated molecular weights of 27376 and 31932 daltons, respectively. CD200R2a and CD200R2b shared 228 amino acids at the carboxy-terminus but differed by 21 and 64 amino acids at the amino-terminus, respectively. Characterization of murine BAC genomic clones indicated that alternate promoter usage and alternative splicing accounted for the structural 5'-mRNA diversity.

In contrast, CD200R3 exhibited 3'-mRNA diversity that altered the carboxy-terminus of the open reading frame. Characterization and analysis of the CD200R3a and CD200R3b mRNA transcripts indicated open reading frames of 828 nt and 837 nt which predicted a proteins of 275 and 278 amino acids with a calculated molecular weights of 31140 and 31310 daltons, respectively. CD200R3a and CD200R3b shared 273 amino acids at the amino-terminus but differed by 2 and 5 amino acids at the carboxy-terminus, respectively. Characterization of murine BAC genomic clones indicated that alternate 3'-terminal exon usage and alternative splicing accounted for the structural 3'-mRNA diversity.

The inventors examined the tissue-specific expression of CD200 receptors CD200R1, R2 and R3 using RT-PCR and Northern blot analysis. A semi-quantitative RT-PCR approach for all three isoforms utilized sense and antisense primers that spanned exon/intron boundaries. Robust expression of CD200R1 was observed in RNA isolated from thymus, intestine and brain. In contrast, minimal expression was evident in bone marrow or heart. Expression of CD200R2 mRNA was strongly detected in testes, kidney, bone marrow and spleen. Expression was negligible in skeletal muscle and brain. Expression of CD200R3 mRNA was strongly detected in testes, lung, bone marrow and spleen. Expression was negligible in skeletal muscle and intestine. Findings on Northern blots were consistent with results from 5'-RACE and RT-PCR.

Example 2

Antibodies to CD200R Isoforms

Following the genomic identification and mapping of a number of putative CD200R genes, the inventors have produced heterologous (rabbit) and rat mAbs to the different isoforms following synthesis of peptides conforming to unique sequences in the CD200Rs, and immunizing animals with KLH-peptides. In addition, the inventors defined unique tissue and cell distribution patterns for the CD200R isoforms by Northern and Southern blotting, and using the anti-CD200Rs, by Western gels and FACS analysis following expression of cDNAs encoding the different CD200Rs in COS cells. Finally the inventors have begun preliminary studies to characterize functional heterogeneity in the CD200R isoforms, by examining the effect of anti-CD200Rs on alloimmune responses (induction of CTL/cytokines) generated in vitro.

Materials and Methods

Animals:

8-week old C3H/HeJ and C57BL/6 mice ($H2^{k/k}$ and $H2^{b/b}$ respectively) were obtained from the Jackson Laboratories, Bar Harbour, Me., and kept 5/cage with food and water ad libitum. Mice were entered into experiments at 9 weeks of age.

Evidence for Binding of CD200Fc to CD200R Isoforms

In order to assess whether the various CD200R isoforms described could all serve as counter-ligands for CD200, an immunoadhesin (CD200Fc) incorporating the extracellular domain of CD200 linked to a murine IgG2a Fc region as described (51) was used. CD200Fc was coupled to FITC and the inventors then examined by FACS analysis binding of FITC-labeled CD200Fc to COS cells transiently transfected with pBK vectors encoding cDNAs for the various CD200R isoforms. As control the inventors examined binding to COS cells transduced with empty pBK vectors. COS cells expressing the different CD200R isoforms all bound FITC-CD200Fc.

Anti-CD200R Antibodies and CD200Fc Immunoadhesin:

Based on the predicted amino acid sequence of the CD200R isoforms, the following peptides were synthesized, coupled to Keyhole Limpet Hemocyanin, and used to immunize rabbits (American Peptide Company, Sunnyvale, Calif.) or rats (Immuno-Precise Antibodies, Victoria, BC) for ultimate production of heterologous or rat mAbs to mouse CD200R, essentially as described in a previous report (103) and human CD200R1.

```
                              (SEQ ID NO:15)
Murine CD200R1    STPDHSPELQISAVTLQHEGTYTC (SEQ ID NO:16)
Murine CD200R2a   CEAMAGKPAAQISWTPDGD (SEQ ID NO:17)
Murine CD200R2b   KPRGQPSCIMAYKVETKET (SEQ ID NO:18)
Murine CD200R3a   CSVKGREEIIPPDDSFPFSDDN (SEQ ID NO:19)
Murine CD200R3b   LQQISKKICTERGTYRVPAHHQSS (SEQ ID NO:20)
Human CD200R1     CTKAYKKETNETKETNCTDER
```

Rabbit and rat heterologous and mAbs were pre-screened in ELISA using plates coated with the relevant peptides (100 ng/ml). The specificity of all sera and mAbs was assessed by FACS staining, using COS cells transiently transfected with an "empty" pBK vector, or a vector containing a cDNA insert for the respective CD200Rs, followed by FITC-anti-rabbit Ig (or anti-rat Ig). Both FITC-conjugated antibodies were purchased from Cedarlane Laboratories, Hornby, Ontario. Control cells were stained with FITC antibodies only.

Antigen Stimulation In Vitro and Cytokine Assays:

Spleen cell suspensions were prepared aseptically in α-MEM supplemented with 10% Fetal Calf Serum and $1 \times 10^{-6}$M 2-mercaptoethanol (αF10) from pools of three C3H (responder) or C57BL/6 (stimulator) mice. Stimulator cells were treated at a concentration of $1 \times 10^7$ cells/ml for 45 minutes at 37° C. with mitomycin C. Thereafter cells were cultured in triplicate in microtitre plates ($1 \times 10^6$ cells/well of each responder and stimulator) in 300 µl of αF10 in the presence/absence of various concentrations of anti-CD200R. In some cultures C3H spleen cells were stimulated only with anti-CD200Rs.

Culture supernatants (150 µl) were harvested at 40 hrs of culture and assessed for IL-2, IL-4, IL-6, IL-10 TNFα and IFNγ levels using an ELISA assay and commercial cytokine-specific mAbs obtained from Pharmingen (San Diego, Calif.). Plates precoated with 100 ng/ml R4-6A2 and developed with biotinylated XMG1.2 were used to assay IFNγ; those precoated with S4B6 (ATCC) and developed with biotinylated JES6-5H4, to measure IL-2; 11B11 (ATCC) and biotinylated BVD6-24G2 to measure IL-4; MP5-20F3 and biotinylated MP5-32C11 to measure IL-6; JES5-2A5 with biotinylated SXC-1 to measure IL-10; and those precoated with G281-2626 and developed with biotinylated MP6-XT3 were used to assay TNFα. In all cases streptavidin-coupled alkaline phosphatase with appropriate substrate was used to develop the assay, and recombinant mouse cytokines (Endogen, San Diego, Calif.) were used to quantitate the assay.

In addition to analyzing cytokines, induction of CTL in stimulated cells was assessed at 5 days in $^{51}$Cr-release assays, using labeled EL4 tumor target cells. All assays were performed in triplicate, with cultures containing unstimulated responder cells only serving as an appropriate control.

Results

Figure 8:
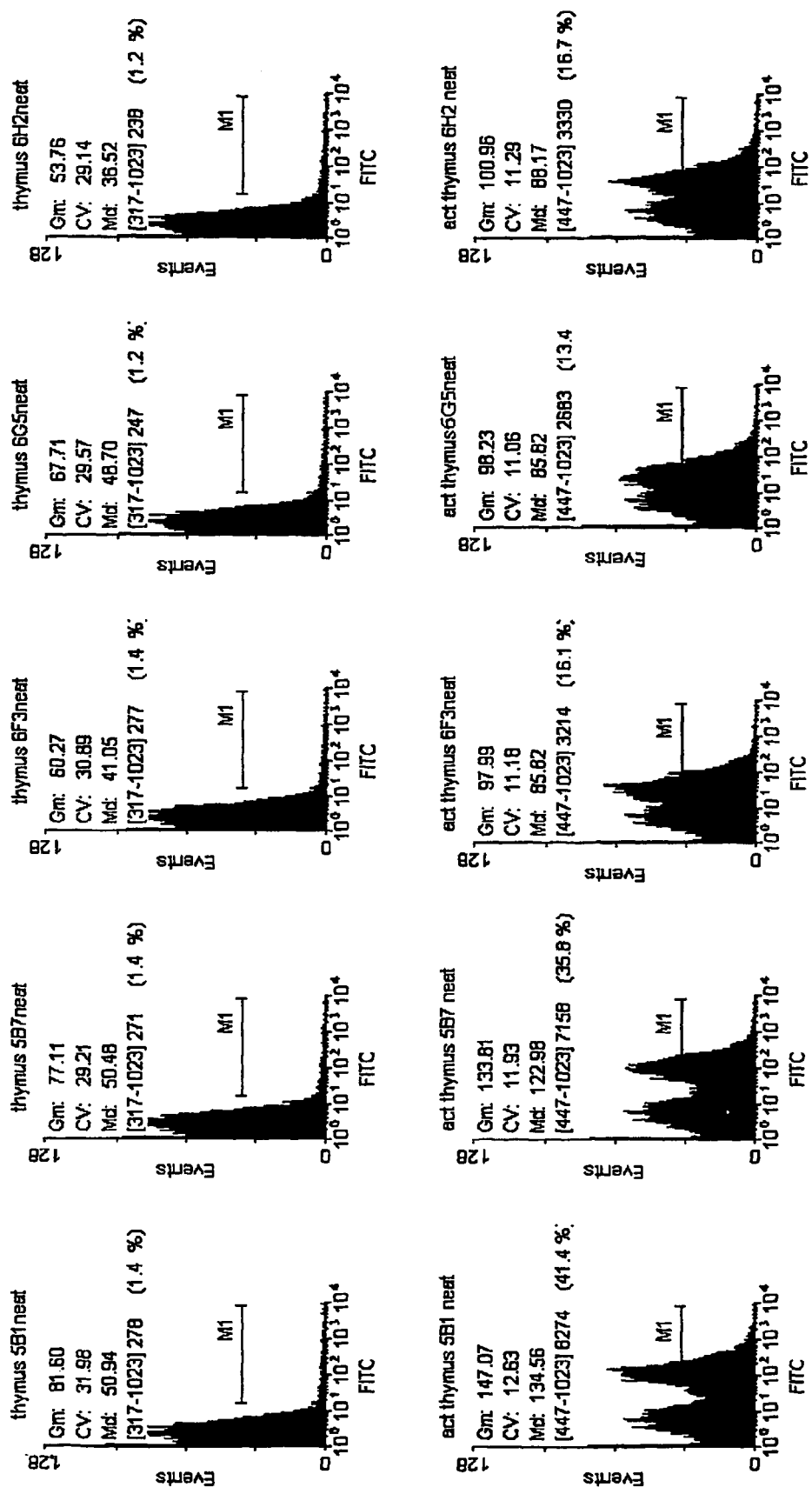
FIG. 8 shows FACS profile for 5 independent anti-CD200R1 mAbs with resting vs activated (Con A) thymocytes (all mAb tested using non-diluted supernatants).

Binding of CD200Fc to Different CD200R Isoforms, and Tissue Staining with anti-CD200Rs FACS analysis using control COS cells and COS cells transiently transfected to express the various CD200R isoforms with FITC-CD200Fc confirmed that all the CD200R isoforms served as binding receptors for CD200. Antibodies to the receptors have been prepared which are summarized in Table 8. In particular, Table 8 shows mean FACS staining of different tissues while Table 9 shows a functional screen (e.g. cytokine production). Data summarized in Table 8 indicate that the various anti-CD200Rs, each of which detected unique expression epitopes for the CD200R isoforms expressed following transient transfection of the relevant cDNAs in COS cells, show different staining patterns on cells isolated from different tissues. Typical data for 5 independent anti-CD200R1 mAbs staining thymocytes are shown in FIG. 8.

Dual FACS Staining with CD200R on Cells from Different Tissues

Single cell suspensions prepared from spleen, thymus, bone marrow or peripheral blood were dual-stained in FACS using either heterologous (rabbit) or mAbs (rat) to the different CD200R-derived peptides described in the Materials and Methods, and PE-labeled commercial mAbs to different cell subsets (see Materials and Methods). In general a minimum of 5 independently derived mAbs specific for each isoform, as well as the heterologous rabbit serum, showed equivalent patterns of staining to that shown in FIG. 8.

Induction of Cytokines in Spleen Cells Following Incubation with Anti-CD200Rs

In a previous report the inventors described production of TNFα and IL-6 following incubation of mouse spleen cells with a rat anti-CD200R in vitro (103). In order to assess the ability of antibodies to different CD200R isoforms to induce this cytokine production the inventors incubated spleen cells in vitro with rabbit antisera (50 μg/ml) to peptides prepared from the different CD200Rs, or with mAbs to the same peptides. Supernatants were tested at 40 hrs in ELISA for the different cytokines. Data in Table 10 represent a summary from a minimum of 5 monoclonal antibodies and the rabbit sera for each peptide specificity shown.

Figure 9:
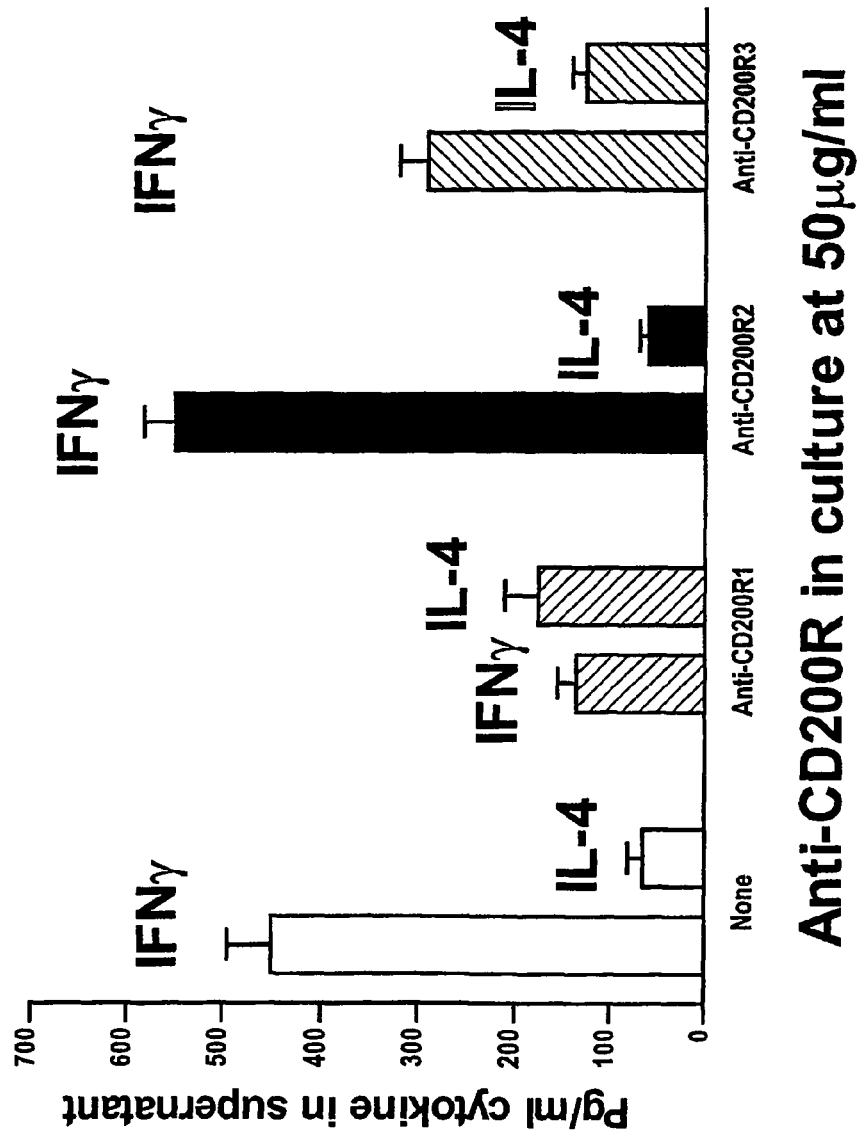
FIG. 9 is a graph showing inhibition of cytokine generation in spleen cell MLC cultures using antibodies to different CD200R isoforms. Data are shown for cultures using C3H responder cells and C57BL/6 stimulator cells, with supernatants assayed for cytokine levels by ELISA at 48 hrs. Results are pooled from a mean (±SD) of 3 independent assays for 2 each of the rabbit/rat heteroantibodies, and a minimum of 5 mAbs of each specificity.
Figure 10:
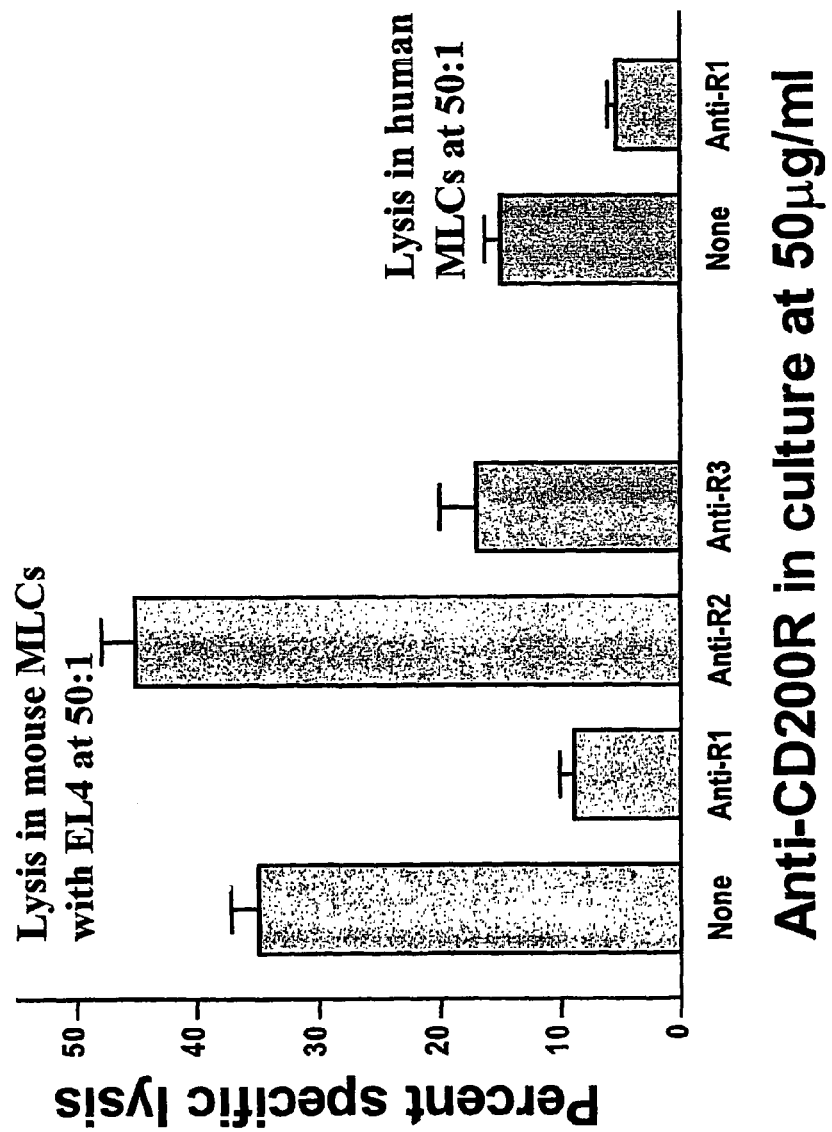
FIG. 10 is a graph showing inhibition of generation of CTL in spleen cell MLC cultures using antibodies to different CD200R isoforms. Data are shown for splenic MLCs using C3H responder cells and C57BL/6 stimulator cells, assayed at day 5 in $^{51}$Cr release assays with EL4 target cells (lysis at 50:1 effector:target ratio shown). Results are pooled from a mean (±SD) of 3 independent assays for 2 each of the rabbit/rat heteroantibodies, and a minimum of 5 mAbs of each specificity.

Altered CTL and Cytokine Production Following Addition of Different anti-CD200Rs to MLCs In a final study, the ability of the various antisera and mAbs described above to modify induction of CTL/cytokines in allostimulated MLCs in vitro was examined. C3H cells were stimulated with C57BL/6 spleen stimulator cells in the presence/absence of the anti-CD200Rs, and effector assays for cytokine production (ELISA) or CTL ($^{51}$Cr release with labeled EL4 tumor target cells) performed as described in the Materials and Methods. Summary data are shown in FIGS. 9 and 10. In FIG. 10 are also representative data showing the suppression of human MLC with anti-human CD200R1. The results suggest that optimal immune suppression is mediated by antibodies to CD200R1 or CD200R3. Antibodies to CD200R2 may have no suppressive capacity and may, in certain conditions, produce immune stimulation.

Example 3

CD200R and its Role in Immune Suppression

Materials and Methods

Mice: Male C3H/HeJ, BALB/c, C57Bl/6 and B10.Sgn, B10.BR and B10.D2 mice were purchased from the Jackson Laboratories, Bar Harbour, Me. Mice were housed 5/cage and allowed food and water ad libitum. All mice were used at 8-12 weeks of age.

Monoclonal antibodies: The following monoclonal antibodies (mAbs) were obtained from Pharmingen (San Diego, Calif., USA) unless stated otherwise: anti-IL-2 (S4B6, ATCC; biotinylated); anti-IL-4 (11B11, ATCC; biotinylated); anti-IFNγ (R4-6A2, ATCC; biotinylated XMG1.2); anti-IL-10 (JES5-2A5; biotinylated, SXC-1). PE anti-CD80, PE anti-F4/80, FITC anti-αβTCR, FITC anti-γδTCR, L3T4 (anti-mouse CD4), anti-thy1.2 and anti-Ly2.2 were obtained from Cedarlane Labs, Hornby, Ontario. The hybridoma producing DEC205 (anti-mouse dendritic cells) was a kind gift from Dr. R. Steinman, and was directly labeled with FITC. F(ab')2 rabbit anti-rat IgG PE conjugate (non-cross reactive with mouse IgG) was obtained from Serotec, Canada. PE rat anti-mouse CD200 (3B6) was obtained from BioSpark Inc., Mississauga, Ontario, Canada (19).

Strepavidin horse radish peroxidase and recombinant mouse GM-CSF was purchased from Pharmingen (San Diego, Calif.).

Preparation of cells: Single cell spleen and peripheral lymph node (PLN) suspensions were prepared aseptically from individual mice in each experiment. After centrifugation cells were resuspended in α-Minimal Essential Medium supplemented with 2-mercaptoethanol and 10% fetal calf serum (αF10). Peyer's Patch (PP) cells were used as a source of lymphocytes from which populations enriched for γδTCR$_+$ cells were obtained by adherence for 90 minutes at 37° C. to anti-γδTCR antibody coated plates (20).

Fresh splenic DC were obtained as the non-adherent component of overnight culture of plastic adherent spleen cells, while splenic macrophages represented the persistently adherent pool (21). In addition, bone marrow derived DC were prepared in vitro as described elsewhere (22). Bone marrow cells were pooled from 10 donors, treated with the mixture of antibodies (L3T4, anti-thy1.2, anti-Ly2.2) and rabbit complement, and cultured in 10 ml αF10 in tissue culture flasks, at a concentration of 2×10$^6$/ml with 500 U/ml recombinant murine GM-CSF (Pharmingen, USA). Fresh GM-CSF was added at 36 hour intervals. Cells were separated over lymphopaque on days 3.5 and 7 of culture, again reculturing in αF10 with recombinant GM-CSF. An aliquot of the sample stained at 10 days with FITC conjugated DEC205 mAb showed a mean staining in the order of 91%±8%. Remaining cells were washed, counted and used as described below.

Skin and Renal Transplantation:

These procedures were performed essentially as described elsewhere (3, 23). For renal transplantation, all recipients received an injection with cefotetan (30 mg/Kg) on the day of transplantation and for 2 succeeding days. All animals received im cyclosporin A (15 mg/Kg) daily for the first 3 days post transplantation. The remaining host kidney was removed 2 days after transplantation, unless otherwise indicated. Additional treatment of recipients was as described in individual studies.

Cytotoxicity and Cytokine Assays:

In cultures used to assess induction of cytotoxicity or cytokine production C3H responder cells were stimulated with equal numbers of mitomycin-C treated (100 μg/ml, for 45 minutes at 37° C.) spleen stimulator cells in triplicate in αF10. Supernatants were pooled at 40 hr from replicate wells and assayed in triplicate in ELISA assays for lymphokine production as described in detail elsewhere (4), using cytokine capture antibodies and enzyme-coupled developing antibodies as indicated above. Recombinant cytokines for standardization of assays was purchased from Genzyme (Cambridge, Mass.). Each assay reliably quantified cytokine levels in the range 40 to 4000 pg/ml.

When cytotoxicity was measured cells were harvested at 5 days and pooled from replicate wells, counted, and cultured at various effector:target ratios with $^{51}$Cr-labeled 72 hour spleen ConA blasts as target cells. Supernatants were sampled at 4 hours for assessment of specific cytotoxicity.

Production and Expression of an CD200:Fc Fusion Protein in a Baculovirus Expression System(1):

An immunoadhesin constructed to contain the extracellular domain of CD200, linked to a murine IgG2aFc region, was made as described elsewhere, and expressed using a Baculovirus Expression Vector System (BEVS) in *Spodoptera frugiperda* (Sf) insect cells. This fusion protein inhibits type-1 cytokine production from T cell stimulated with allogeneic DC in vitro (1). One mg of CD200:Fc was FITC-labeled using conventional techniques.

Cell Separation by Biophysical Means:

Velocity sedimentation, a technique separating cells into populations of different size, was performed as described elsewhere (24). In some experiments small (slow-sedimenting) cells were further fractionated, following labeling with PE-anti-F4/80 monoclonal antibody, using an anti-PE column. Recovery of F4/80$^+$, F4/80$^-$ cells was 75% and 90% respectively (see individual experiments below).

Statistical Analysis:

For comparison of DC FACS staining, or cytokine production in different groups assayed in vitro, initial ANOVAs were performed, followed by pair wise comparison of relevant groups using a Student t-test (see Legends to Figures/Tables).

Results

Figure 11:
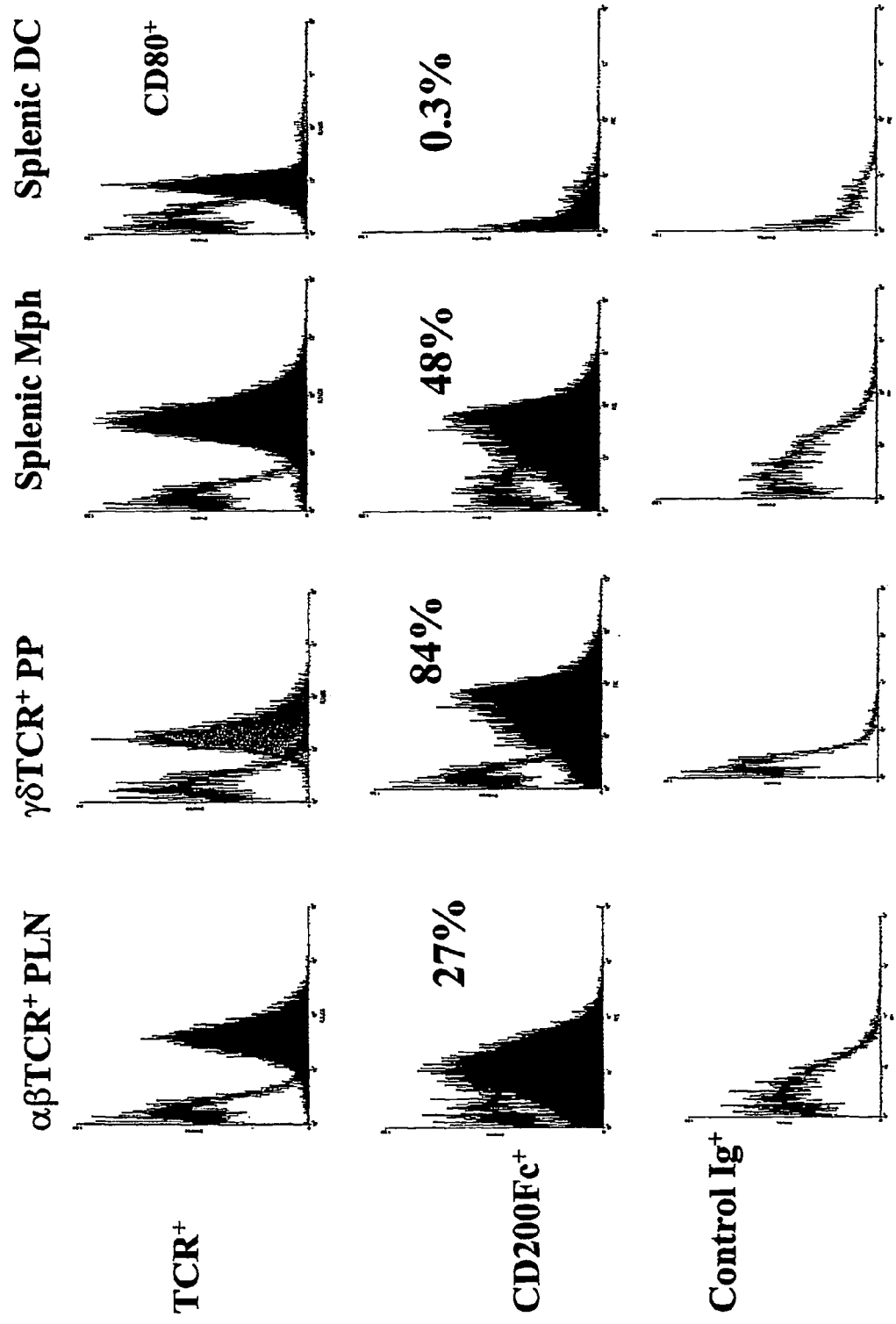
FIG. 11 is a FACS analysis of 24 hour LPS-stimulated fresh splenic macrophages and DC, or 72 hour Con A activated PLN and PP. Cells were preincubated for 30 min at 4° C. in PBS with 1% mouse serum before staining with the mAbs shown. Control cells were incubated with a FITC-coupled mouse MOPC15 myeloma Ig. Data in the upper panels show staining with FITC-anti-TCR (anti-αβTCR for PLN, anti-γδTCR for PP) or with PE-anti-CD80 (splenic macrophages and DC).

Binding of FITC-CD200:Fc to LPS Stimulated Splenic Cells, but not DC, and to $\alpha\beta/\gamma\delta TCR_+$ Cells:

24 hour LPS stimulated fresh splenic macrophages and DC were obtained from a pool of 3 C57BL/6 mice, while 72 hour ConA activated PLN and PP were similarly prepared from a pool of 3 other C57BL/6 donors. Cells were harvested, washed, preincubated for 30 minutes at 4° C. in PBS with 1% mouse serum, and thereafter stained with various different fluorescent mAbs, as shown in FIG. 11. As a control, cells were incubated independently also with a FITC-coupled mouse MOPC15 myeloma Ig. Data in FIG. 11 show the FACS profiles from one of 4 such studies using these different cell populations. In the upper panels cells are shown stained with FITC-anti-TCR (anti-$\alpha\beta$TCR for PLN, anti-$\gamma\delta$TCR for PP) or with PE-anti-CD80 (splenic macrophages and DC).

It is clear that subpopulations of activated $\alpha\beta$TCR+ cells and splenic macrophages bound the FITC-CD200:Fc, while no significant staining was seen with LPS activated splenic DC. >80% of activated PP $\gamma\delta$TCR± cells stained with FITC-CD200:Fc. When similar studies were performed using resting cells (no LPS or ConA activation), or in the presence of a 5 fold excess of unlabeled CD200:Fc, no binding of FITC-CD200:Fc above control was seen for any cell population (data not shown). In the work that follows the inventors have concentrated on characterization of the population of splenic cells binding FITC-CD200:Fc. (CD200R$^+$ cells)

Figure 12:
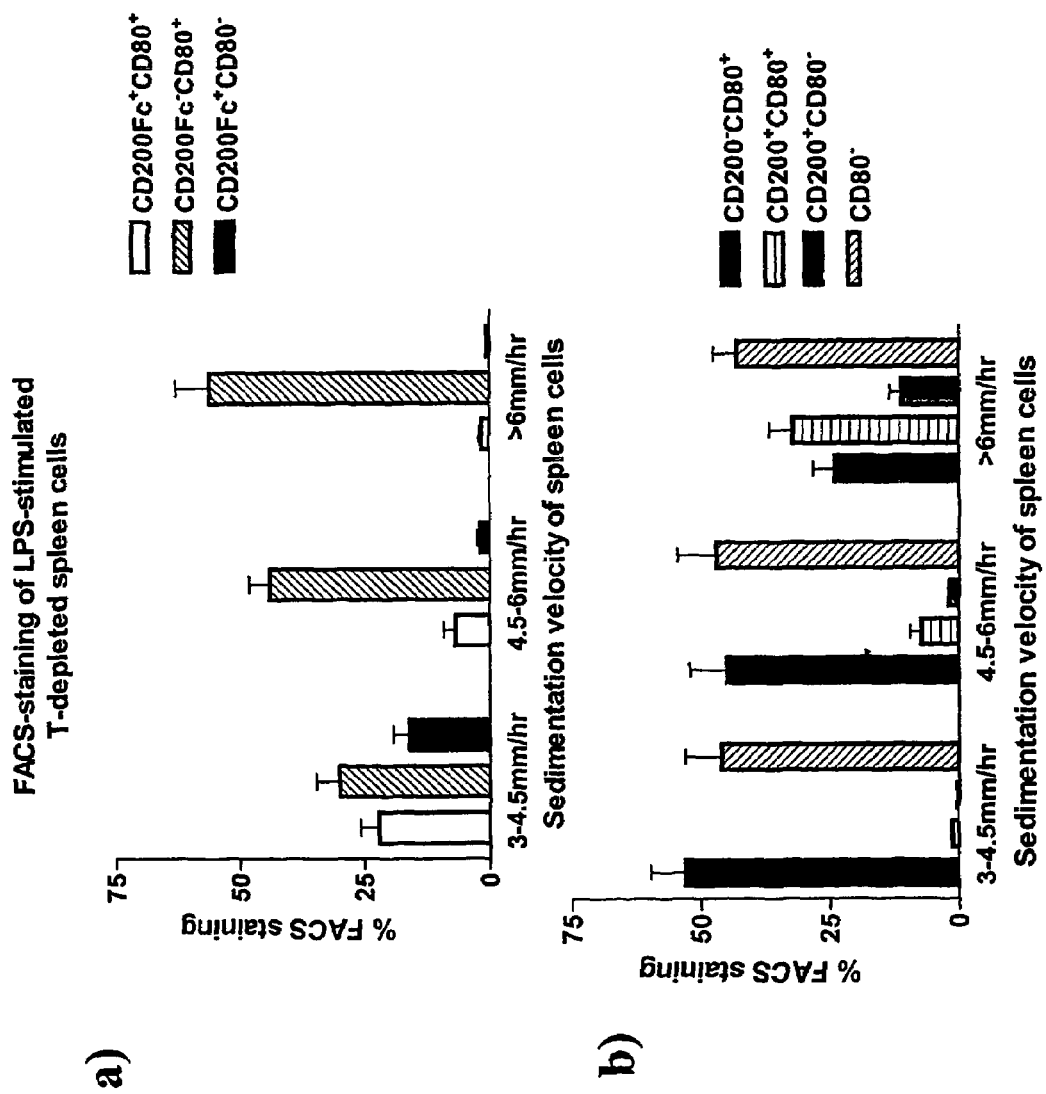
FIG. 12 is a bar graph showing characterization of CD200$^+$ and CD200:Fc binding cells (CD200R$^+$) in 48 hour LPS-stimulated, T-depleted, spleen cells after fractionation of the cells by size using unit gravity sedimentation techniques (24). The different cell populations shown were incubated with FITC-CD200:Fc, PE (or FITC) anti-CD200, and PE-anti-CD80, again after first preincubation with mouse serum (see FIG. 11). No cells were detected which bound both FITC-CD200:Fc and PE-anti-CD200 (data not shown).

Splenic Cells Binding FITC-CD200:Fc are Physically Distinguishable from CD200$_+$ Cells:

It was intriguing to us that a DC enriched cell population did not bind FITC-CD200:Fc (FIG. 11), while splenic macrophages did, since earlier data had suggested the existence of an immunoregulatory CD200$^+$ DC which could modulate stimulation induced by CD200– DC (7). Accordingly, the inventors next assessed whether CD200$^+$ and CD200:Fc binding cells could be further characterized. 48 hour LPS stimulated, T-depleted, spleen cells were subjected to frac- tionation by size using unit gravity sedimentation techniques (24), and different cell populations were incubated with FITC-CD200:Fc, PE (or FITC) anti-CD200, and PE-anti-CD80, again after first preincubation with mouse serum (see above). Data shown in FIG. 12 indicate FITC-CD200:Fc+ CD80+ cells, FITC-CD200:Fc– CD80$^+$ cells, FITC-CD200: Fc+CD80–, CD200$^+$CD80$^+$, CD200$^+$CD80– and CD200– CD80$^+$ cells. No cells were detected which bound both FITC-CD200:Fc and PE-anti-CD200 (data not shown).

It is clear from these data that CD80+ and CD80– FITC-CD200:Fc binding cells exist, and that these are found predominantly in a slow-sedimenting splenic population which contains some 50% of this splenic pool. In addition, both CD80$^+$ and CD80$^-$ CD200$^+$ cells exist, but in contrast to the CD200:Fc binding cells these are found in the faster-sedimenting cell population, making up <10% of this splenic pool.

Stimulation of CD200:Fc Binding Cells with CD200:Fc delays graft rejection in vivo, and Inhibits Alloreactivity In Vitro:

Since membrane bound CD200 itself lacks any significant signaling domains in the intracellular region (25), it was speculated that immunoregulation occurred following engagement of CD200R on the receptor bearing cell (1, 4, 25). In order to investigate whether immunoregulation induced in the presence of CD200:Fc was indeed enhanced by the presence of CD200R$^+$ cells, the following study was performed.

Slow-sedimenting spleen cells (capable of binding FITC-CD200:Fc-see FIG. 12) and fast-sedimenting (CD200$^+$) cells were obtained as described above from a pool of LPS-stimulated T-depleted spleen cells from 6 C57BL/6 mice. A control population of cells (intermediate sedimentation velocity: <3% CD200$^+$; <4% binding of FITC-CD200:Fc) was harvested also. Groups of 7 C3H mice received C57BL/6 skin grafts, along with cells from these different spleen pools, with or without infusion of CD200:Fc (10 µg/mouse; two doses only at 48 hour intervals). Skin graft survival was followed daily (see FIG. 13).

In a separate study C3H spleen cells were cultured with mitomycin-c treated C57BL/6 DC, again in the presence/absence of pools of the same splenic cells, with/without additional CD200:Fc protein. CTL (day 5) and cytokines (in the culture supernatant at 40 hours) were measured in standard fashion. Data from 1 of 3 such studies are shown in Table 1.

Infusion of CD200:Fc alone led to increased skin allograft survival. Only the CD200$^+$ large cell pool (sedimenting at >6 mm/hour) produced any prolongation of survival following infusion of the pools of splenic cells tested alone (see FIG. 13). However, infusion of CD200:Fc, in association with cells capable of binding FITC-CD200:Fc (CD200R+), the small cells (slow sedimenting pool), led to the most pronounced increased survival seen. These data were recapitulated by in vitro studies. Addition of CD200:Fc alone to the culture medium inhibited production of CTL and type-1 cytokines (IL-2, IFN$\gamma$). When used alone, the fast-sedimenting population of cells (CD200+) caused some inhibition in the assays measured. However, this was only modestly augmented by further addition of soluble CD200:Fc (percent change from group with no CD200:Fc, 58% for CTL, p<0.05; 46% for cytokines, p>0.05). In contrast, cells from the slow-sedimenting spleen pool (which bind FITC-CD200:Fc) produced little inhibition of CTL/cytokine activity by themselves, but caused profound inhibition in both assays in the presence of additional CD200:Fc (see Table 1: percent change from group with no CD200:Fc was 93% for CTL, p<0.01; 88% for cytokines, p<0.01).

Suppressive Activity in Splenic Cells Binding FITC-CD200: Fc Resides in F4/80+ Cells:

In an earlier study, the inventors had found that following pv immunization, adoptive transfer of inhibition of alloresponses was possible using an F4/80$^+$ cell population (20). Similarly, in a model of "immune deviation" following antigen inoculation to the anterior chamber of the eye, inhibition was adoptively transferred by F4/80$^+$ cells (26). The inventors speculated that the inhibition seen using the pool of slow-sedimenting CD200R$^+$cells described above might be associated with this F4/80$^+$ cell population. Accordingly, T-depleted, LPS stimulated spleen cells were fractionated as above, and following separation into small (CD200R$^+$: 3-4.5 mm/hour sedimentation velocity) or large (CD200$^+$: >6 mm/hour sedimentation velocity) cells, the inventors performed further fractionation of the small cell pool into F4/80$^+$, F4/80$^-$ cells, after first labeling this population with PE anti-F4/80 antibody (~10% cells stained). Medium size cells showed ~18% staining with F4/80 with negligible (<4%) staining of large cells with F4/80 antibody-data not shown. All cell populations were then tested as in Table 1 for their ability to inhibit the response of C3H responder cells stimulated with C57BL/6 stimulator cells, in the presence or absence of additional CD200:Fc. Data for one of two such studies are shown in Table 2.

As already shown in Table 1, inhibition from large (CD20$^+$) cells is independent of exogenous addition of CD200:Fc. In contrast, no inhibition was seen using small cells until CD200:Fc was added, when this population (containing CD200R$^+$cells) was the optimally inhibitory pool. More important, the F4/80$^+$ in this CD200R+small cell population was the most active for suppression in the context of exogenous CD200:Fc, with little such activity present in the small cell, F4/80$^-$. population.

Suppression by CD200R$^+$ Cells Follows Direct Allorecognition of MHC Incompatible APC In vitro, slow-sedimenting cells from LPS-stimulated C57BL/6 T-depleted spleen cultures (CD200L$^+$), can be used, following engagement of CD200:Fc, to inhibit the response of C3H responder cells stimulated to recognize C57BL/6 alloantigen. In order to assess whether the inhibition reflects a suppressive function following engagement by CD200:Fc by CD200R$^+$ cells which leads these cells to inhibit bystander immune responses (e.g. to third-party antigens) the inventors performed the following study. Inhibition of B10.BR anti-B10, B10 anti-B10.BR, or third-party B10.BR anti-B10.D2 alloresponses, were assessed using culture systems analogous to those shown in Table 1, where the inhibitory population (of CD200R$^+$ cells) used was the slow-sedimenting pool obtained from T-depleted, LPS stimulated, B10.Sgn spleen cells. Data for 1 of 2 such studies are shown in Table 3.

It is clear from these data that while exogenous CD200:Fc inhibits CTL and cytokine production in all the allorecognition combinations used, addition of slow-sedimenting B10 (CD200R$^+$) cells increased this inhibition only when responder T cells simultaneously recognized the same (B10) cells. Bystander inhibition of a third-party (B10.BR anti-B10.D2) response by CD200R$^+$ cells did not occur, nor indeed was inhibition seen when CD200R$^+$ cells were MHC compatible with the responder cell pool (B10 anti-B10.BR combination). Thus it seems the inhibitory signal delivered by CD200R$^+$ cells follows from their direct recognition, by responder T cells, in this case by MHC directed TCRs on responder cells.

Suppression by CD200R+ T cells in the presence of CD200: Fc of CTL and type-1 Cytokine Production Thymic Con A Blast (Con A activated αβTCR+) cells and Peyer's Patch (αδTCR+ cells) capable of binding FITC-CD200:Fc were obtained as described above.

As can be seen from Table 4, addition of CD200:Fc alone to the culture medium inhibited production of CTL and type-1 cytokines (IL-2, IFNγ). When used alone, the T-cells produced little inhibition of CTL/cytokine activity by themselves, but caused inhibition in both assays in the presence of additional CD200:Fc (see Table 4) This inhibition was most profound with γδTCR+ cells.

Data show that a functional ligand is indeed expressed on activated T cells (blasts). CD200R$^+$ T cells, preferably γδ-TCR+ cells, are stimulated in the presence of CD200:Fc to inhibit Cytotoxic T Lymphocytes (CTL) and type-1 cytokine production in vitro. CTL activity is expressed as a % specific lysis (of target cells).

Although, the most effective population for inhibition appears to be γδ-TCR+ cells, the thymic data (mostly αβ-TCR+ cells) suggests that these T cells also have some important activity.

Discussion

Since CD200 itself lacks any signaling motifs in its intracellular domain(s), and docking sites for adapter signaling molecules (25), it was hypothesized that a ligand-bearing cell (hereafter referred to as CD200R$^+$) would be most relevant for immunoregulation following increased CD200 expression (1, 4). The current studies have examined this possibility, and provide data for the existence of several CD200R$^{30}$ cell populations, one of which has potent immunosuppressive properties after admixture with CD200:Fc itself. Note that the CD200:Fc molecule used in our studies was derived from a construct using a mutant IgG2a molecule, lacking both the complement binding domains and the Fc binding domains. Thus it unlikely that binding by CD200:Fc is to Fc receptors on the cell surface. In addition, cells were preincubated with an excess of murine Ig to saturate such sites (see text). Finally, LPS stimulated splenic DC, which also possess FC receptors, do not bind CD200:Fc (see FIG. 11).

It is important to note that there is a previous report that an CD200 ligand-bearing population was present in a macrophage cell preparation (18). In these studies, in a fashion somewhat similar to that described above, a soluble chimeric protein with the extracellular domains of CD200 engineered onto domains (3+4) of rat CD4 antigen was used to screen for an CD200-binding cell population. There was no evidence for the presence of CD200-binding cells in the T cell populations studied in this report, which is in contradistinction to the data provided herein (see FIG. 13 and Table 4). The receptor for CD200 on the surface of these different cell populations may be distinct, and accord with unique functional properties in the different cells.

In studies of the adoptive transfer of increased graft survival in mice pretreated with donor-specific alloantigen infusion via the portal vein (a process which leads to upregulation of CD200 expression on DC (4)) the inventors reported that an F4/80$^+$ adherent spleen cell population was associated with the suppression of graft rejection. Similarly Streilin et al. have reported that F4/80$^+$ cells are implicated in adoptive transfer of tolerance following antigen infusion into the anterior chamber of the eye (26). F4/80$^+$ cells were found in the slow-sedimenting pool of cells found after LPS stimulation of T-depleted spleen cells. By further purification of these CD200R+ cells into F4/80+ and P4/80− cells, the inventors have been able to show that the inhibition of alloresponses seen using CD200R+ cells mixed with CD200:Fc can be accounted for by the F4/80+ cell pool (see Table 2).

One could envisage a model in which following CD200 engagement of CD200R on the surface of F4/80+ cells the latter become non-specifically suppressive (e.g. by release of cytokines) to T cells activated in their vicinity. However, the data shown in Table 3 argue against such a model. Here the inventors show that using a B10 suppressive cell pool (CD200R+) the suppression of alloimmunity seen is directed to T cells recognizing the alloantigen expressed on those CD200R+ cells. Even responses using responder cells MHC compatible with the CD200R+, F4/80+ inhibitory cells are unaffected, as are third-party immune responses. Therefore, it is concluded that T responder cells are down-regulated following direct cell:cell MHC-restricted recognition of the inhibitory CD200R+ cells. In the case of immunity to nominal antigen (rather than alloantigen), the inventors suggest that the CD200R+ cell must itself present the antigen to the responder lymphocyte in order for the latter to receive its tolerizing signal. This mechanism presumably represents a necessary safe-guard to ensure that this form of immunotolerance does not cause bystander non-specific immuno-suppression in the individual.

There has been considerable interest in the heterogeneity of DC and the significance of this to immunization/tolerance induction. DC are heterogeneous in terms of origin, cell surface phenotype, turnover in vivo and possibly function (30, 31). It is known that the induction of immunity (vs. tolerance) following antigen presentation is dependent upon the co-existence of other signaling ligands at the surface of DC (interacting with appropriate counter-ligands on the surface of other cells (e.g. stimulated T-cells)) (32-34). Thus CD80, CD86 and CD40 are all implicated as costimulator molecules in transplantation (12-17). From studies focusing on a role for the molecule CD200 in induction of unresponsiveness, it is concluded that discrete populations of DC preferentially expressing CD200 were uniquely capable of inducing tolerance to mouse allograft tissue/organs (7). The data shown above add further complexity to this model. It is now suggested that a distinct population of cells, expressing CD200R, are themselves ultimately engaged in the delivery of key immunoregulatory signals following engagement (by CD200) on the cell surface.

Example 3

Transplant Tolerance Modifying Antibody to CD200 Receptor (CD200R), but not CD200, Alters Cytokine Production Profile from Stimulated Macrophages Materials and Methods Mice: Male C3H/HEJ and C57BL/6 mice were purchased from the Jackson laboratories, Bar Harbour, Me. Mice were housed 5/cage and allowed food and water ad libitum. All mice were used at 8-12 weeks of age.

Monoclonal antibodies: The following monoclonal antibodies (mAbs) were obtained from Pharmingen (San Diego, Calif., USA) unless stated otherwise: anti-IL-2 (S4B6, ATCC; biotinylated JES6-5H4); anti-IL-4 (11B11, ATCC; biotinylated BVD6-24G2); anti-IFNγ (R4-6A2, ATCC; biotinylated XMG1.2); anti-IL-10 (JES5-2A5; biotinylated, SXC-1); anti-IL-6 (MP5-20F3; biotinylated MP5-32C11); anti-TNFα (G281-2626; biotinylated MP6-XT3); FITC anti-CD80, FITC anti-CD86, FITC anti-CD40, L3T4 (anti-mouse CD4), anti-thy1.2 and anti-Ly2.2 were obtained from Cedarlane Labs, Hornby, Ontario. The hybridoma producing DEC205 (anti-mouse dendritic cells) was a kind gift from Dr. R. Steinman, and was directly labeled with FITC; PE-conjugated rat anti-mouse CD200 (3B6) was obtained from BioSpark Inc., Mississauga, Ontario, Canada (Regheb et al. (1999)). FITC conjugation of mouse CD200Fc was performed by Dr. D. Clark (McMaster University, Hamilton, Ontario). A rat monoclonal antibody to CD200R, (2F9), was obtained following immunization with CHO-cells transduced with a pBK vector containing a cDNA for the CD200R (Gorczynski-in preparation; also Wright et la. (2000) and Gorczynski et al. (2000)). This mAb blocked binding of FITC-CD200Fc to LPS stimulated macrophages (below) and stained CHO-CD200R transduced cells but not CHO cells transduced with an empty pBK vector (see also (Gorczynski et al. (2000)). Fab and F(ab')$_2$ samples of anti-CD200 and anti-CD200R were prepared in standard fashion using enzyme digestion.

Strepavidin horse radish peroxidase and recombinant mouse GM-CSF was purchased from Pharmingen (San Diego, Calif.).

Preparation of cells: Single cell spleen suspensions were prepared aseptically and after centrifugation cells were resuspended in α-Minimal Essential Medium supplemented with 2-mercaptoethanol and 10% fetal calf serum (αF10). Putative CD200R+ LPS splenic Mph, stained (>30%) with FITC-CD200Fc, were obtained by velocity sedimentation of cells cultured for 48 hrs with 1 mg/ml LPS, and represented the pool of cells sedimenting with velocity 3-4 mm/hr[21]. These cells did not stain with DEC205 (<5%), but were >95% FITC-MAC-1+.

Portal Vein (pv) Immunization with Dendritic Cells (DC) was Performed as Described Earlier (Gilchrest et al. (1997)):

Bone marrow derived dendritic cells (DC) for pv immunization were obtained by culture for 7 days of L3T4, anti-thy 1.2, anti-Ly2.2 treated bone marrow cells in the presence of 500 U/ml GM-CSF (Fabrega et al. (1995)). An aliquot of the sample stained with FITC conjugated DEC205 mAb showed a mean staining in the order of 91%+8% (and <6% MAC-1+).

Skin Transplantation: was Performed Essentially as Described Elsewhere (Gorczynski (1992)).

Cytotoxicity and Cytokine Assays:

In allogeneic mixed leukocyte cultures (MLC) used to assess cytokine production C3H responder cells were stimulated with equal numbers of mitomycin-C treated (45 min at 37° C.) C57BL/6 spleen stimulator cells in triplicate in αF10. Supernatants were pooled at 40 hr from replicate wells and assayed in triplicate in ELISA assays or bioassays for lymphokine production as described below.

Where cytokine production was measured from mAb stimulated DC or splenic Mph, cells were cultured for 24 hrs with plate-bound mAbs, supernatants collected, and cytokines measured as below.

All cytokines were measured in ELISA assays, with capture and biotinylated detection mAbs as described above. Varying volumes of supernatant were bound in triplicate at 4° C. to plates pre-coated with 100 ng/ml mAb, washed ×3, and biotinylated detection antibody added. After washing, plates were incubated with strepavidin-horse radish peroxidase (Cedarlane Labs), developed with appropriate substrate and OD405 determined using an ELISA plate reader.

Recombinant cytokines for standardization were obtained from Pharmingen (U.S.A.). All assays showed sensitivity in the range 40 to 4000 pg/ml.

Results

Figure 14:
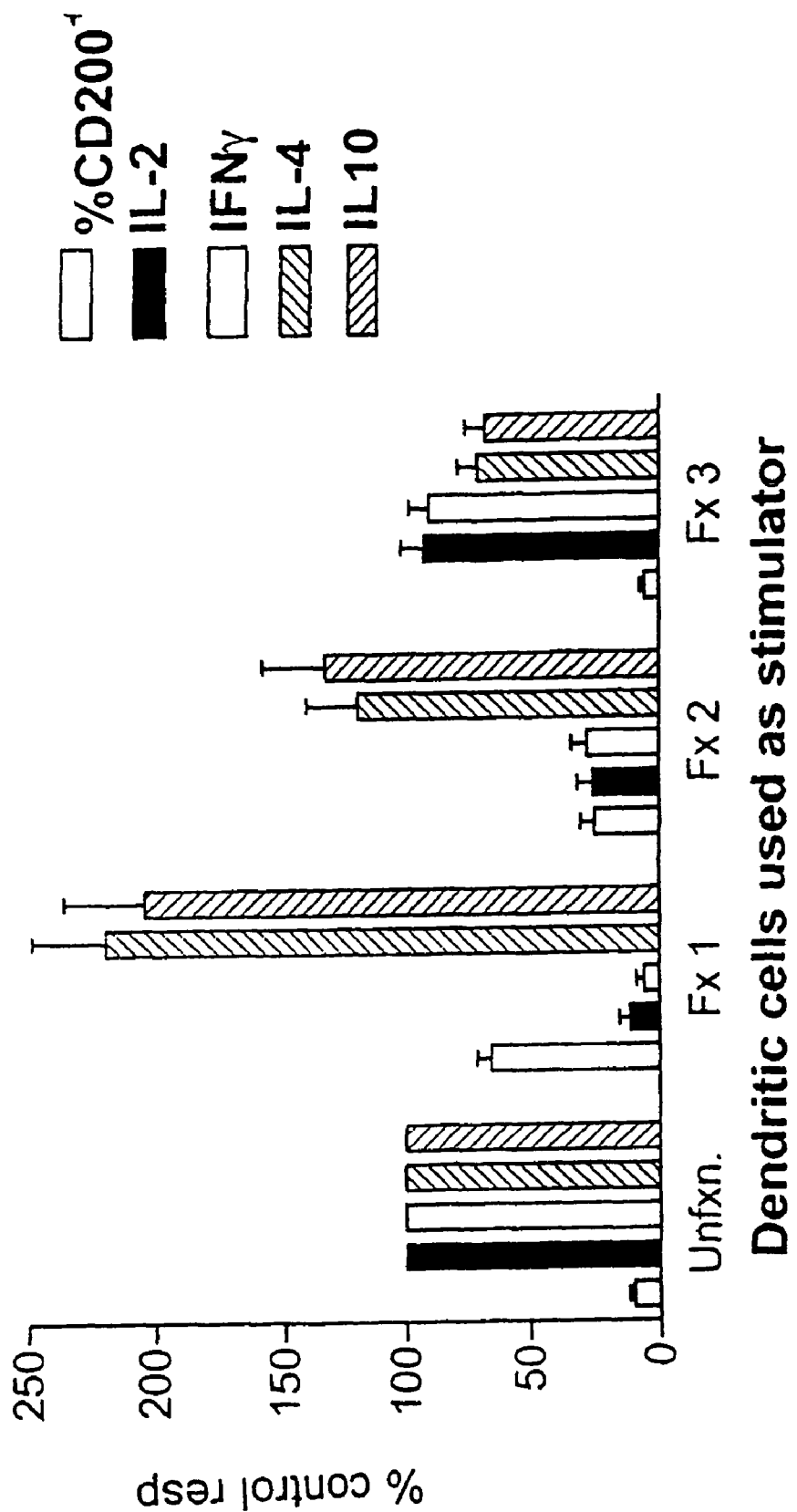
FIG. 14 is a graph showing CD200$^-$ DC stimulated type 1 while CD200$^+$ DC stimulate type-2 cytokine production. C3H splenocytes were stimulated in vitro with unfractionated or size fractionated (by velocity sedimentation) LPS-treated bone marrow DC. Cytokines were assayed at 40 hrs. An aliquot of the different size DC fractions were stained with PE-3B6 for CD200 expression. Absolute cytokine production (pg/ml) in control cultures (2×10$^5$ unfractionated DC added) for IL-2, IFNγ, IL-4 and IL-10 respectively were: 980±145, 780±155, 65±15 and 220±45.

CD200⁻ and CD200⁺ DC Stimulate Type-1 or Type-2 Cytokine Production Respectively in MLC:

C57BL/6 bone marrow derived DC were stimulated overnight with LPS before fractionation by size sedimentation (Gorczynski et al. (1999). 3 fractions were studied, comprising small cells (Fx 1: slow sedimenting, 3-4.5 mm/hr), intermediate size (Fx 2) and large cells (Fx 3: fast sedimenting, 6-8 mm/hr). An unfractionated DC cell sample was also used for stimulation, with cytokine production from these cultures recorded as control values (nominally 100-data to far left of FIG. 14). $2 \times 10^5$ cells were used in MLC with $5 \times 10^5$ C3H spleen responder cells, and cytokine production assayed 40 hrs later. In addition an aliquot of cells was stained with PE-anti-CD200. Data in FIG. 14 (1 of 3 studies) show that CD200+ DC (predominantly slow sedimenting cells, contained in Fx 1) preferentially stimulate type-2 cytokine production, and inhibit type-1 cytokine production, in MLC compared with an unfractionated population of LPS-stimulated allogeneic DC. These cells also prolong tissue allograft survival in vivo (Gorczynski et al. (1998); Gorczynski et al. (1999)).

A similar inhibition of type-1 cytokine production in vitro is seen using 100 ng/ml of the soluble immunoadhesin CD200Fc (Gorczynski et al. (1999)). The inventors have shown elsewhere that this inhibition is enhanced by inclusion in MLC of LPS-stimulated splenic Mph which can be stained by FITC-conjugated CD200Fc (i.e. presumed to represent an CD200$^{r+}$ population) (Gorczynski et al. (2000). Data in Table 5 are typical of results of such studies, where LPS stimulated CD200$^{r+}$ Mph were obtained at 48 hrs by velocity sedimentation of cells obtained from spleen cell cultures. These cells bind FITC-CD200Fc (Gorczynski et al. (2000)) and are stained (>30%) with monoclonal anti-CD200R, but <6% with anti-CD200 mAb (RMG unpublished). Synergistic inhibition of type-1 cytokine production was seen using CD200$^{r+}$ cells in the presence of CD200, whether CD200 was delivered in the form of soluble CD200Fc or as CD200⁺ DC (from bone marrow cultures). Note that despite the small percentage (~5-10% averaged over 6 studies) of CD200⁺ cells in the stimulator DC pool itself (e.g. see unfractionated population of DC in FIG. 14, where 10% of unfractionated cells were CD200⁺) no inhibition was seen on addition of CD200R⁺ cells only to these stimulator DC (compare rows 1, and 3). Titration of exogenous CD200⁺ cells (or CD200Fc) confirms that this is due to a "threshold" for the regulatory signals delivered to antigen-activated T cells following CD200:CD200R interaction; in studies not published the inventors found that a minimum of $3 \times 10^4$ CD200⁺ cells (or >50 ng/ml CD200Fc) were necessary before exogenous addition of CD200R⁺ cells produced synergistic inhibition. Increasing CD200R⁺ cells alone did not increase immunoregulation (3rd row), but in the presence of exogenous CD200 from any source, CD200R⁺ cells clearly produce augmented immunoregulation (see 4th and 6th row of Table).

F(ab')₂ Anti-CD200 or Anti-CD200R Reverse Inhibition of Type-1 Cytokine Production in MLC:

The inventors have argued elsewhere that the inhibitory signal delivered by CD200 is a result of engagement of CD200R itself, since the intracellular domains of CD200 lack signaling motifs (or docking motifs for adapter molecules) (8). The inventors have shown earlier that an anti-CD200 mAb (3B6) blocks the inhibition of alloreactivity both in vivo (leading to graft rejection) and in vitro (Gorczynski et al. (1998); Gorczynski et al. (2000)). In principle, since these studies were performed with whole Ig, it remained theoretically possible that cross-lining of surface CD200 could have occurred following treatment with anti-CD200, leading not to blocking of inhibition, but to delivery (via CD200 itself) of a stimulatory signal.

To address this issue directly, the inventors compared the effect of whole or F(ab')₂ fragments of anti-CD200 or anti-CD200R on the inhibition of type-1 cytokine production in vitro induced by CD200⁺ DC added to CD200$^{r+}$ Mph, as in Table 5. F(ab')₂ preparations of either reagent, as well as whole anti-CD200, abolished the inhibition of type-1 cytokine production (Table 6). However, whole anti-CD200R failed to block the inhibition seen following addition of CD200, including the synergy in inhibition in the presence of CD200$^{r+}$ cells (see 6th and 12th rows of Table 6). Moreover, infusion of these reagents in vivo into skin grafted mice (following pv immunization), again led to reversal of graft prolongation with whole anti-CD200, or F(ab')₂ fragments of anti-CD200 and anti-CD200R, but not whole anti-CD200R Ig. Similar results (to those seen with F(ab')₂ Ig) were obtained with monovalent (Fab) mAb preparations. The inventors hypothesize that anti-CD200 blocks suppression mediated by CD200:CD200R interactions by simple neutralization of CD200. Anti-CD200R blocks suppression only if it binds at the surface of the CD200R⁺ cells without simultaneously signalling the CD200 receptor. Thus Fab and F(ab')₂ fragments of anti-CD200R produce blockade of immunoregulation while whole anti-CD200R crosslinks receptor on CD200R⁺ Mph and delivers immunoregulatory signal directly.

Figure 16:
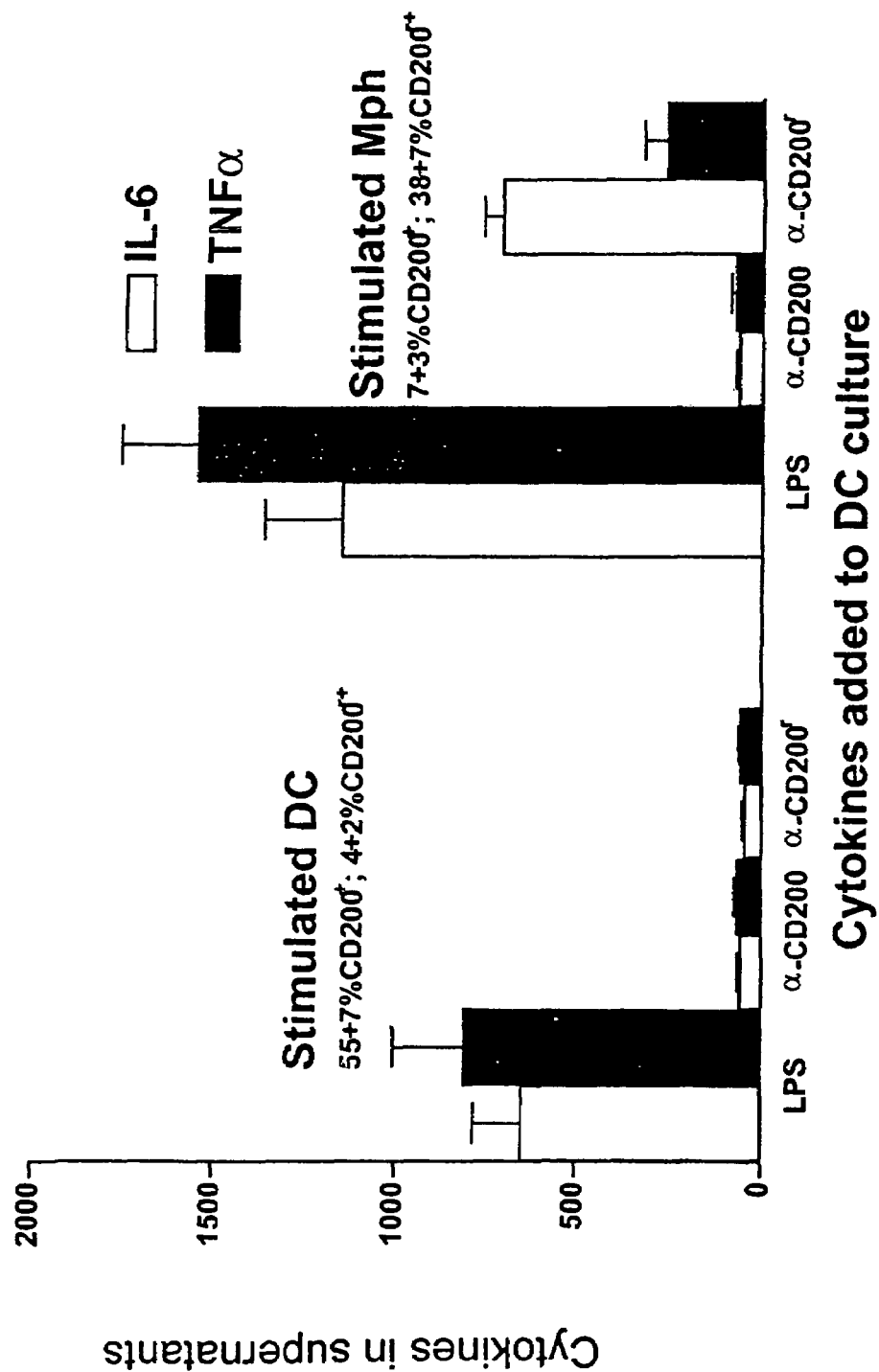
FIG. 16 is a graph showing the stimulation of IL-6 or TNFα in DC or macrophage (Mph) by anti-CD200 and anti-CD200R. Stimulation of TNFα or IL-6 in DC or spleen Mph by LPS or plate-bound anti-CD200 or anti-CD200R (see text for details). Cytokines were measured in supernatants at 24 hrs. % staining with anti-CD200 or anti-CD200R for DC or splenic Mph is shown.

Evidence that Crosslinking of the Target of Anti-CD200R, but not of Anti-CD200, Directly Stimulates Cell Cytokine Production:

A final series of studies was designed to investigate the evidence for direct signaling induced by crosslinking of CD200 or CD200R on the cell surface. Anti-CD200 or anti-CD200R were adhered to polystyrene coated culture plates (mAb concentration used for coating, 50 µg/ml), and splenic CD200R⁺ Mph, or CD200⁺ DC, were added (cells were first enriched by velocity sedimentation-see FIG. 14 and (Gorczynski et al. (2000)). Cytokines (IL-6, capable of inducing polarization to type 2 cytokine production; or TNFα, capable of augmenting type-1 cytokine production) were assayed in the supernatant at 24 hrs. Data are shown in FIG. 16 (1 of 3 studies). Cytokine induction by LPS stimulation (100 ng/ml) was used as a control.

Anti-CD200 was unable to stimulate cytokine production from DC or Mph. In contrast, while LPS induced more TNFα than IL-6 from both splenic Mph and DC, anti-CD200R (but not anti-CD200) led to direct stimulation predominantly of IL-6 from Mph only (CD200R⁺), but not from DC (CD200⁺), consistent with the hypothesis provided as explanation for the data of Table 6 and FIG. 15 (failure of anti-CD200R to inhibit regulation of cytokine synthesis and inhibition of rejection). In a final study, CD200R⁺ Mph (again enriched by velocity sedimentation) were added to cultures of spleen cells and allogeneic DC, in the presence/absence of anti-CD200R or anti-CD200 (control Ig), with/without exogenous anti-IL-6 mAb, to examine the role for induction of IL-6 in the anti-CD200$^r$ induced immunoregulation seen. In separate cultures, F(ab')₂ fragments of anti- CD200R were used in cultures with/without anti-IL-6. Data for one of three studies are shown in Table 7.

Figure 13:
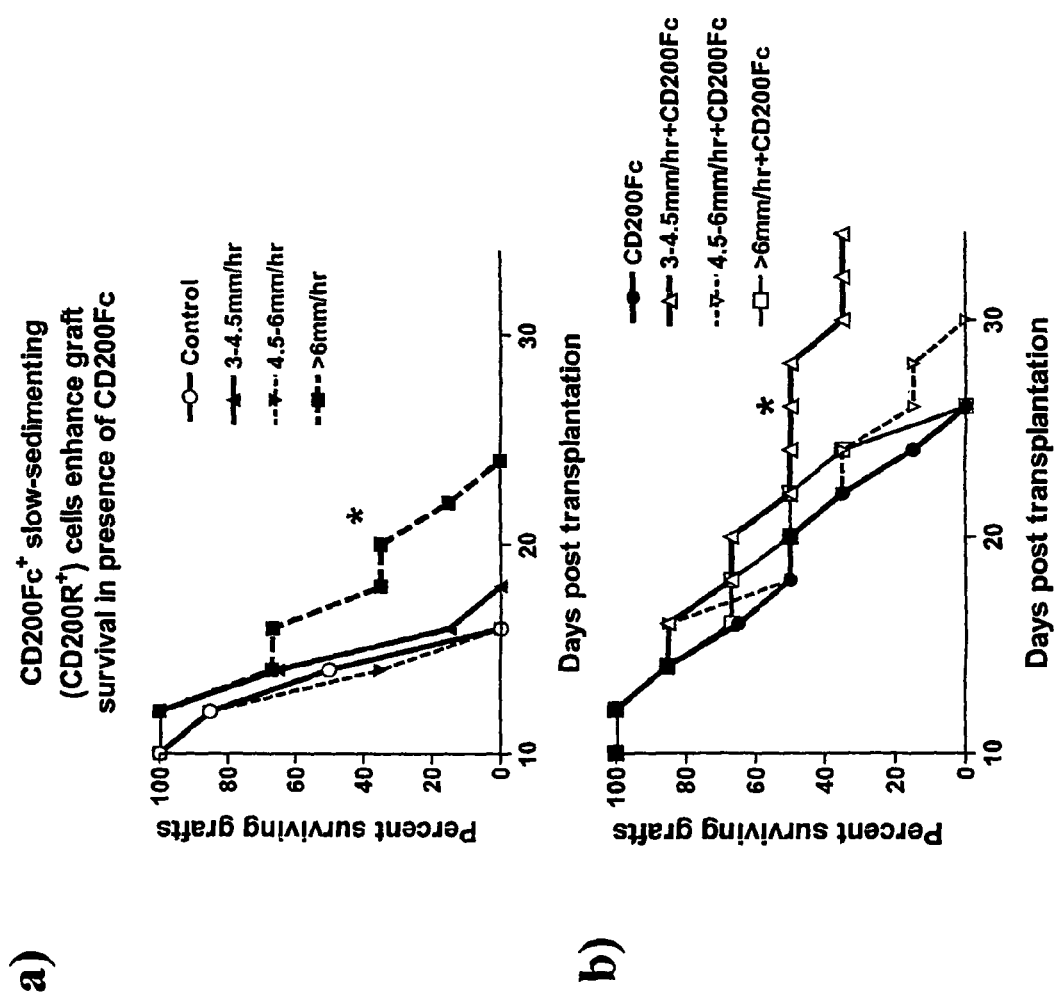
FIG. 13 is a graph showing skin allograft survival after infusing slow-sedimenting spleen cells (capable of binding FITC-CD200:Fc-see FIG. 12, i.e. CD200R+) along with soluble CD200:Fc. Various populations of spleen cells were obtained from a pool of LPS-stimulated T-depleted spleen cells from 6 C57BL/6 mice (see FIG. 12). Groups of 7 C3H mice received C57BL/6 skin grafts, along with cells from these different spleen pools, with or without infusion of CD200:Fc (10 mg/mouse; two doses only at 48 hour intervals). Skin graft survival was followed daily. * p<0.05, compared with all other groups (Mann-Whitney U-test).

It is clear from these data that once again inclusion of whole, but not F(ab')$_2$ (or Fab—not shown) digests of anti-CD200R both induce immunosuppression in these cultures when added alone (presumably reflecting contact with endogenously expressed CD200R), and that this is augmented by addition of exogenous CD200R$^+$ cells. Anti-CD200 mAb has no such effect. More interesting, the inhibition of type-1 cytokine production induced by triggering of CD200R$^+$ cells is attenuated (though not completely relieved) by anti-IL-6 mAb. This is consistent with data in FIG. 13 showing induction of IL-6 by anti-CD200R mAb, and elsewhere suggesting that IL-6 is important in promoting polarization to type-2 cytokine production (Rincon et al. (1997); Gorczynski et al. (1997)).

Discussion

Figure 15:
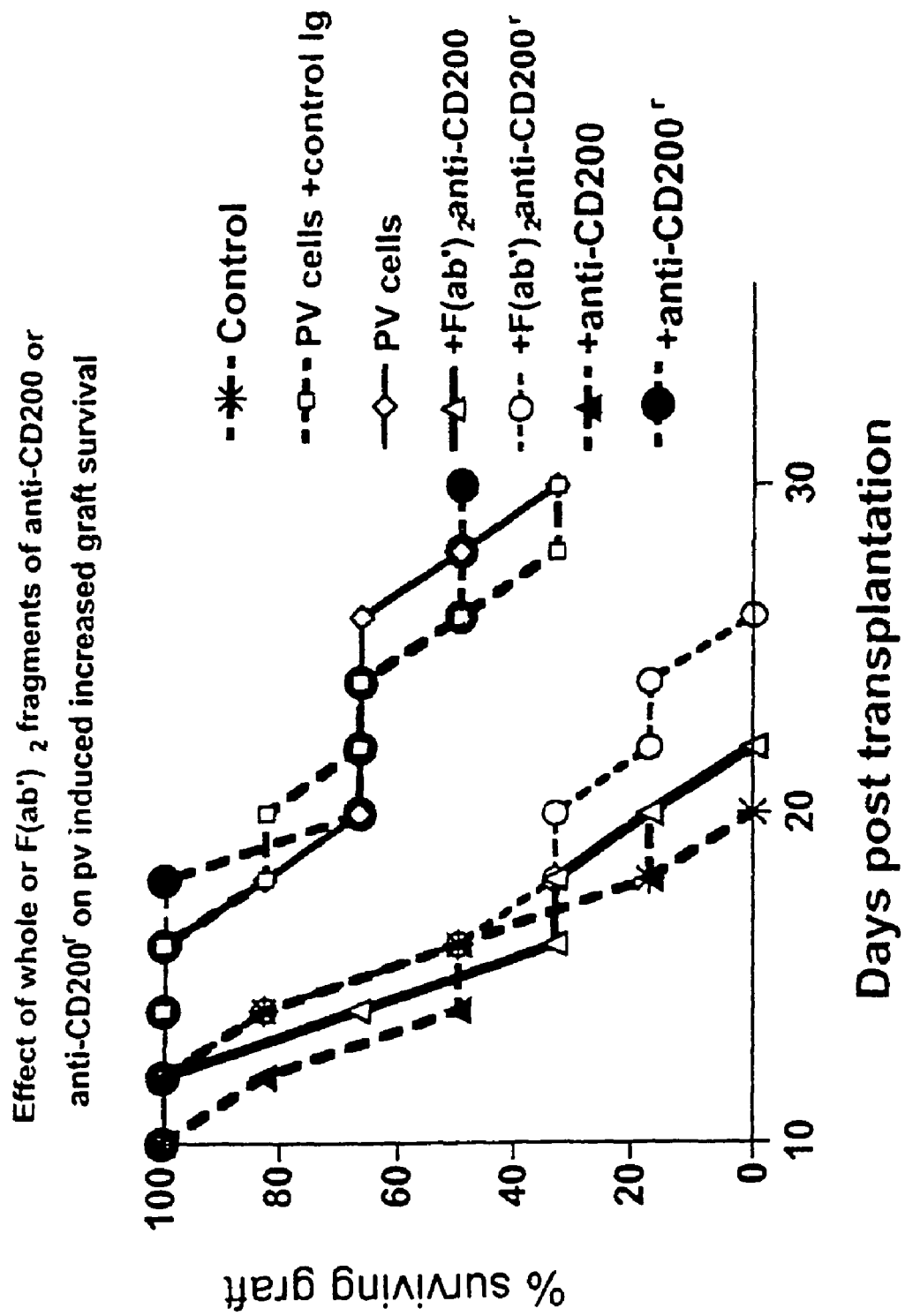
FIG. 15 is a graph showing the effect of whole or F(ab')$_2$ fragments of anti-CD200 or anti-CD200R on pv induced increased graft survival. F(ab')$_2$ preparations of both anti-CD200 and anti-CD200R block the increased C57BL/6 skin graft survival in C3H mice seen after pre-transplant pv immunization with C57BL/6 DC. Mice received 5 infusions of F(ab')$_2$ mAbs (100 µg/mouse) at 36 hr interval beginning on the day of transplant. *p<0.05 compared with control (no DC). Data using whole anti-CD200 or anti-CD200R Ig show inhibition only with anti-CD200 mAb.

In the present example, Fab and F(ab')$_2$ mAbs to CD200 and CD200R have been used to explore further the mechanism(s) of action of these molecules in suppression of MLC and of graft rejection in vivo. Both reagents block inhibition of type-1 cytokine production in vitro, and reverse increased graft survival in vivo following pv immunization with donor DC (Table 6; FIG. 15). Interestingly whole anti-CD200, but not anti-CD200R, produced the same effects (Table 6; FIG. 15). These data would support the hypothesis that simple neutralization of CD200 suffices to block its signal, whereas cross-linking of surface CD200R can itself induce immunoregulatory signals in the target (macrophage) population. Further support for such a hypothesis comes from the evidence that cross-linking of CD200R, but not CD200, on the cell surface led to direct cytokine production (IL-6) by antigen-bearing (CD200R) cells (FIG. 16). Moreover, since addition of anti-IL-6 mAb into cultures where immunoregulation was induced by cross-linking of CD200R$^+$ cells (Table 7) attenuated the suppressive activity of those cells (for blocking type-1 cytokine production), these data imply that induction of IL-6 following triggering of CD200R plays an important, but not the only, role in this immunosuppressive signal.

Taken together, these data imply a key role for CD200R+ cells in immunoregulation. CD200R is likely to be of fundamental importance in transplantation, allergy and autoimmunity, and other clinical conditions of perturbed immunoregulation.

Example 5

Figure 17:
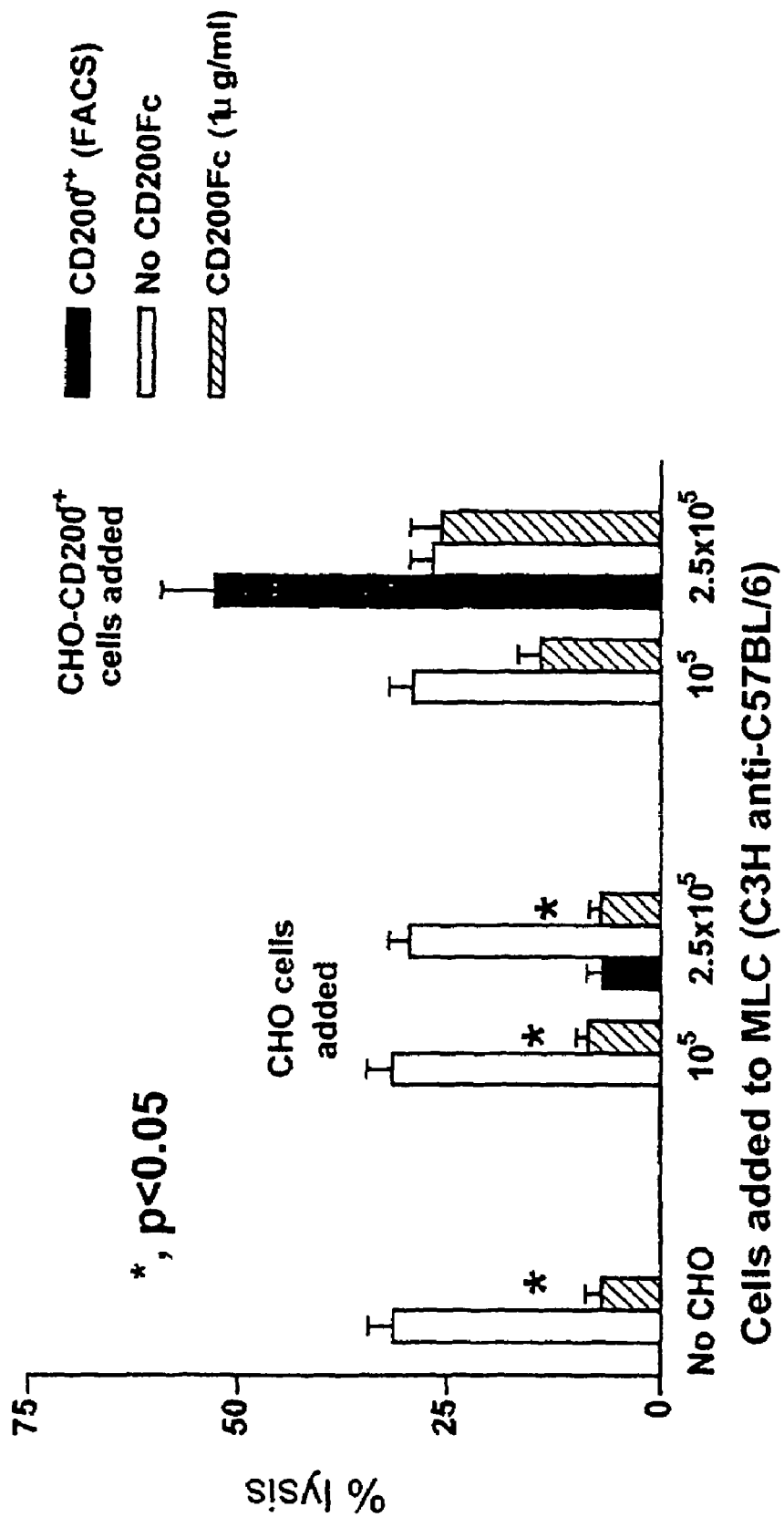
FIG. 17 is a bar graph showing that CHO-CD200R$^+$ cells act as decoy receptor to block inhibition of induction of CTL by CD200Fc.
Figure 18:
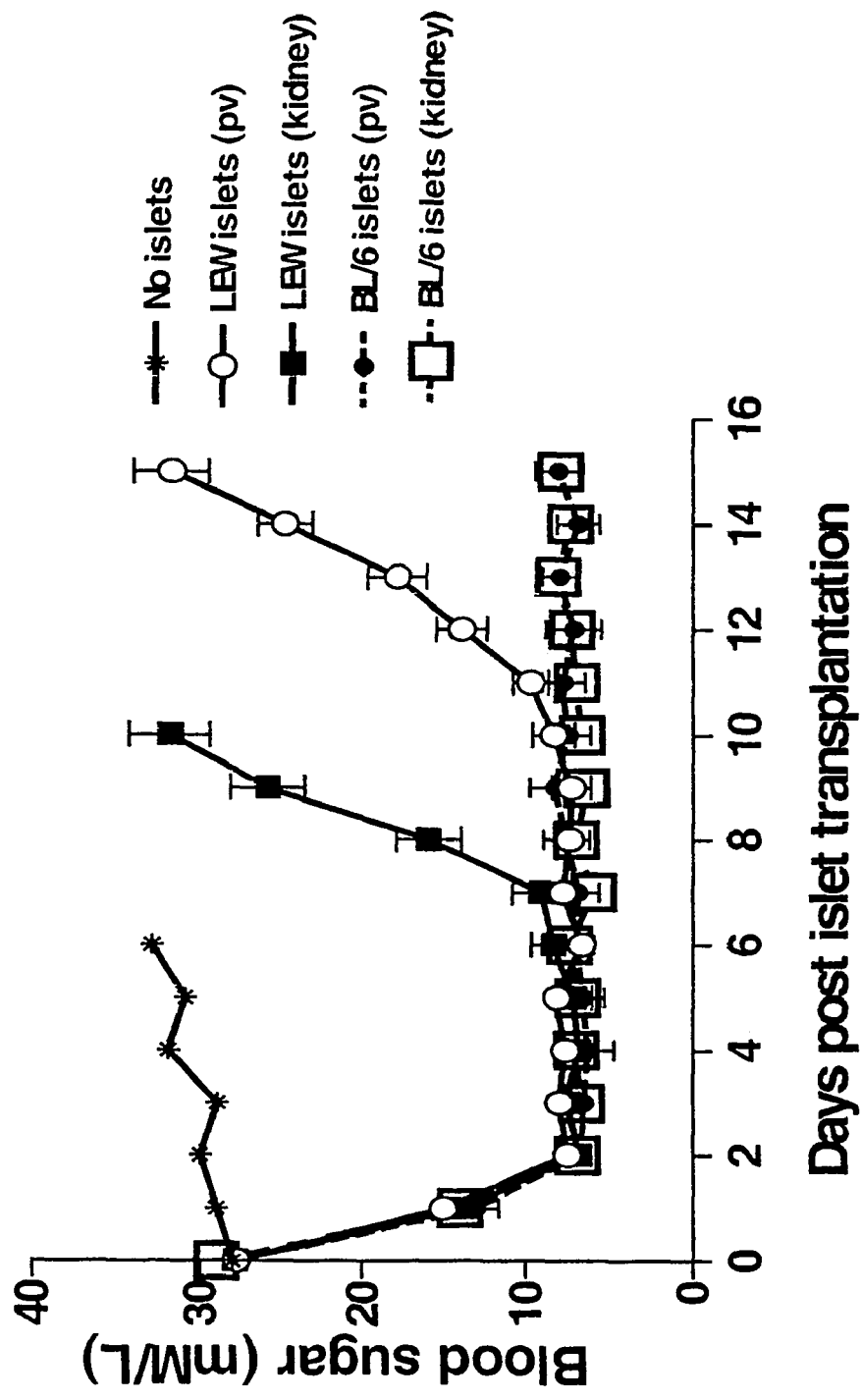
FIG. 18 is a graph showing restoration of normoglycemia in diabetic mice using syngeneic (BL/6) or xenogeneic (LEW rat) islets. All points represent arithmetic mean (±SD) of blood glucose in groups of 4 mice rendered diabetic by streptozotocin, and receiving ~400 islets transplanted under the kidney capsule or injected through the portal vein 24 hrs after iv injection of 100 ml anti-asialo-GM1 antibody. All mice received weekly ip injections of rapamycin (10 mg/Kg). Glucose control was superior in mice receiving pv injections of LEW islets compared with kidney capsule transplantation (p<0.05, Mann-Whitney U-test).

CHO-CD200$^{r+}$ Cells Act as Decoy Receptor to Block Inhibition of Induction of CTL by CD200Fc A CD200 receptor (CD200R1) was expressed in CHO cells (stained >50% by FACS with an anti-CD200R antibody). The CHO cells (2 different numbers used, $10^5$ and $2.5 \times 10^5$), either vector control transfected or CD200R1 transfected were added to MLC cultures ($5 \times 10^6$ C3H spleen vs $5 \times 10^6$ mitomycin-C treated C57BL/6 spleen), in the presence/absence of CD200Fc. Without any CHO cells added, CD200Fc suppresses (left of panel). CHO (vector transfected; ~6% stained by anti-CD200R antibody) does not modify inhibition (centre panels). CHO transfected with CD200R1 (~55% stained) block the inhibition by CD200FC (right hand panels). The results are shown in FIG. 17.

Example 6

A CD200Fc Immunoadhesin Prolongs Rat Islet Xenograft Survival in Mice

Summary

Summary: A solubilized form of the CD200 molecule, CD200Fc, has been shown to prolong survival of rat islet xenografts. This effect was abolished by anti-CD200 or Fab/F(ab')$_2$ anti-CD200R mAbs, but not by whole anti-CD200R (anti-CD200R Ig).

Methods: Streptozocin-treated mice, injected with anti-asialo-GM1 antibody, received rat islets (~400/mouse) under the kidney capsule or injected into the portal vein, along with rapamycin treatment. Thereafter mice received injections of CD200Fc (10 μg/mouse/injection) or control mouse IgG2. Blood glucose was monitored daily. Some mice received additional injections of anti-CD200/-CD200R mAbs.

Materials and Methods

Mice: Male C57BL/6 mice were purchased from the Jackson laboratories, Bar Harbour, Me. Mice were housed 5/cage and allowed food and water ad libitum. All mice were used at 8-12 weeks of age. Lewis rats (LEW) were obtained at 8 weeks of age from Sprague Dawley.

Monoclonal antibodies: The following monoclonal antibodies (mAbs) were obtained from Pharmingen (San Diego, Calif., USA) unless stated otherwise: anti-IL-2 (S4B6, ATCC; biotinylated JES6-5H4); anti-IL-4 (11B11, ATCC; biotinylated BVD6-24G2); anti-IFNγ (R4-6A2, ATCC; biotinylated XMG1.2); anti-IL-10 (JES5-2A5; biotinylated, SXC-1). Anti-mouse CD200 and PE-conjugated rat anti-mouse CD200 was obtained from BioCan., Mississauga, Ontario, Canada. A rat monoclonal antibody to CD200R, was produced by immunization with CHO-cells transduced with a pBK vector containing a cDNA for CD200R as described in Example 4. Fab and F(ab')$_2$ samples of anti-CD200 and anti-CD200R were prepared in standard fashion using enzyme digestion.

Strepavidin horse radish peroxidase and recombinant mouse GM-CSF was purchased from Pharmingen (San Diego, Calif.). Rabbit anti-asialo-GM1 antibody was purchased from Wako Chemicals, Japan.

Preparation of spleen cells, islet isolation and transplantation: Single cell spleen suspensions were prepared aseptically from pools of stock mice and after centrifugation cells were resuspended in α-Minimal Essential Medium supplemented with 2-mercaptoethanol and 10% fetal calf serum (αF10). For islet isolation, LEW rats or C57BL/6 mice were anesthetized with tribromethanol (Avertin). Pancreatic islets were isolated by collagenase digestion (75), purified on a Ficoll density gradient, and hand-picked for culture. Islets were cultured for 84 hrs in 95% air/5% Co2 at 37° C. in αF10 supplemented with 12 mM HEPES and 20 μg/ml amphotericin B. Islets were harvested from culture and transplanted (~400/recipient) either via the portal vein, or under the kidney capsule, to individual C57BL/6 mice.

Islet transplantation: Mice were rendered diabetic by treatment with 250 mg/Kg streptozocin (Sigma, St. Louis, Mo.) dissolved in citrate buffer, pH 4.5. Blood glucose levels were determined daily using a Medisense 2 glucometer (Mississauga, Ontario, Canada), using samples taken from the tail vein. Only animals with blood glucose >20 mM were used as diabetic recipients. Approximately 3-4 days following streptozocin treatment mice received a single intravenous injection with 100 µl of anti-asialo-GM1 antibody, followed 24 hrs later by islet transplantation. Anti-asialo-GM1 was used to deplete NK cells, known to be important in xenorejection (see also (76)). Return of blood glucose levels to a normal range (5-8 mM) was used as an indicator of graft function, while a sudden rise to levels >10 mM, for 2 consecutive days, was indicative of rejection.

CD200Fc: The soluble immunoadhesin, CD200Fc, was prepared in a baculovirus system as described elsewhere (1). Mice received intravenous infusions (10 µg/mouse) at 2 day intervals for the times indicated in the individual experiments. All mice also received weekly ip injections with rapamycin (10 mg/Kg), beginning on the day of transplantation.

Cytotoxicity and cytokine assays: In mixed leukocyte cultures (MLC) used to assess cytokine production $5 \times 10^6$ C57BL/6 responder spleen cells were stimulated in triplicate in 2 ml αF10 in 24-well plates with equal numbers of mitomycin-C treated (45 min at 37° C.) LEW or BALB/c spleen stimulator cells. Supernatants were pooled at 40 hr from replicate wells and assayed in triplicate in ELISA assays for cytokine production capture and biotinylated detection mAbs as described above. Varying volumes of supernatant were bound in triplicate at 4° C. to plates pre-coated with 10 ng/ml mAb, washed ×3, and biotinylated detection antibody added. After washing, plates were incubated with strepavidin-horse radish peroxidase (Cedarlane Labs), developed with appropriate substrate and $OD_{405}$ determined using an ELISA plate reader. Recombinant cytokines for standardization were obtained from Pharmingen (U.S.A.). All assays showed sensitivity in the range 40 to 4000 pg/ml.

Where cytotoxicity was assayed, cells were harvested from MLC at 5 days and titrated at different effector:target ratios for killing (4 hrs at 37° C.) of $^{51}$Cr-labeled 72 hr LEW rat ConA spleen cell blasts or P815 tumor cell targets (for cells stimulated with mitomycin-C treated BALB/c spleen cells).

Results

LEW Rat Islets Transplanted into the Portal Vein are Superior to those Placed Under the Kidney Capsule in Reversing Hyperglycemia in Streptozotocin-Treated Mice:

C57BL/6 mice were rendered diabetic by single ip injection of streptozocin. Blood sugar was monitored daily, and when >20 mM all mice received 100 µl anti-asialo-GM1, followed 24 hrs later by islet transplantation (~400 islets/recipient). C57BL/6 or LEW rats were used as a source of islets for transplantation, and all groups contained 4 mice. Animals received ip rapamycin, 10 mg/kg, weekly from the day of transplantation. In separate groups islets were infused into the portal vein (pv) or transplanted under the kidney capsule. Animals were monitored daily for glucose control. Typical data (one of three studies) are shown in FIG. 16. It is clear that while syngeneic islet transplantation led to prolonged euglycemia (>20 days), rat xenotransplants restored blood sugar control for approximately 8 days (grafts under the kidney capsule), or for longer, 11-12 days ($p<0.05$) if given by pv injection.

Nephrectomy Reverses Euglycemia Following Transplantation of Xenogeneic Islets Under the Kidney Capsule, While Infusion of CD200Fc Further Prolongs Blood Glucose Control in Transplanted Mice:

The inventors have previously reported on the ability of a novel immunoadhesin, CD200Fc, to cause immunosuppression leading to increased allograft survival and decreased autoimmune disease. In order to examine whether the same molecule could promote rat xenoislet graft survival C57BL/6 mice received LEW islet grafts under the kidney capsule or via the pv route, followed by 4 or 8 infusions of CD200Fc (10 µg/mouse/injection) at 48 hr intervals. Two additional control groups of islet-grafted rats were nephrectomized or received a single iv injection (200 ml/mouse) of an anti-rat antibody 2 days following LEW islet transplantation.

The inventors confirmed, as expected, that either nephrectomy, or treatment with anti-rat antiserum, rapidly reverses the euglycemia achieved following transplantation of xenogeneic islets under the kidney capsule. In control studies (not shown) nephrectomy, but not anti-rat antibody, also reversed euglycemia following transplantation of syngeneic (C57BL/6) islets under the kidney capsule. Interestingly, 4 infusions of CD200Fc given at 48 hr intervals extended blood glucose control to 12-13 days compared with no CD200Fc ($p<0.05$), while 8 injections gave even greater prolongation of glucose control ($p<0.05$ compared with 4 injections of CD200Fc).

When islets were infused via the pv route, again glucose control was manifest longer, in the absence of additional treatments compared with transplants under the kidney capsule, but was reversed immediately by anti-rat antibody, though not by nephrectomy. CD200Fc once more led to even more prolonged blood glucose control compared with islet grafts alone, though after using 8 injections of CD200Fc there was no longer a difference in the length of euglycemia achieved following pv infusion or using transplantation under the kidney capsule as the route of engraftment.

F(ab')$_2$ Anti-CD200 or F(ab')$_2$ Anti-CD200R Inhibits Prolongation of Euglycemia Following Infusion of CD200Fc, While Anti-CD200R Ig Synergizes with CD200Fc to Further Prolong Euglycemia:

Previous studies have established a role for CD200:CD200R interactions in the prolongation of survival following allotransplantation (36). Specifically the inventors reported that mere neutralization of CD200 (using F(ab')$_2$ anti-CD200) was sufficient to block immunosuppression following increased CD200 expression, while direct signaling by anti-CD200R Ig was itself immunosuppressive (Example 4). Fab and F(ab')$_2$ anti-CD200R could also inhibit suppression signaled by CD200, presumably by acting as an antagonist at the cell surface CD200 receptor. In order to examine if these same CD200:CD200R interactions were responsible for the increased survival of islet xenografts, the inventors performed the following study.

C57BL/6 mice received LEW islets, transplanted under the kidney capsule (FIG. 19) or infused into the pv (FIG. 20), along with anti-asialo-GM1 and rapamycin as before. All groups also received CD200Fc (5 injections of 10 µg/mouse iv at 48 hr intervals). Separate groups received in addition either anti-CD200R Ig or F(ab')$_2$ anti-CD200 or F(ab')$_2$ anti-CD200R (200 µg/mouse iv on the day of islet transplantation and 72 hrs later). Blood glucose was monitored as before (see FIGS. 19 and 20). Data in FIGS. 19 and 20, from one of two such studies, confirm and extend the previous observations. Firstly, pv islet transplantation alone led to more prolonged glucose control than transplantation under the kidney capsule (see FIGS. 19 and 20). There was no significant difference between these routes of transplantation when 5 infusions of CD200Fc were also given. Regardless of the route of transplantation, F(ab')$_2$ anti-CD200 or F(ab')$_2$ anti-CD200R abolished completely the effect of infusing CD200Fc, restoring glucose control to levels seen using islets alone, while anti-CD200R Ig showed a synergistic enhancement (with CD200Fc) of glucose control.

Figure 21:
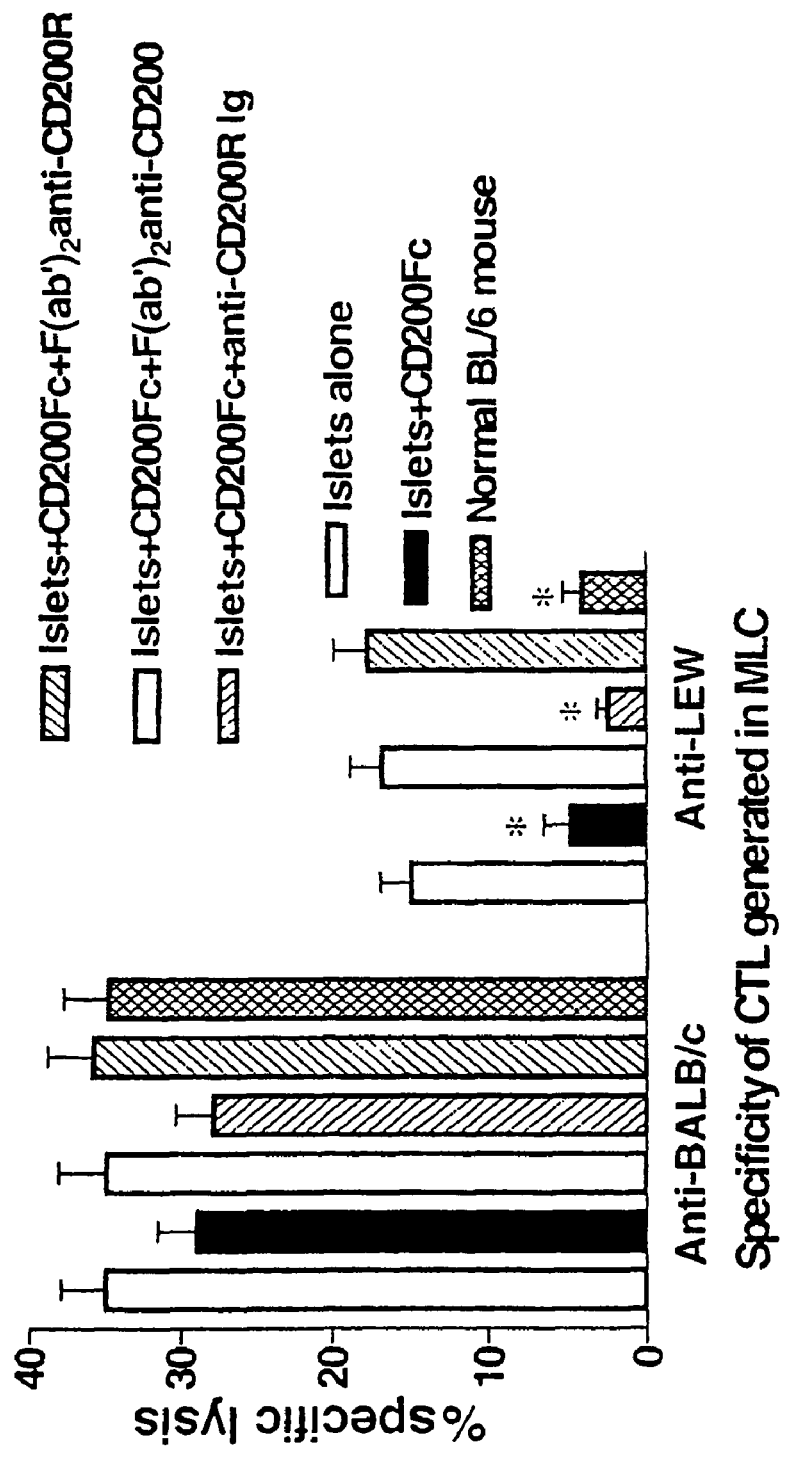
FIG. 21 is a graph showing inhibition of generation of rat-specific CTL, and altered cytokine production, after in vitro restimulation of spleen cells from mice receiving LEW islets under the kidney capsule along with CD200Fc, with/without further anti-CD200/anti-CD200R antibody-see FIG. 19 for doses of reagents used. Mice were sacrificed at day 9 post transplantation, spleen cells pooled within groups (4/group) and cultured in triplicate. Data show arithmetic mean (±SD) for CTL harvested from cultures at day 5, or from triplicate measurements by ELISA of IFNγ and IL-4 levels (pg/ml) in 40 hr culture supernatants. A control group received no islet transplantation. *, p<0.05 compared with group receiving islets and no other treatment.

Inhibition of CTL Generation, and Type-1 Cytokine Production, in Xenotransplanted Mice Receiving CD200Fc and/or Anti-CD200R Ig:

In allotransplanted mice, infusion of CD200Fc and/or treatment with anti-CD200R Ig both improves graft survival and alters in vitro MLC responses, with decreased CTL generation and type-1 cytokine production (but with increased type-2 cytokine production). In order to assess whether the same immunomodulation occurred in mice receiving rat islet transplants, groups of 4 diabetic mice received LEW islets transplants under the kidney capsule as described in FIG. 19, along with subsequent treatment with CD200Fc alone, or in combination with anti-CD200R Ig, or F(ab')$_2$ anti-CD200/-anti-CD200R. Animals in all groups were sacrificed at 9 days (by this time mice receiving islets only, or islets+F(ab')$_2$ antibody were hyperglycemic, with blood sugar in the range 1±26 mM-see FIG. 19), spleens pooled within groups and cell suspensions made. Cells were incubated with mitomycin-c treated LEW or BALB/c spleen stimulator cells and assayed for cytokine production (ELISA using 40 hr culture supernatants) or CTL (day 5 with $^{51}$Cr-labeled target cells). Data for one of two studies are shown in FIG. 21 (panels a) and b)).

Figure 22:
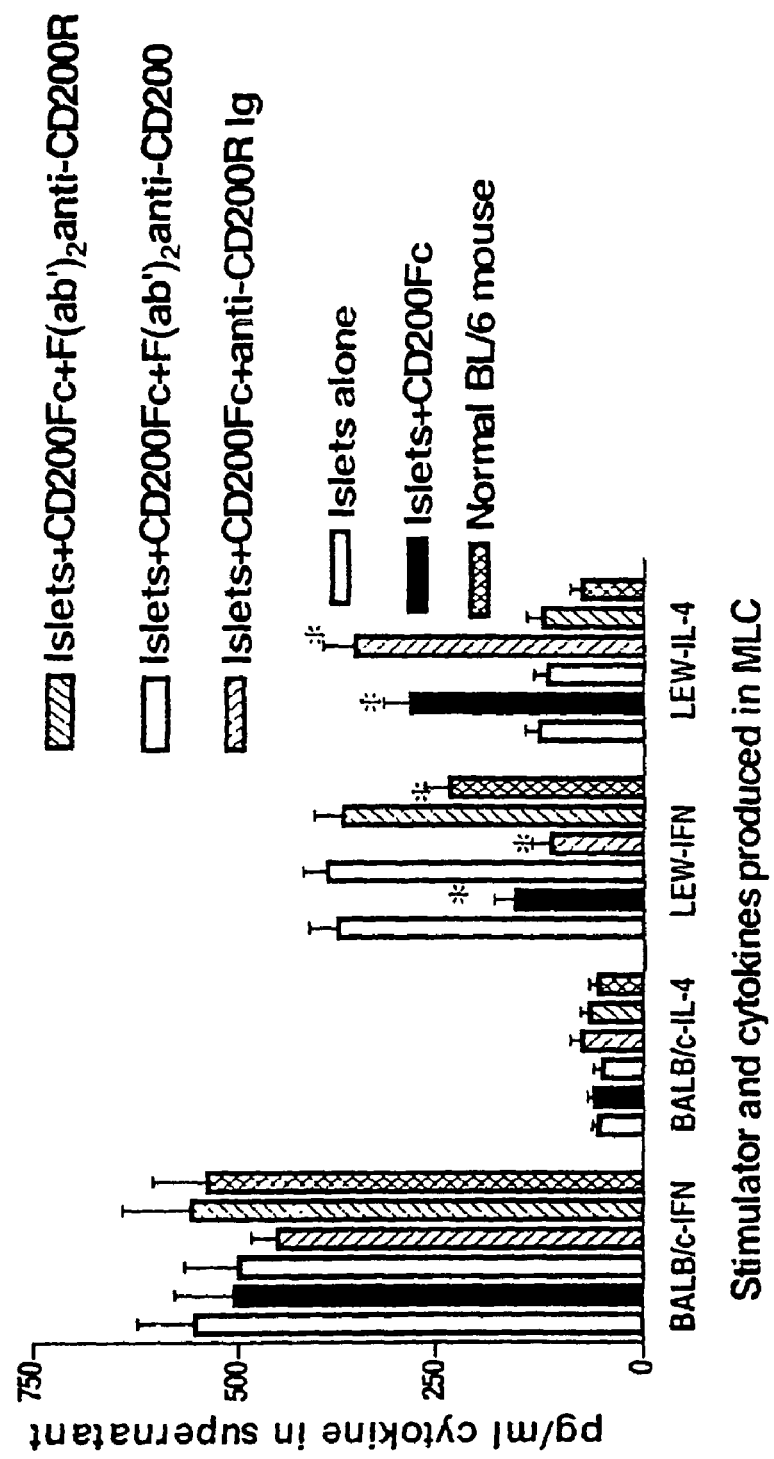
FIG. 22 is a graph showing CD200Fc and anti-CD200R Ig block type-2 cytokine production following xeno-islet transplantation under the kidney capsule.

As reported for allotransplants, CD200Fc and/or anti-CD200R Ig led to a marked decrease in generation of xenospecific CTL (panel a, FIG. 21), and decreased IFNγ production with increased IL-4 production after LEW restimulation in vitro (panel b, FIG. 21)—the latter are prototypic type-1 and type-2 cytokines respectively. Animals receiving islets alone, or islets with CD200Fc and F(ab')$_2$ anti-CD200 or F(ab')$_2$ anti-CD200R, produced LEW-specific CTL in vitro and type-1 cytokines. Restimulation with BALB/c splenocytes revealed that all of these changes were specific to the antigens expressed on transplanted tissue. Similar ELISA data were seen for IL-2 (equivalent to IFNγ) and IL-10 (equivalent to IL-4)-data not shown. Moreover, equivalent data to those reported in FIG. 21 were seen using pv infusion of islets, though in this case, even in the absence of CD200Fc, a control group with islets alone generated fewer LEW-specific CTL in vitro (7.4±2.1% lysis) and the cytokine profile also showed ~1:1 mixture of IFNγ and IL-4 (235±55 pg/ml)-data not shown. FIG. 22 is a graph showing CD200Fc and anti-CD200R Ig block type-2 cytokine production following xeno-islet transplantation under the kidney capsule.

Discussion

Figure 19:
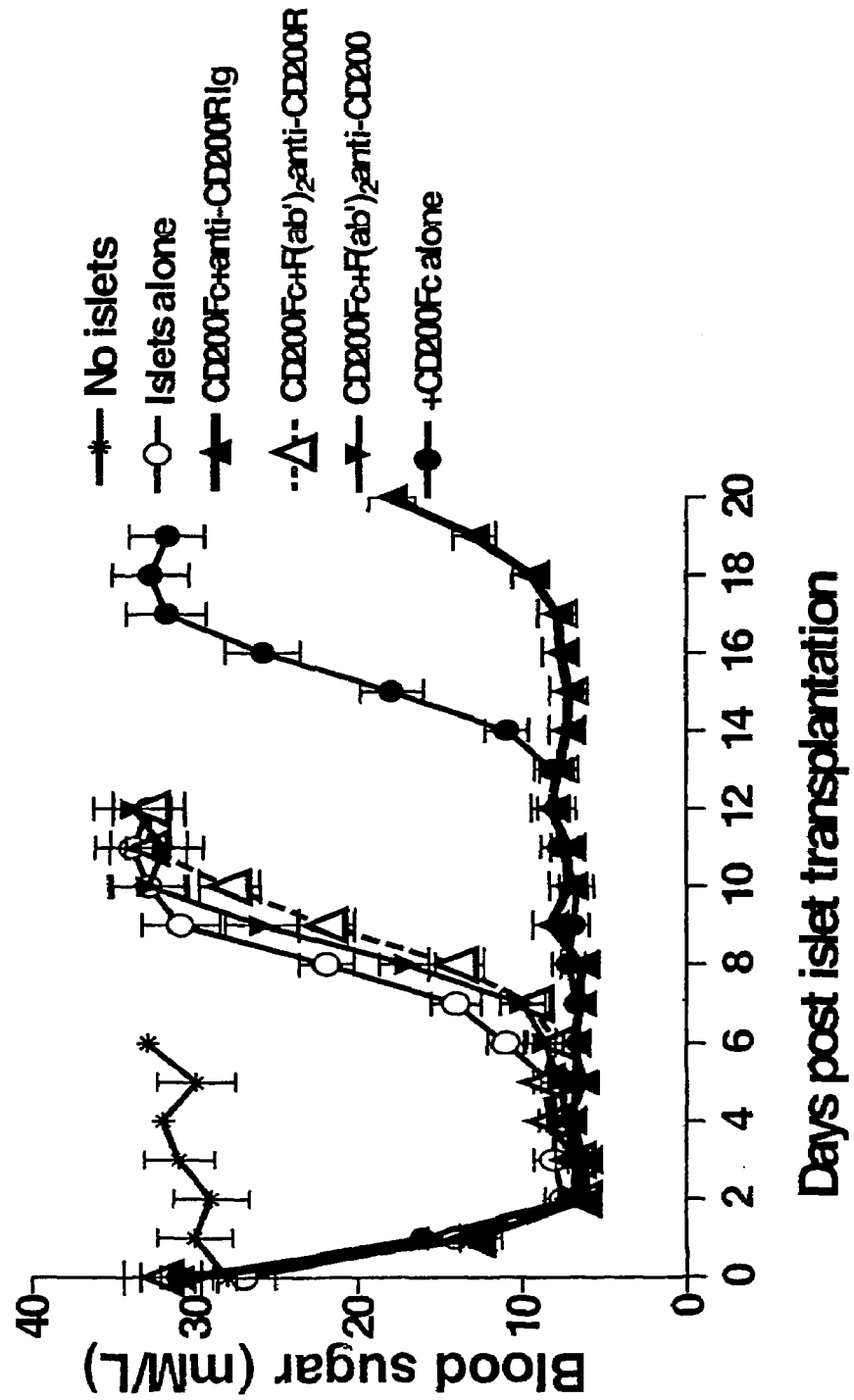
FIG. 19 is a graph showing anti-CD200R Ig (▲) synergizes with CD200Fc (●) in improving blood glucose control following xenoislet transplantation under the kidney capsule (p<0.05). In contrast, either F(ab')$_2$ anti-CD200 (▼) or F(ab')$_2$ anti-CD200R (Δ) blocks graft prolongation by CD200Fc (p<0.02). In these studies mice received a total of 5 injections of CD200Fc.
Figure 20:
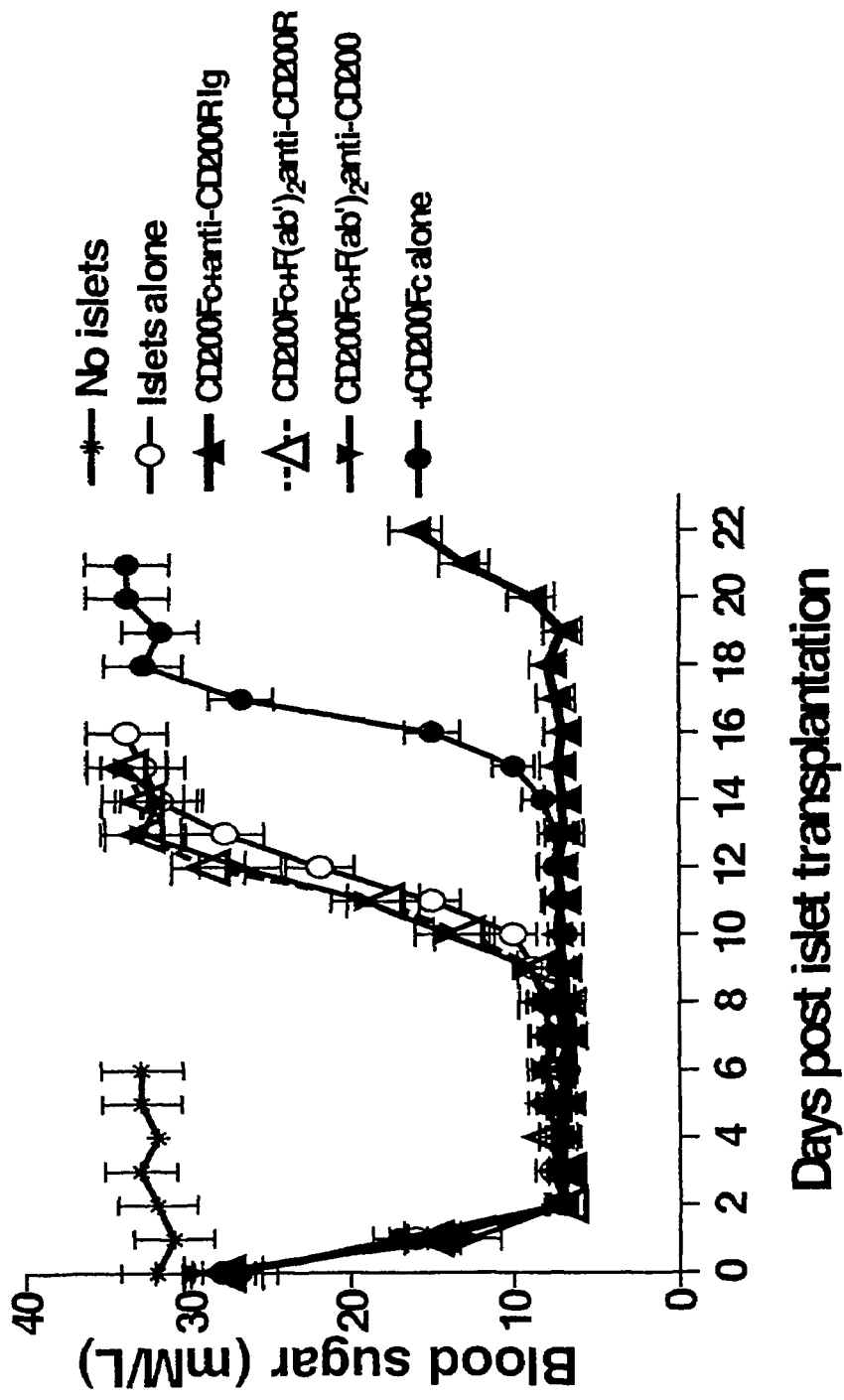
FIG. 20 is a graph showing anti-CD200R Ig (▲) synergizes with CD200Fc (●) in improving blood glucose control following xenoislet transplantation into the pv (p<0.05). In contrast, either F(ab')$_2$ anti-CD200 (▼) or F(ab')$_2$ anti-CD200R (A) blocks graft prolongation by CD200Fc (p<0.02); In these studies mice received a total of 5 injections of CD200Fc.

Using anti-CD200R Ig as immunosuppressant, the inventors have demonstrated the important role for CD200:CD200R interactions in rejection of rat islet grafts in mice (see FIGS. 19 and 20). The blocking data with F(ab')$_2$ anti-CD200 or F(ab')$_2$ anti-CD200R (FIGS. 19 and 20) is further confirmation of this interaction.

In conclusion, anti-CD200R antibody can play an important role in achieving prolongation of xenoislet survival in chemically diabetic animals transplanted via both the pv route, or receiving grafts under the kidney capsule. Graft prolongation is associated with decreased type-1 cytokine production, and loss of CTL specific for xenoantigen.

Example 7

Anti-CD200R Ameliorates Collagen-induced Arthritis in Mice

Summary

Immunization of DBA/1 with 100 mg bovine collagen type-II emulsified in Freund's Adjuvant, followed by booster injection in incomplete adjuvant at 18 days, leads to development of arthritis in more than 70% of mice by 28 days post injection. The inventors have previously shown that the novel immunosuppressant molecule CD200Fc (linking an extracellular domain of CD200 with a murine IgG2a Fc region) can suppress induction of disease when given to mice from the time of collagen injection. This occurs in concert with a decrease in the serum levels of anti-collagen IgG (~50% reduction), with relatively more IgG2b and IgG3, decreased serum levels of TNFα and IFNγ, and decreased production of those same cytokines after restimulation of lymphocytes in vitro with collagen. Since CD200 induces suppression following engagement of a receptor (CD200R), known to be expressed on, amongst other cells, macrophages, the inventors investigated whether infusion of anti-CD200R and/or CD200Fc would ameliorate established disease in DBA mice, when injections were begun following collagen immunization. The data indicate an arrest of disease following either treatment, with modification of a number of immune parameters (serum and lymphocyte cytokine production) consistent with a general role for CD200:CD200R interactions in the regulation of induction and/or expression of autoimmune disorders.

Materials and Methods

Animals:

8-week old DBA/1 mice (H2$^{q/q}$) were obtained from the Jackson Laboratories, Bar Harbour, Me., and kept 5/cage with food and water ad libitum. Mice were entered into experiments at 9 weeks of age.

Anti-CD200R Antibody and CD200Fc Immunoadhesin:

The rat mAb to mouse CD200R used in the studies described was characterized in Example 4. An immunoadhesin (CD200Fc) incorporating the extracellular domain of CD200 linked to a murine IgG2a Fc region was produced in a baculovirus systems, as described (1).

Collagen Induced Arthritis Model:

Arthritis was induced as described in a previous publication (90), injecting mice intradermally at the base of the tail with 100 μg bovine-collagen type-II (Sigma Chemical Co., St. Louis, Mo.) emulsified in Complete Freund's Adjuvant (CFA) in 100 ml 0.1M acetate. 18 days later animals received a further injection of 100 μg emulsified in Incomplete Freund's Adjuvant (ICFA) intradermally. Individual animals were monitored daily for signs of arthropathy, which was scored independently by 2 investigators for each limb on a 4-point scale as follows:

0=No paw swelling
1=Paw+a single joint
2=Paw+multiple joints (of the same limb)
3=Joint rigidity The total score/mouse was recorded (maximum=12). As discussed earlier (90) the correlation between total scores for investigators >0.93; scores recorded were thus arithmetic means of the 2 scores for each animal.

Where mice received anti-CD200R or CD200Fc, 100 µg or 15 µg/mouse respectively was infused iv in 200%1 PBS at 3 day intervals into 7 mice/group, beginning either on the first day of collagen immunization (t0) or at days 15 (t15) or 24 (t24) post immunization (see Figures). Control (7) mice received instead injections of 100 µg of pre-immune rat serum or 15 µg of normal mouse immunoglobulin (pooled from the serum of five 8-week normal DBA/1 mice). Further control groups (7 mice) received no additional treatment.

Antigen Stimulation In Vitro and Cytokine Assays:

Pooled peripheral lymph node (PLN) cells (axillary and inguinal nodes), as well as spleen cells, were harvested from individual mice at 35 days following immunization with collagen. Blood was also collected from individual animals by cardiac puncture, and serum obtained following centrifugation (14,000 rpm for 15 min) after overnight incubation at 4° C. Spleen and PLN cells were cultured in triplicate in microtitre plates ($1 \times 10^6$ cells/well in 300 µl of α-Minimal Essential Medium with 10% fetal calf serum, αF10) in the presence or absence of 20 µg/ml bovine collagen type-II. A further set of control cultures was stimulated with $5 \times 10^5$/well mitomycin-C treated (100 µg/ml, 45 min at 37° C.) BALB/c allogeneic spleen stimulator cells.

Culture supernatants (150 µl) were harvested at 40 hrs of culture and assessed for TNFα and IFNγ levels using an ELISA assay and commercial cytokine-specific mAbs obtained from Pharmingen (San Diego, Calif.). Plates precoated with 100 ng/ml R4-6A2 and developed with biotinylated XMG1.2 were used to assay IFNγ, and those precoated with G281-2626 and developed with biotinylated MP6-XT3 were used to assay TNFα. Streptavidin-coupled alkaline phosphatase with appropriate substrate was used to develop the assay, and recombinant mouse cytokines (Endogen, San Diego, Calif.) were used to quantitate the assay.

In addition to analyzing cytokines, proliferation of collagen (and allo)-stimulated cells was assessed by addition of 1 µCi $^3$HTdR at 72 hrs to each microtitre well (see above), and harvesting the wells for counting in a well-type β-counter at 14 hrs. All assays were performed in triplicate, with cultures containing unstimulated responder cells only serving as an appropriate control.

Measurement of Serum Anti-Collagen Type-II Antibody Isotypes:

Serum anti-collagen type-1 levels were determined by ELISA, as described in a previous publication (90). Serial 3-fold dilutions of the sera of collagen-immunized mice (obtained at 35 days post immunization as described above) were added to plates precoated with 100 µl of 1 µg/ml collagen type-II. After incubation (×3 hrs at 4° C.) and washing, plates were developed with isotype-specific biotinylated rat mAbs to mouse IgM, IgG1, IgG2a/2b and IgG3, followed by streptavidin-alkaline phosphatase and use of appropriate substrate. All ELISA reagents were purchased from Cedarlane Labs, Homby, Ontario, Canada. Purified mAb were used to standardize assays in order to calculate antibody levels. Total IgG levels were determined after adherence of serum to plates coated with poly-L-lysine (100 ng/ml), and developing with polyspecific biotinylated rat anti-mouse IgG.

Statistical Analysis:

Arthritic scores in different groups were compared by Mann-Whitney U-tests. Proliferation in, and cytokine production from, cells of all groups were initially analysed for differences by ANOVA. Thereafter pair-wise comparison of different groups was performed by Student's t-test.

Results

Murine CD200Fc or Rat Antibody to CD200R Ameliorates Arthritis after Collagen Immunization In order to examine the effect of anti-CD200R or CD200Fc fusion protein on immunomodulation of collagen-induced arthritis in mice the following study was performed. Groups of 7 mice were immunized with collagen intradermally, followed by booster immunization 18 days later. Animals received iv injections of either PBS, 15 µg/mouse of normal mouse Ig or CD200Fc, or 100 µg of anti-CD200R or preimmune rat serum (shown as preimmune Ig in subsequent Figures), beginning either on the day of initial immunization (t0) or at days 15 (t15) or 24(t24) post immunization, and continuing at 3 day intervals thereafter. Arthritic scores were assessed for all limbs as described in the Materials and Methods. Data in FIGS. 23 and 24 are taken from one of 2 studies of this type, and show the mean (±SEM) for each the different groups, in studies using CD200Fc (FIG. 23) or anti-CD200R (FIG. 24) respectively.

Figure 23:
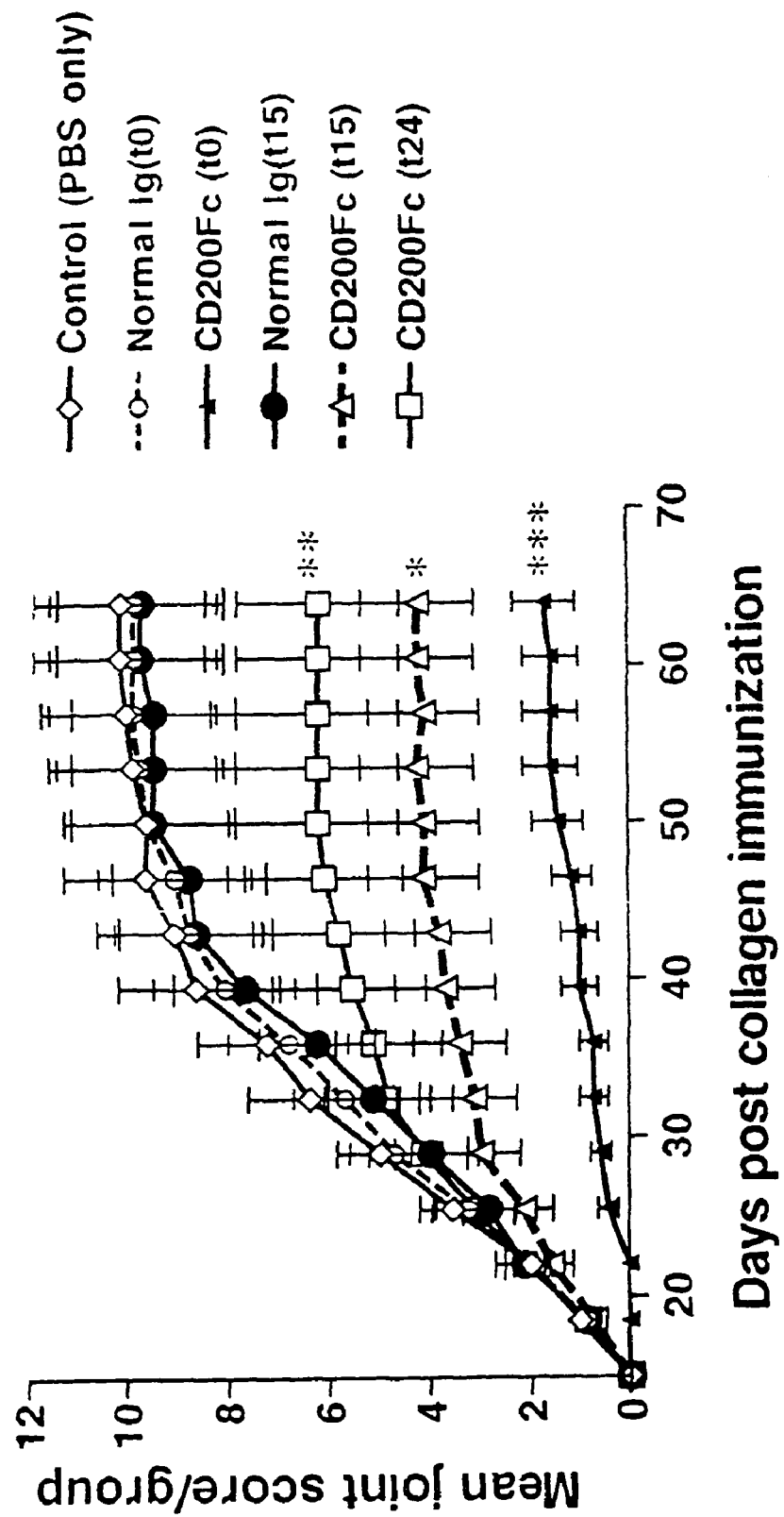
FIG. 23 is a graph that shows delayed injection of CD200Fc reduces severity of collagen-induced arthritis in mice. Groups of 7 DBA/1 mice were immunized with bovine collagen type-II in CFA, followed by reimmunization at day 18 with collagen in ICFA. Thereafter mice received 15 mg iv of normal mouse Ig or CD200Fc, at 3 day intervals, beginning at day 0 (t0) or at 15 (t15) or 24 (t24) days following initial collagen immunization. Scoring of disease in individual mice was as described in the Materials and Methods. Data are group arithmetic means (+SEM) of 7 scores/group at each time point. *, p<0.02; ,p<0.05; *,p<0.005.

These data confirm our previously published finding that treatment with CD200Fc from the time of immunization inhibits development of arthritis in this model (▼ in FIG. 23, p<0.005, Mann Whitney U-test), and extends this observation to show that anti-CD200R from the time of immunization also produces the same effect (▼ in FIG. 23). More importantly, even when infusion of either CD200Fc or anti-CD200R was delayed until days 15 or 24 post immunization with collagen (Δ and □ in FIGS. 23 and 24), there was a significant amelioration of disease compared with control mice (p<0.02 or <0.05 respectively in each Figure, Mann-Whitney U-test), suggesting that either treatment can modify not only induction of disease but disease expression.

Inhibition of Sensitization to Collagen in CD200Fc- or Anti-CD200R-Treated Mice

Figure 24:
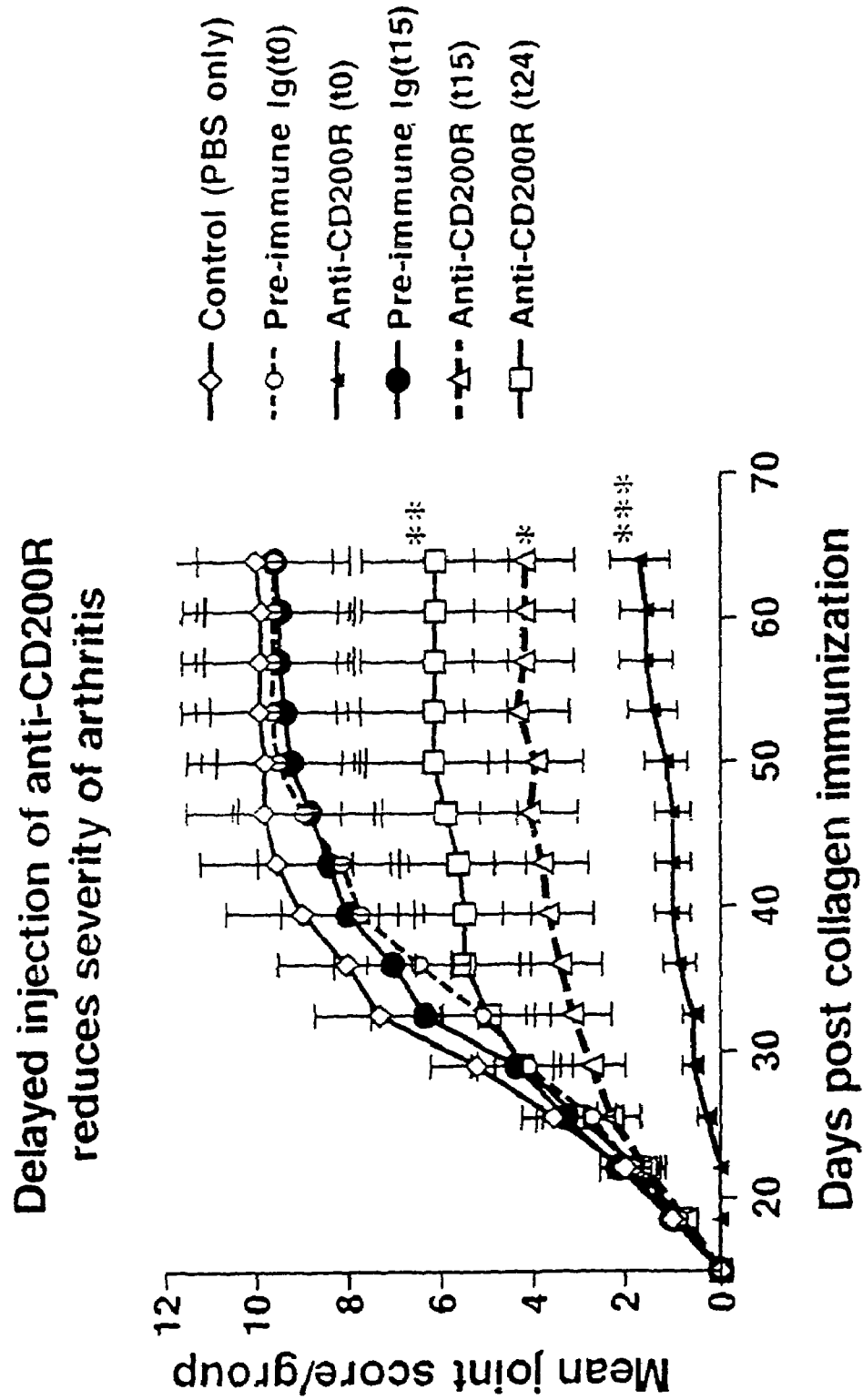
FIG. 24 is a graph that shows delayed injection of anti-CD200R antibody reduces severity of collagen-induced arthritis in mice. Data are as for FIG. 23, except that instead of CD200Fc (or normal Ig), 100 mg/mouse/injection of anti-CD200R (or preimmune serum) was used. Data are again group arithmetic means (±SEM) of 7 scores/group at each time point. *, p<0.02; ,p<0.05; *,p<0.005.
Figure 25:
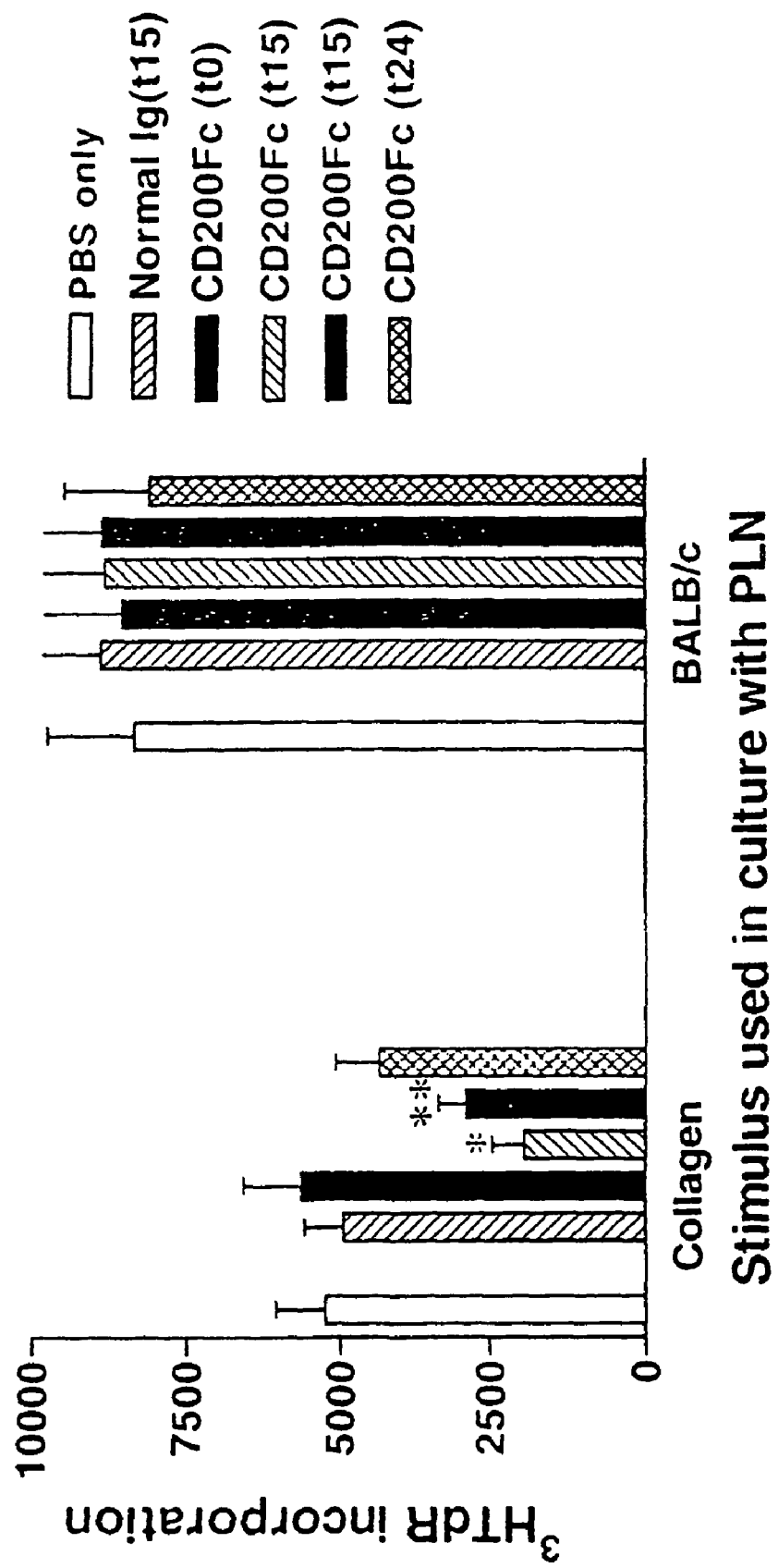
FIG. 25 is a bar graph that shows $^3$HTdR incorporation in peripheral lymph node (PLN) cells harvested from 4 mice/group, treated as shown in FIG. 23, after restimulation with collagen or BALB/c spleen stimulator cells. Background proliferation in cells from all groups without stimulation was in the same range (1250+450 cpm). *, p<0.02; **,p<0.05.
Figure 26:
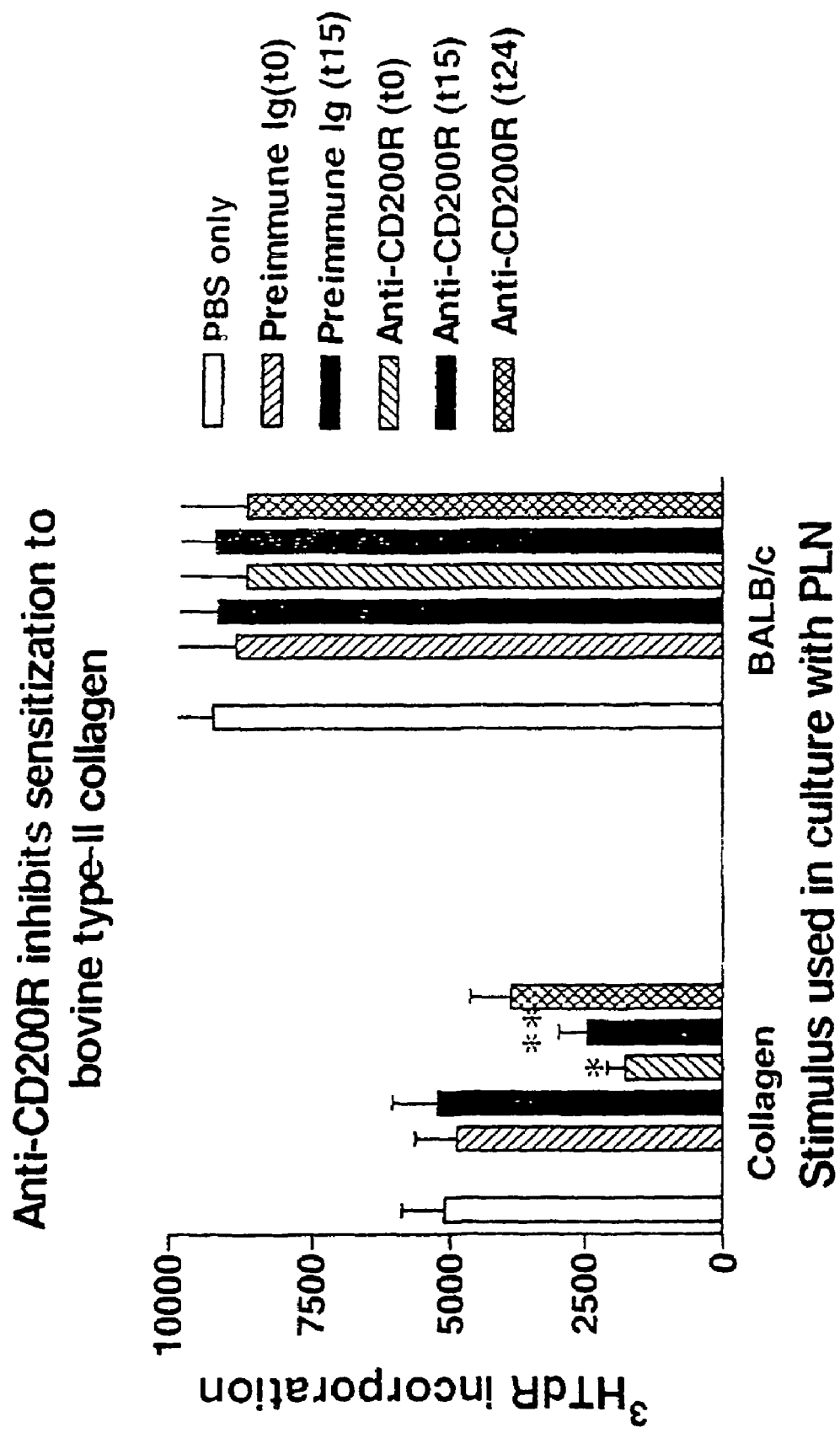
FIG. 26 is a bar graph that shows $^3$HTdR incorporation in PLN cells harvested from 4 mice/group, treated as shown in FIG. 24, after restimulation with collagen or BALB/c spleen stimulator cells. Background proliferation in cells from all groups without stimulation was in the same range (1190±405 cpm). *, p<0.02; **,p<0.05.

Data in FIGS. 25 and 26 show the proliferation in PLN taken at 35 days in separate studies using mice treated as shown in FIGS. 23 and 24, after restimulation of cells for 72 hrs in vitro with collagen or BALB/c spleen cells. 4 mice were used/group, and cells were assayed from individual mice-data show group means for the 4 mice. As reported earlier, treatment with CD200Fc from the time of initial immunization (to) inhibits specific sensitization to collagen as assessed by subsequent proliferation in response to collagen stimulation (p<0.02 with respect to all other groups)-this effect was mimicked by infusion of anti-CD200R from the time of immunization (FIG. 26). No effect was seen on proliferation in response to BALB/c cells in any group tested. Interestingly, infusion of CD200Fc or anti-CD200R from day 15 post primary immunization (t15), which corresponds to 3 days before boosting with collagen in Incomplete Freund's Adjuvant (see Materials and Methods), led to a similar specific inhibition of proliferation in response to collagen restimulation (p<0.05). In contrast, commencing infusion of CD200Fc or anti-CD20R from day 24 after primary immunization led to minimal effects on proliferation. Similar data to the above were seen using splenic lymphocytes from these donors (not shown), and for PLN in a separate repeat experiment.

Decrease in Serum Levels of TNFα and IFNγ in Collagen Sensitized Mice Following Delayed Injection of CD200Fcor Anti-CD200R At the time of sacrifice of mice shown in FIGS. 25 and 26 serum was collected for assay of the cytokines TNFα and IFNγ, which have been implicated in the inflammatory processes responsible for pathophysiology in arthritis, and shown in earlier work to be elevated in the CIA model used (90). Data shown in FIGS. 27 and 28 indicate that CD200Fc or anti-CD200R injection reduces or prevents the increase in serum TNFα and IFNγ levels seen in mice with arthritis provided infusion of these reagents was begun before day 15 post initial collagen immunization. Delay of infusion to 24 days post immunization led to minimal suppression of serum cytokine levels. Similar data were obtained in a repeat study.

Figure 27:
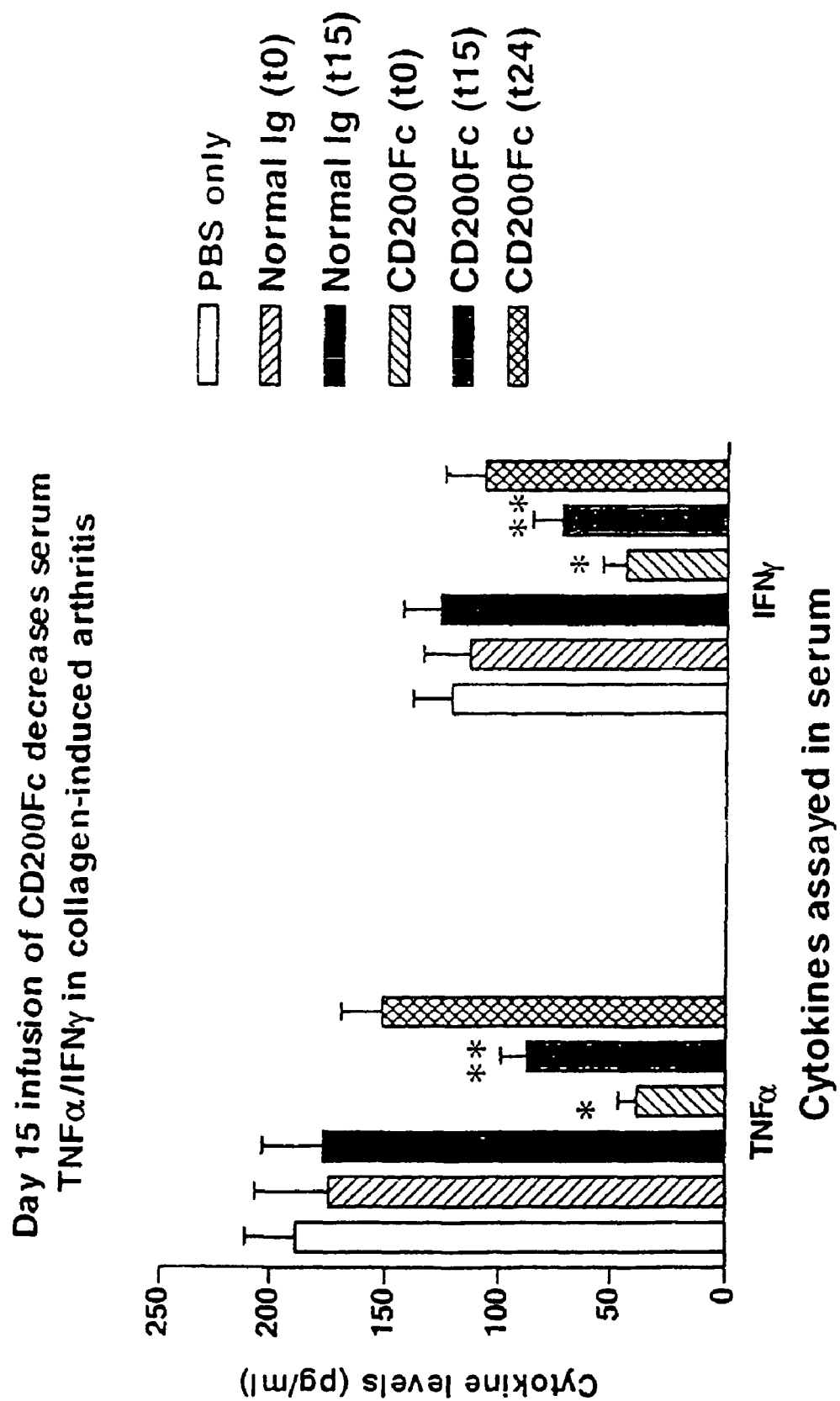
FIG. 27 is a bar graph that shows the delay of infusion of CD200Fc to day 15 post initial collagen immunization still results in inhibition of increased serum TNFα and IFNγ in collagen-immunized. Groups were treated as described in FIG. 25. Data represent arithmetic means (+SD) for 4 mice/group. Background serum TNFα and IFNγ cytokine levels (pg/ml) in a group of 5 normal DBA/1 mice (non-immunized) was 30±8.5 and 35±10 respectively. *, p<0.02; **,p<0.05.
Figure 28:
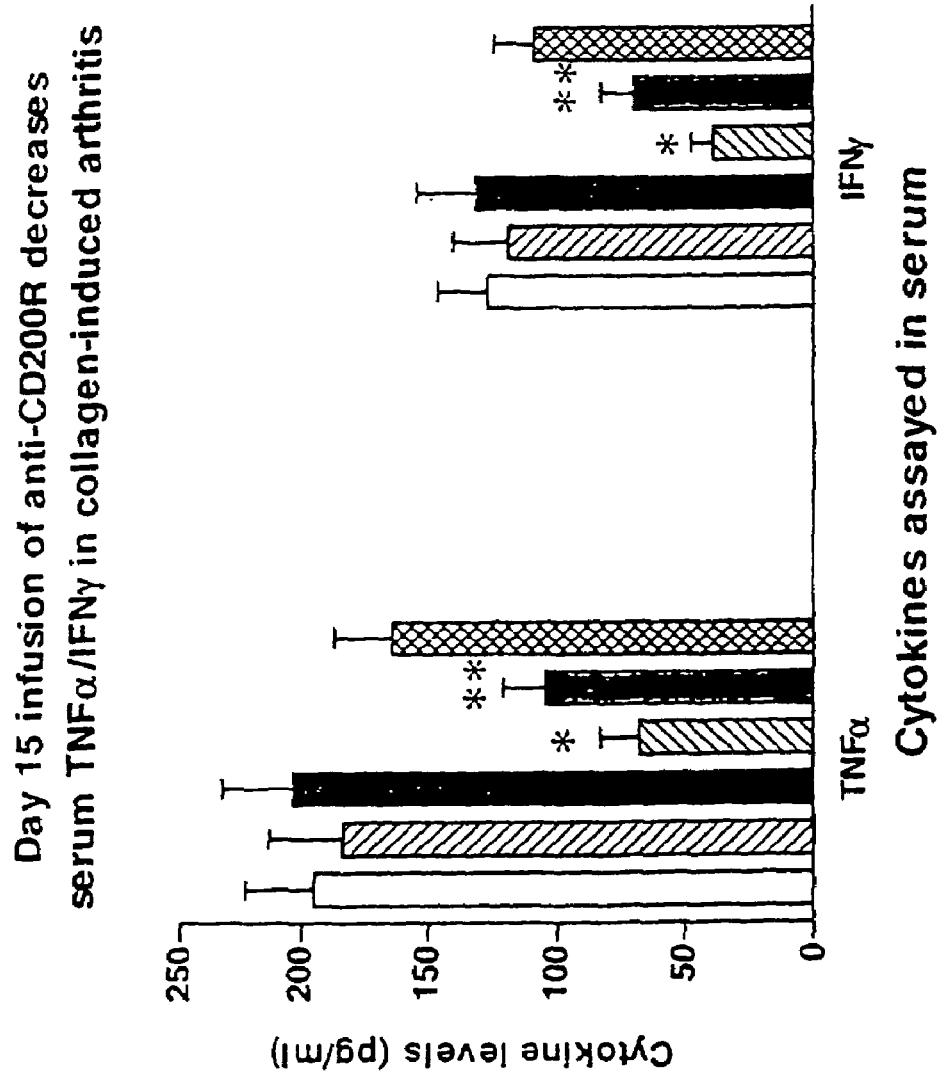
FIG. 28 is as for FIG. 27, except that anti-CD200R antibody was used instead of CD200Fc (see FIGS. 24-27). Once again data represent arithmetic means (±SD) for 4 mice/group-control serum levels in non-immunized mice were as described in the legend to FIG. 27. *, p<0.02; **,p<0.05.
Figure 29:
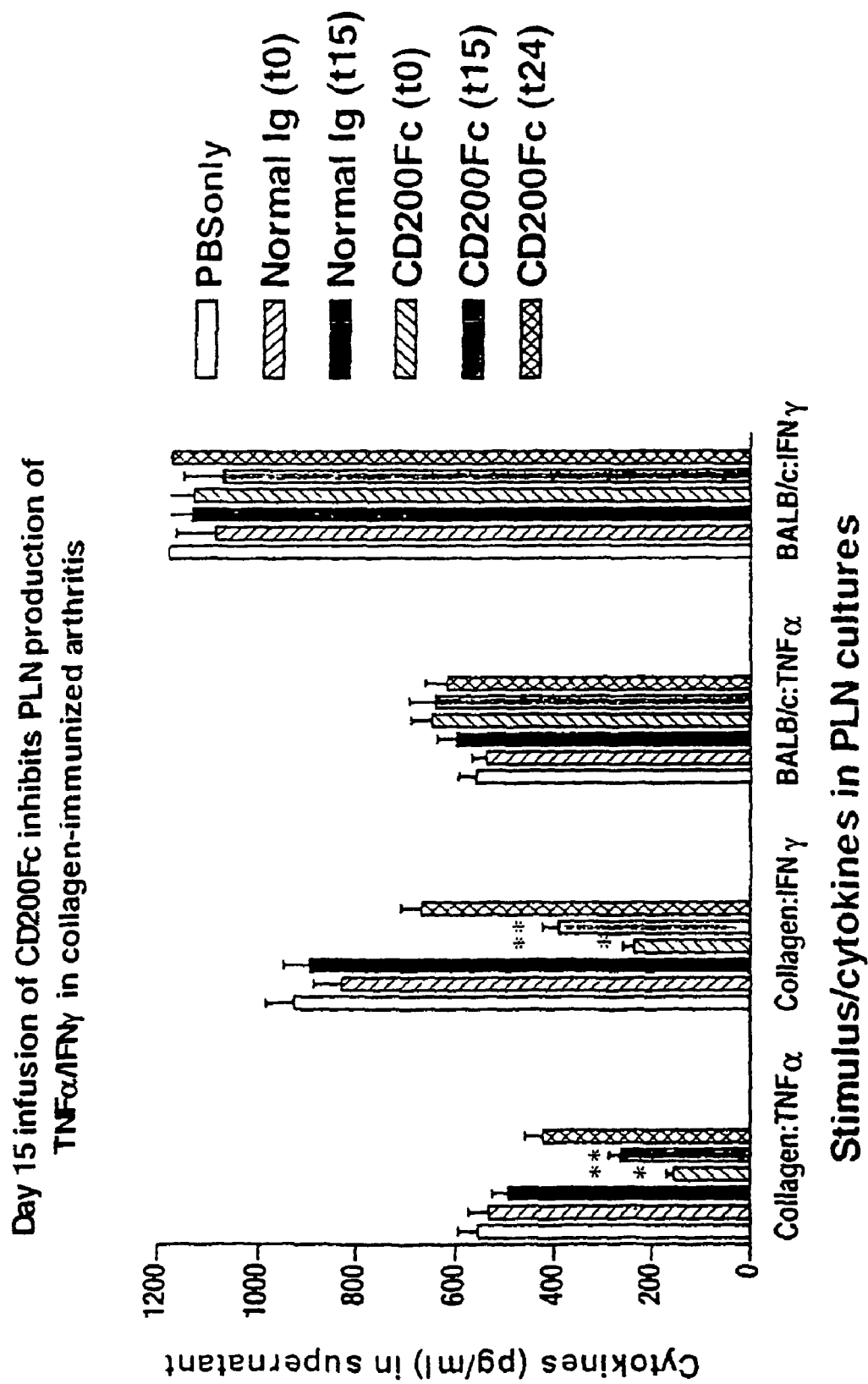
FIG. 29 is a bar graph that shows inhibition of sensitization for TNFα and IFNγ production in PLN cells of mice immunized with collagen and treated with CD200Fc at various times thereafter. See Materials and Methods and legends to FIGS. 21, 25 and 27 for more details. Groups were stimulated as in FIG. 25 with either collagen or BALB/c cells and cytokines assayed in the supernatants at 40 hrs. Control cytokine production, averaged over all groups in the absence of stimulation, for TNFα/IFNγ was 60±20 and 100±25 pg/ml respectively. *, p<0.02; **,p<0.05.
Figure 30:
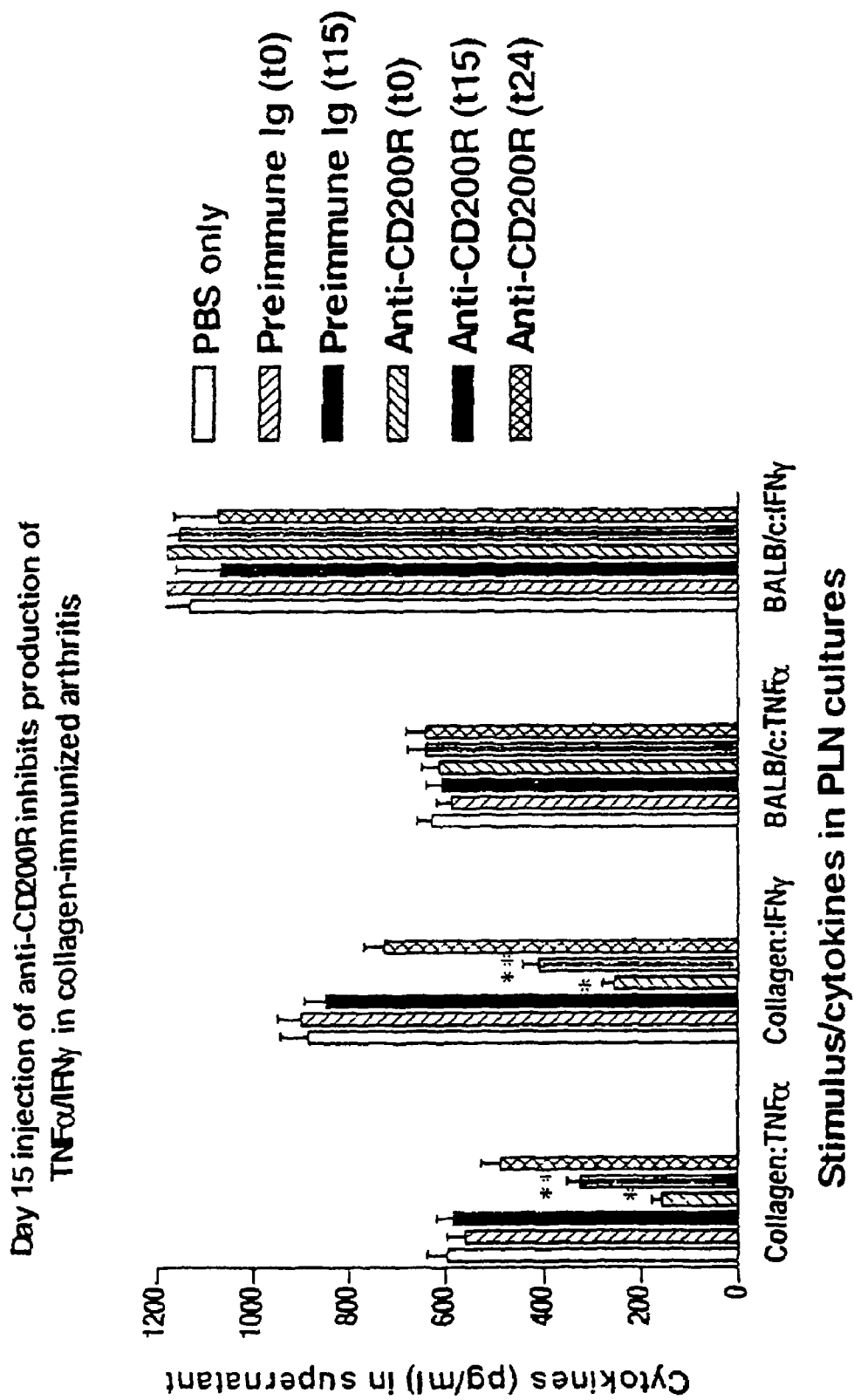
FIG. 30 is as for FIG. 29, except that mice were treated with anti-CD200R, not CD200Fc, beginning at various times post collagen immunization. See Materials and Methods and legends to FIGS. 24, 26 and 28 for more details. Control cytokine production (no stimulation) for TNFα/IFNγ was 70±25 and 95±30 pg/ml respectively. *, p<0.02; **,p<0.05.

Inhibition of Production of TNFα and IFNγ in Cells of Collagen-sensitized Mice Following Delayed Injection of CD200Fc or Anti-CD200R Data shown in FIGS. 29 and 30 are analogous to those of FIGS. 27 and 28 except that in this case cytokine production was assayed in the supernatant of cultures from the individual mice (whose proliferative capacity was detailed in FIGS. 25 and 26). Once again injection of CD200Fc or anti-CD200R, even at 15 days post collagen immunization, clearly led to inhibition of TNFα and IFNγ production from restimulated cells, in a collagen-specific fashion (no inhibition was seen when restimulation was with BALB/c cells). No inhibition was seen when infusion of either CD200Fc or anti-CD200R was delayed to 24 days post immunization (see also FIGS. 25-28). Similar data to the above were seen using supernatants from splenic lymphocytes from the same donors (not shown), and for supernatants derived from PLN cells in a separate repeat experiment.

Figure 31:
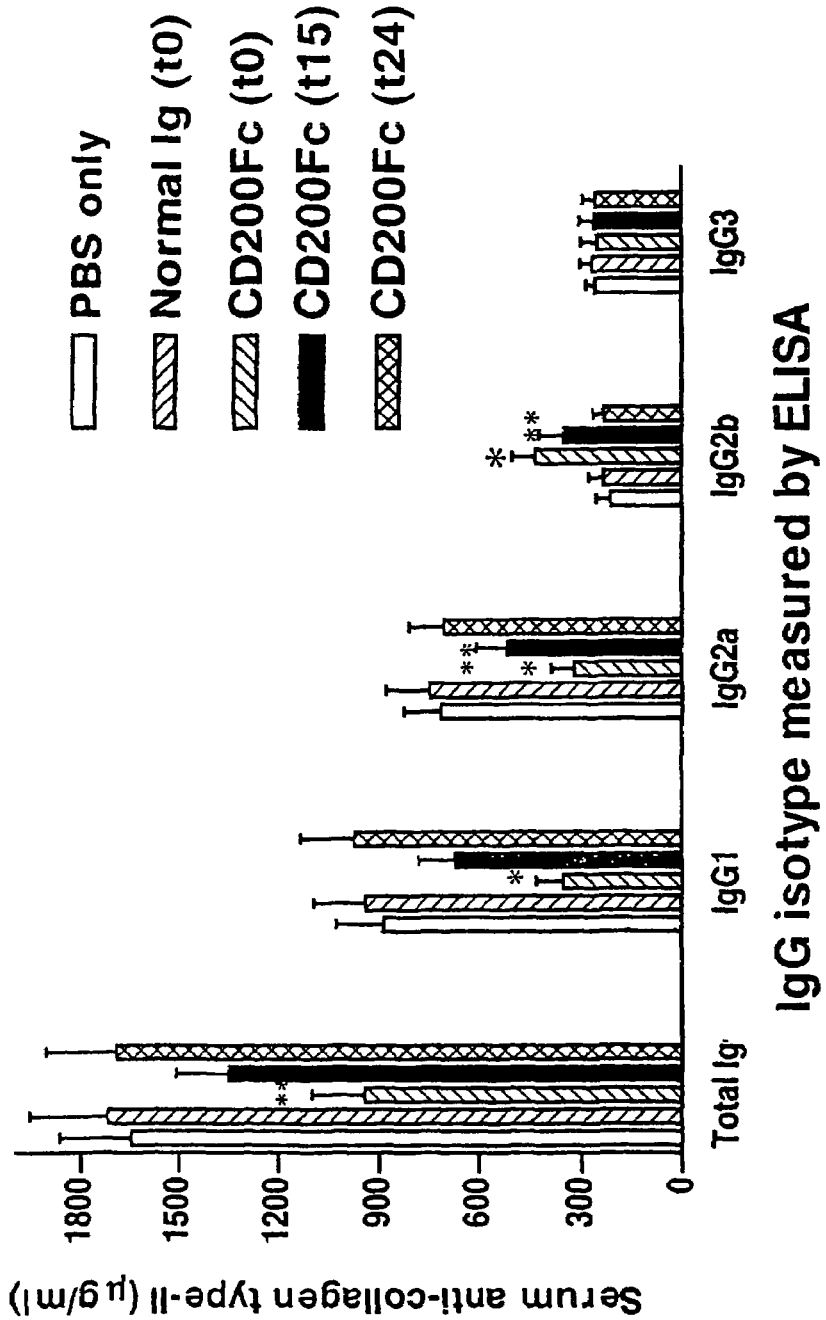
FIG. 31 is a bar graph that shows CD200Fc alters quantitative and qualitative production of autoantibody to collagen type-II in treated mice, even when begun 15 days following primary immunization with collagen. Data show total serum IgG and different IgG isotype levels at 36 days of sacrifice in the groups of mice documented in FIGS. 25, 27 and 29. All data points represent arithmetic means (±SD) of 4 mice/group. Similar data were obtained in a repeat study. *, p<0.02; **,p<0.05.
Figure 32:
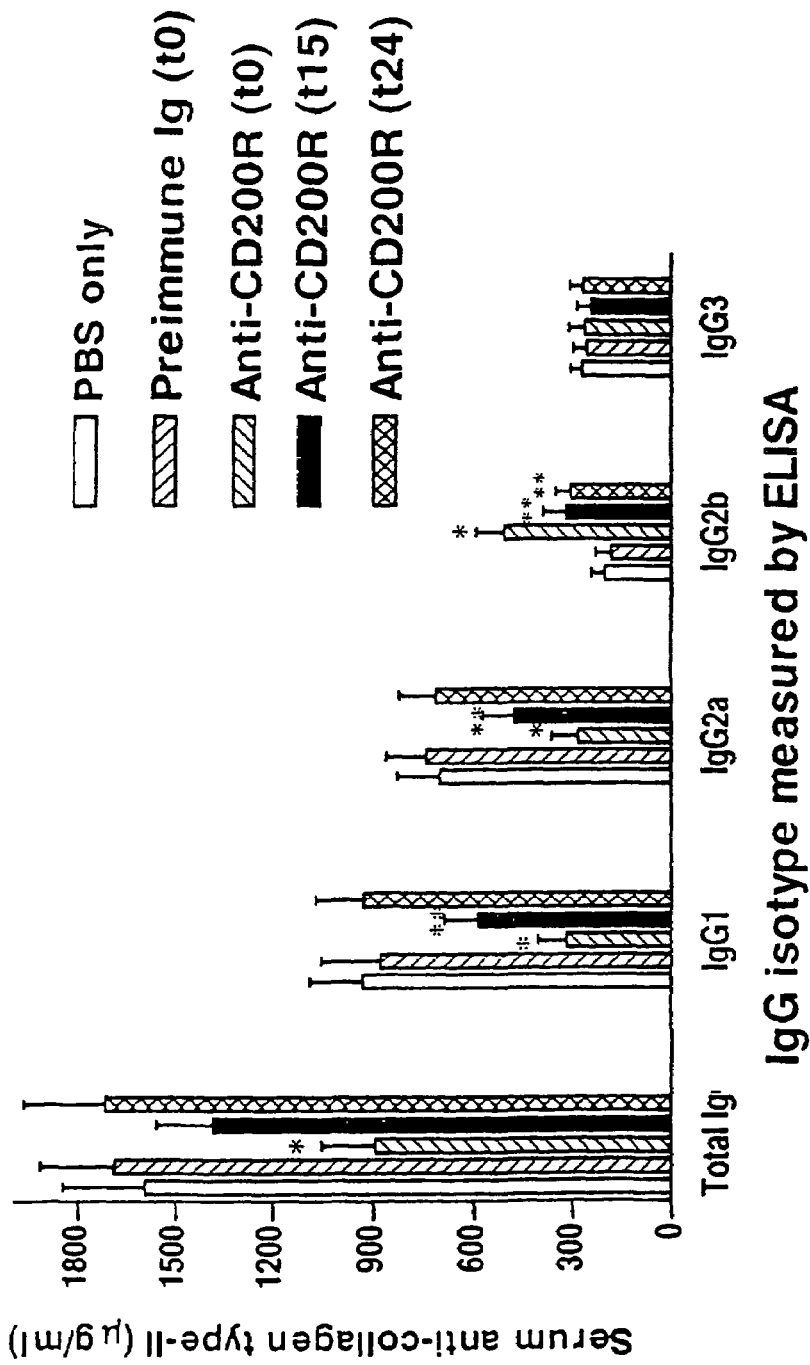
FIG. 32 is for FIG. 31, except that anti-CD200R was used to modulate antibody production rather than CD200Fc. Data show total serum IgG and different IgG isotype levels at 36 days of sacrifice in the groups of mice documented in FIGS. 26, 28 and 30. All data points represent arithmetic means (±SD) of 4 mice/group. Similar data were obtained in a repeat study. *, p<0.02; **,p<0.05.
Figure 33:
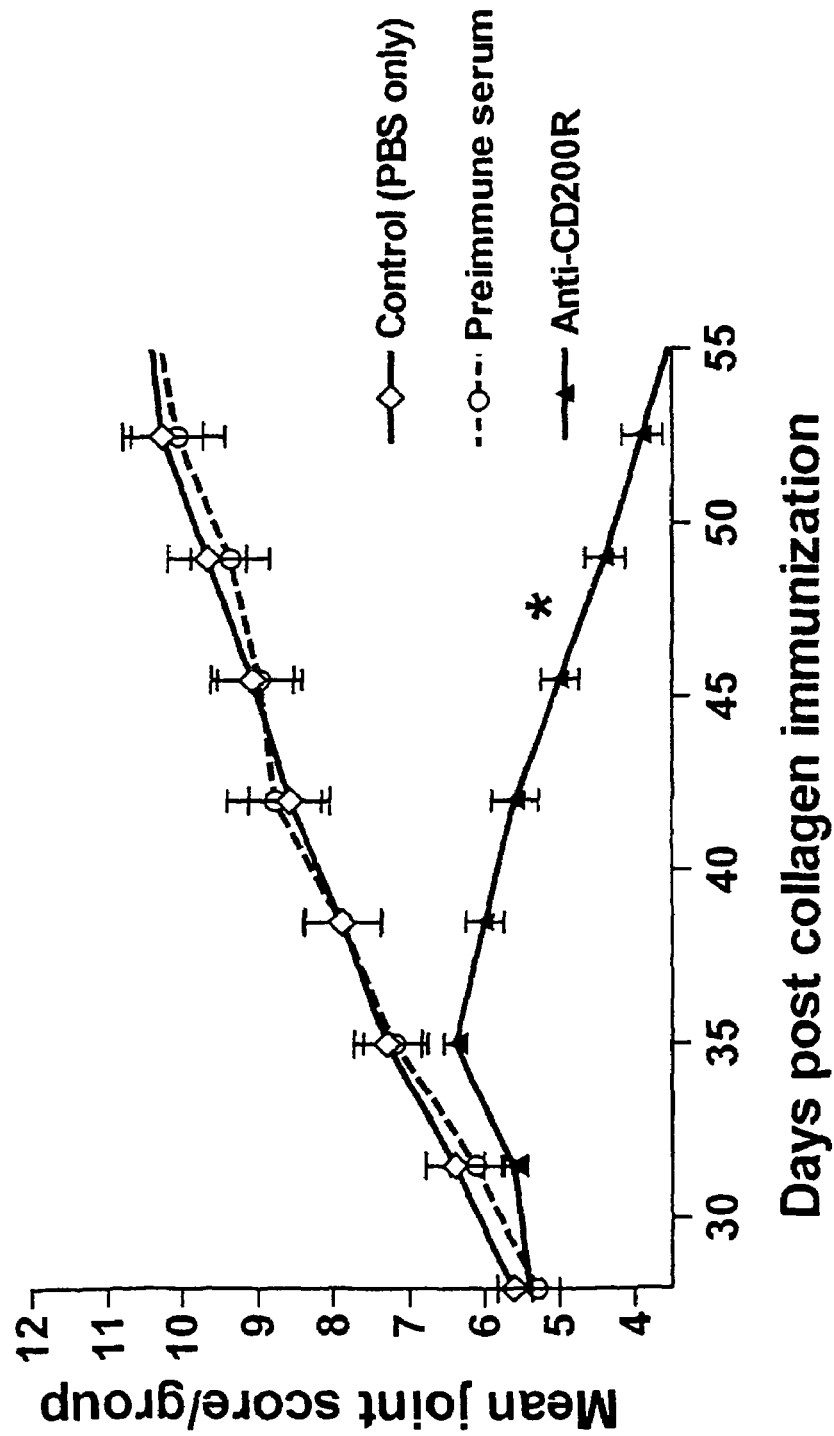
FIG. 33 is a graph showing injection of 250 µg/mouse anti-CD200R antibody reduces severity of disease in overtly arthritic mice. Data are as for FIGS. 23 and 24, except that infusions of PBS, anti-CD200R or preimmune sera were begun only 28 days after collagen immunization, and continued at 3.5 day intervals over the following 4 weeks. Data show group arithmetic means (±SEM) of 10 scores/group at each time point. *,p<0.05.

Effect of Delayed Injection of CD200Fc or Anti-CD200R on Production of Anti-collagen Antibodies In a previous study the inventors reported that treatment with CD200Fc from the time of collagen immunization decreased total anti-collagen IgG levels (by ~50%), with a concomitant shift in isotype profiles, with significantly less IgG1 and IgG2a, and more IgG2b, relative to Ig isotype production in control mice (90). Data shown in FIGS. 31 and 32 are derived from one of two studies analyzing the isotype profile of anti-collagen antibodies in day 36 sera from the groups of mice described in the studies above (see FIGS. 23-30). While there was no difference in total IgG levels in the different groups (data not shown: mean levels 11.0±3.4 mg/ml across all groups), it is evident that infusion of CD200Fc from the initial time of immunization reduces anti-collagen antibody, as reported earlier (89), an effect mimicked by infusion of anti-CD200R from the time of immunization (FIG. 33). Commencing infusion of anti-CD200R or of CD200Fc from day 15 post immunization produced a lesser diminution in total anti-collagen Ig (see Figures). However, whether CD200Fc or anti-CD200R was started at day 0 or 15 days post immunization with collagen, each agent produced a clear change in anti-collagen isotype profiles, with decreased IgG1 and IgG2a, and elevated IgG2b relative to control injected mice. In animals where injection of CD200Fc or anti-CD200R was delayed until 24 days post collagen immunization there was no significant change in anti-collagen isotype production, despite the evidence (see FIGS. 24 and 25) for amelioration of disease.

Rat Antibody to CD200R Ameliorates Established Arthritis in Mice after Collagen Immunization In order to examiner the effect of anti-CD200R on modulation of established disease in the collagen-induced arthritis model described, the following study was performed. A group of 40 mice was immunized with collagen intradermally, followed by booster immunization 18 days later. Beginning at 28 days post immunization with collagen, at which stage the mean score across all arthritic mie was 5.5±0.5, 30 arthritic animals were randomly allocated to groups of 10. These received iv injections of either PBS, or 250 µg of anti-CD200R or the preimmune rat serum (from rats used to produce the anti-CD200R mAb) at 3.5 day intervals, throughout the following 4 weeks. Arthritic scores were assessed for all limbs as described in the Materials and methods. Data in FIG. 33 are taken from one of 2 studies of this type, and show the mean (±SEM) for each of these three groups. It is clear from these data that infusion of anti-CD200R, even into overtly arthritic mice, significantly decreases the arthritic score in such mice (highest mean score seen/group (at 38 days) 6.3±0.3; mean score after 4 weeks of treatment, 4.1±0.3; reduction in disease ~50%).

Discussion

The results in the present Example provide evidence that in addition to CD200Fc, cross-linking antibodies to CD200R can also prevent collagen induced arthritis (CIA) when administered from the time of collagen immunization. The immunological changes previously seen following infusion of CD200Fc which were associated with inhibition of disease (decreased serum TNFα and IFNγ; decreased proliferation and TNFα/IFNγ production after collagen restimulation in vitro; altered serum anti-collagen Ig isotype production were also seen after infusion of anti-CD200R from the time of immunization. However, the current data add another important observation, namely that both CD200Fc and anti-CD200R antibody can produce these immunological changes, albeit in somewhat muted form, even when given 15 days following collagen administration. Moreover, objective disease, as assessed by an arthritic joint score, is ameliorated even when infusion of either CD200Fc or anti-CD200R is withheld until 24 days following immunization, at which time arthritis is first manifest in treated mice (see FIGS. 23 and 24 and 33).

Example 8

Induction of Tolerance-inducing Antigen-presenting Cells in Bone Marrow Cultures In Vitro Using mAbs to CD200R In this Example, C57BL/6 bone marrow cells were cultured in vitro in the presence of (IL-4+GM-CSF) to generate allostimulatory dendritic cells, which were in turn used to induce CTL and cytokine production after culture with C3H responder spleen cells. Inclusion of mAbs to different isoforms of CD200R in the bone marrow culture led to generation of cells which were unable to produce allostimulation in vitro with responder spleen cells. Instead, cells taken from these latter cultures contained a population of CD3$^+$ cells able to inhibit the antigen-specific MLC response of fresh C3H responder cells to stimulation with C57BL/6 cells, but not stimulation with BALB/c cells. In addition, these cells, infused in vivo into mice receiving C57BL/6 skin grafts, produced antigen-specific decreased rejection of BL/6 allografts, not BALB/c allografts, compared with mice receiving control cells (generated from bone marrow in the absence of anti-CD200R). The suppression induced in vitro using cells from the initial bone marrow cultures (derived in the presence of anti-CD200R) could be overcome in secondary MLCs by using limiting numbers of these cells, and an excess of allostimulatory cells derived from bone marrow cultures maintained in the absence of anti-CD200R. These data suggest that anti-CD200R biases stem cells in bone marrow towards development of suppressive antigen-presenting cells, which can be monitored in vitro and which have the potential to modify graft acceptance in vivo.

Materials and Methods

Mice: Male C57BL/6, C3H/HEJ and BALB/C mice were purchased from the Jackson laboratories, Bar Harbour, Me. Mice were housed 5/cage and allowed food and water ad libitum. All mice were used at 8-12 weeks of age.

Monoclonal antibodies: The following monoclonal antibodies (mAbs) were obtained from Pharmingen (San Diego, Calif., USA) unless stated otherwise: anti-IL-2 (S4B6, ATCC; biotinylated JES6-5H4); anti-IL-4 (11B11, ATCC; biotinylated BVD6-24G2); anti-IFNγ (R4-6A2, ATCC; biotinylated XMG1.2); anti-IL-10 (JES5-2A5; biotinylated, SXC-1); anti-IL-6 (MP5-20F3; biotinylated MP5-32C11); anti-TNFα (G281-2626; biotinylated MP6-XT3); FITC anti-Ia$^b$, FITC anti-CD11c, FITC anti-CD54, FITC anti-CD80, FITC anti-CD86, FITC anti-CD40, FITC anti-αβTCR, L3T4 (anti-mouse CD4), anti-CD3, anti-thy1.2 and anti-Ly2.2 were obtained from Cedarlane Labs, Hornby, Ontario. The hybridoma producing DEC205 (anti-mouse dendritic cells) was a kind gift from Dr. R. Steinman, and was directly labeled with FITC.

Rat anti-mouse CD200R1, anti-CD200R2 and anti-CD200R3 mAbs were prepared by ImmunoPrecise Labs (Victoria, BC, Canada), using KLH-coupled peptides synthesized by the American Peptide Co. (Sunnyvale, Calif., USA) and predicted to represent peptides unique to different CD200R isoforms (Example 2). The mAbs were characterized for recognition of CD200Rs by ELISA and by FACS analysis, using COS cells transfected with cDNAs encoding the various CD200Rs, in the same manner as was described in previous studies (103).

Strepavidin horse radish peroxidase and recombinant mouse GM-CSF was purchased from Pharmingen (San Diego, Calif.).

Preparation of cells: Single cell suspensions from different tissues were prepared aseptically by incubation of teased tissue in collagenase for 30 minutes at 37° C., and after centrifugation cells were resuspended in α-Minimal Essential Medium supplemented with 2-mercaptoethanol and 10% fetal calf serum (αF10). LPS splenic DC, stained (>90%) with DEC205, were obtained by overnight culture (1 g/ml LPS) of adherent fresh spleen cells.

Where DCs were obtained by culture of bone marrow cells in vitro the following technique was used (106). Bone marrow plugs were aspirated from the femurs of donor male C57BL/6 (or BALB/c) mice, washed and resuspended in αF10. Cells were treated sequentially with a mixture of antibodies (L3T4, anti-thy1.2, anti-Ly2.2) and rabbit complement and dead cells removed by centrifugation over mouse lymphopaque (Cedarlane Labs, Ontario). Cells were washed ×3 in αF10, and cultured in 10 ml αF10 in tissue culture flasks, at a concentration of 2×10$^6$/ml with 500 U/ml recombinant murine GM-CSF and rIL-4 (Pharmingen, USA). Fresh GM-CSF and IL-4 was added at 36 hr intervals. Cells were separated over lymphopaque on days 3 and 6 of culture, again reculturing in αF10 with recombinant GM-CSF. Where normal rat Ig or monoclonal rat anti-mouse CD200R mAb was added, the Ig was included in bone marrow cultures at a concentration of 2.5 µg/ml. At 8 days an aliquot of cells from all cultures was stained with NLDC-145 and FITC anti-rat IgG, and as control with FITC-anti-CD3. Mean staining with these antibodies in our hands using cells from all such cultures has been 95%±5% and <4% respectively, with no significant difference seen under any of these conditions. The remaining cells were washed, counted and used in MLC cultures or for injection into the tail vein of recipient C3H/HEJ mice which subsequently received skin grafts as described.

Skin Allotransplantation:

All procedures were performed as described earlier (107). Allogeneic skin grafts were obtained from donors of C57BL/6 or BALB/c origin. Mice received infusion of DCs immediately prior to skin grafts as described below.

Cytotoxicity and Cytokine Assays:

In allogeneic mouse mixed leukocyte cultures (MLC) used to assess cytokine production 1×10$^6$ responder cells were stimulated with 3×10$^5$ mitomycin-C treated (45 min at 37° C.) C57BL/6 or BALB/c DC stimulator cells (harvested from 10-day cultures as above) in triplicate in αF10. Where cytokine production was measured, supernatants were pooled at 40 hr from replicate wells and assayed in triplicate in ELISA assays for lymphokine production with capture and biotinylated detection mAbs as described above. Varying volumes of supernatant were bound in triplicate at 4° C. to plates pre-coated with 100 ng/ml mAb, washed ×3, and biotinylated detection antibody added. After washing, plates were incubated with strepavidin-horse radish peroxidase (Cedarlane Labs), developed with appropriate substrate and OD$_{405}$ determined using an ELISA plate reader. Recombinant cytokines for standardization were obtained from Pharmingen (U.S.A.). All assays showed sensitivity in the range 40 to 4000 pg/ml.

Where cytotoxicity was assayed, cells were harvested from MLC cultures at 5 days and titrated at different effector:target ratios for killing (4 hrs at 37° C.) of $^{51}$Cr-labeled P815 or EL4 tumor target cells.

Results

Failure to Induce CTL and Type-1 Cytokines Using DCs Harvested from Bone Marrow Cultures Incubated in the Presence of Anti-CD200R mAbs:

DCs were obtained from 8 day cultures of C57BL/6 bone marrow cells incubated in the presence of anti-CD200R1, anti-CD200R2, anti-CD200R3 or control rat Ig (each at 10 µg/ml) and used as stimulator cells for a pool of C3H responder spleen cells. Control DCs were obtained by overnight incubation of C57BL/6 spleen adherent cells. All DCs were incubated with mitomycin-C before use as stimulator cells. Cytokines and CTL were assayed in culture as described. Data from a typical study (one of three) are shown in FIG. 34.

It is clear from these data that while DCs obtained from spleen, or from 8 day cultures of bone marrow cells incubated in the presence of normal rat Ig, were capable of inducing CTL and type-1 cytokines (as monitored by IFNγ production) from allogeneic spleen cells, BM-derived DCs from cultures containing the different anti-CD200Rs were unable to do so. Instead, these latter DCs preferentially induced IL-10 from allogeneic spleen cells. The anti-CD200R1 and —R2 antibodies tested showed relatively greater inhibition than that shown by anti-CD200R3. While all mAbs have been used in the experiments to be described below, with comparable results, in all subsequent studies only data for anti-CD200R2 are shown.

Figure 34:
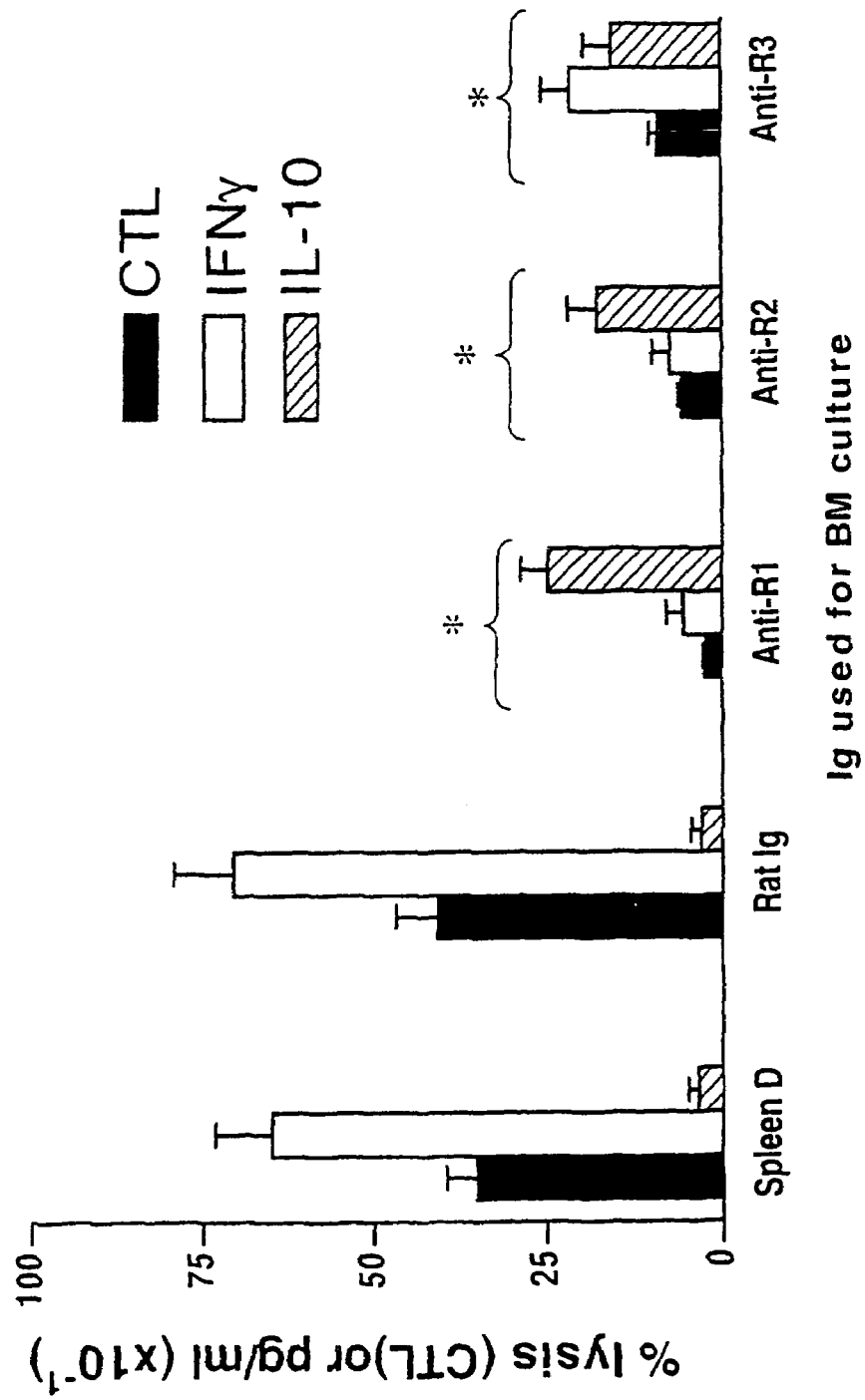
FIG. 34 is a bar graph showing failure to stimulate CTL or IFNγ from C3H spleen cells in MLCs using either splenic (far left histograms) or bone-marrow derived DCs. The latter were obtained from cells cultured in the presence of normal rat Ig or anti-CD200R mAbs (anti-CD200R1 (R1), or anti-R2/R3). Bars show arithmetic means (±SD) for triplicate cultures. CTL activity is expressed as % lysis of EL4 tumor target cells (50:1 effector:target); cytokines are expressed as pg/ml in the culture supernatant at 40 hrs. Activity in control cultures (no C57BL/6 DC stimulator cells) was 1.0+0.6 (% lysis, CTL assay) and 40±15, 35±15 pg/ml (IFNγ and IL-10 respectively). *, p<0.05 compared with PBS control.
Figure 35:
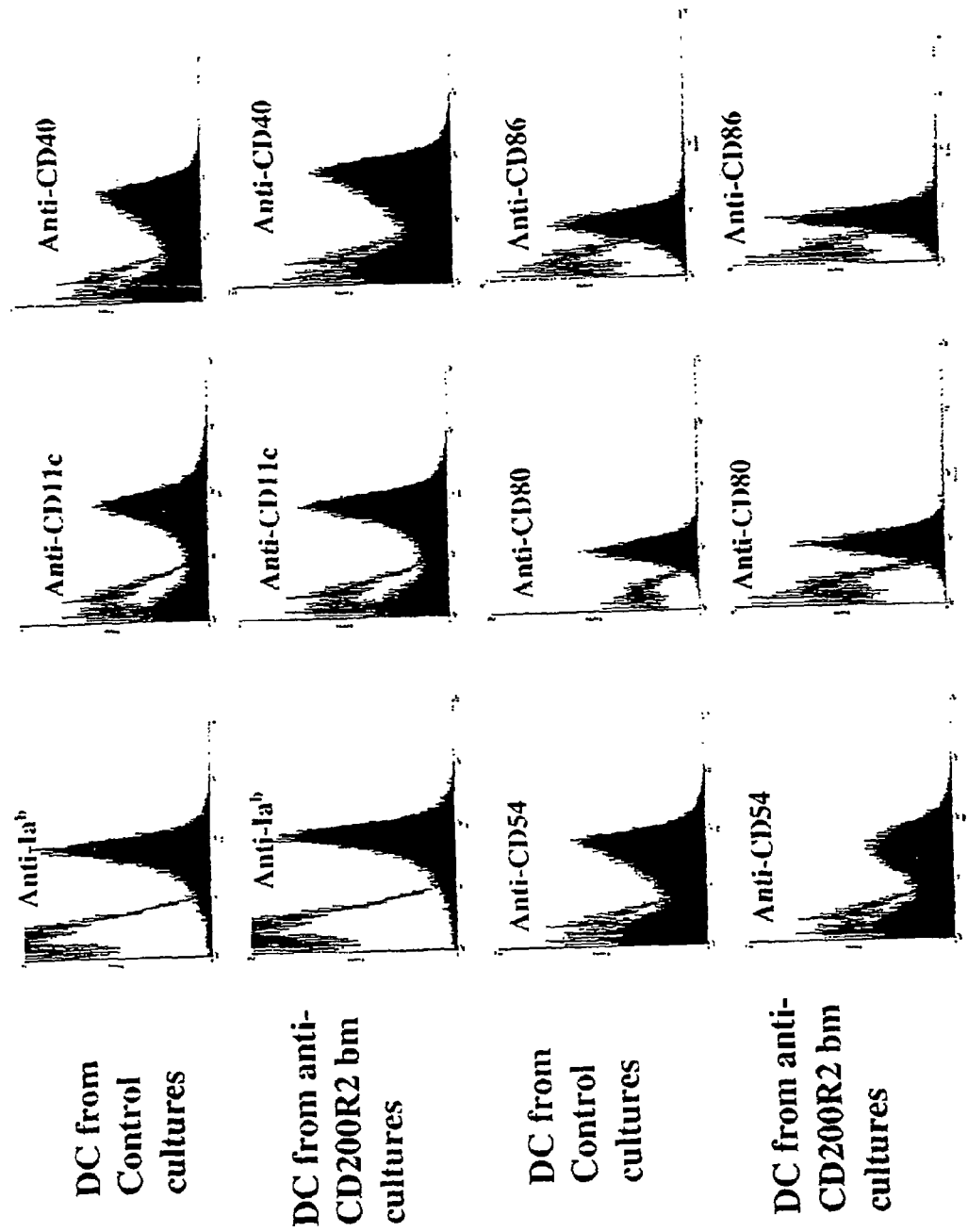
FIG. 35 is a comparison of FACS staining profile of bone-marrow derived DCs developing in the presence/absence of anti-CD200R2 mAbs.

Antigen-specific Suppression of Induction of CTLs in Fresh MLCs Using Cells Harvested from MLCs Using as Stimulator Cells DCs Derived from Bone Marrow Cells in the Presence/Absence of Anti-CD200R2:

Data in FIG. 34 show that DCs derived from marrow cells cultured in the presence of anti-CD200R fail to induce CTL or IFNγ in allogeneic spleen cells, yet, as judged by the data of FIG. 35, there are few dramatic changes in expression of classical costimulator molecules, including CD40, CD80, CD86 and class II MHC, following such treatment.

In order to assess whether the failure to induce CTL or type-1 cytokine production in vitro using DCs from bone marrow cells incubated with anti-CD200R2 mAb was associated with production of a specific "suppressor" pool, the inventors performed the following study. Cells were harvested from primary MLC cultures (set up as for FIG. 34), an aliquot assayed for CTL activity vs EIA targets, and varying numbers ($0.5 \times 10^5$ to $5.0 \times 10^5$) were then added in triplicate to fresh MLCs using C3H responder cells and spleen stimulator DCs of C57BL/6 or BALB/c origin. CTL specific for EL4 or P815 target cells were assayed at day 5 of these secondary cultures (see FIG. 36). In addition, IL-2, IL-4, IFNγ and IL-10 production in these secondary MLC cultures was assayed by ELISA, using supernatants harvested at 40 hrs. Data for IL-2 only are shown in FIG. 37.

The data in these latter two Figures (typical results of three independent studies) indicate that indeed, cells harvested from MLC cultures initiated with DCs derived from bone marrow cultures incubated in the presence of anti-CD200R2 mAb, contain antigen specific suppressor cells able to inhibit subsequent induction of CTL (FIG. 36) or type-1 cytokines (IL-2-FIG. 37) in a subsequent MLC. Equivalent data to FIG. 36 were seen assaying induction of IFNγ, while production of IL-10 and IL-4 was specifically increased by adding cells from the same primary MLCs (data not shown, but see FIG. 34). In additional studies (not shown) pre-adherence of cells from these primary (1°) MLCs using BM-derived DCs on anti-CD3 coated plates abolished their capacity to transfer suppression in 2° MLCs.

Figure 36:
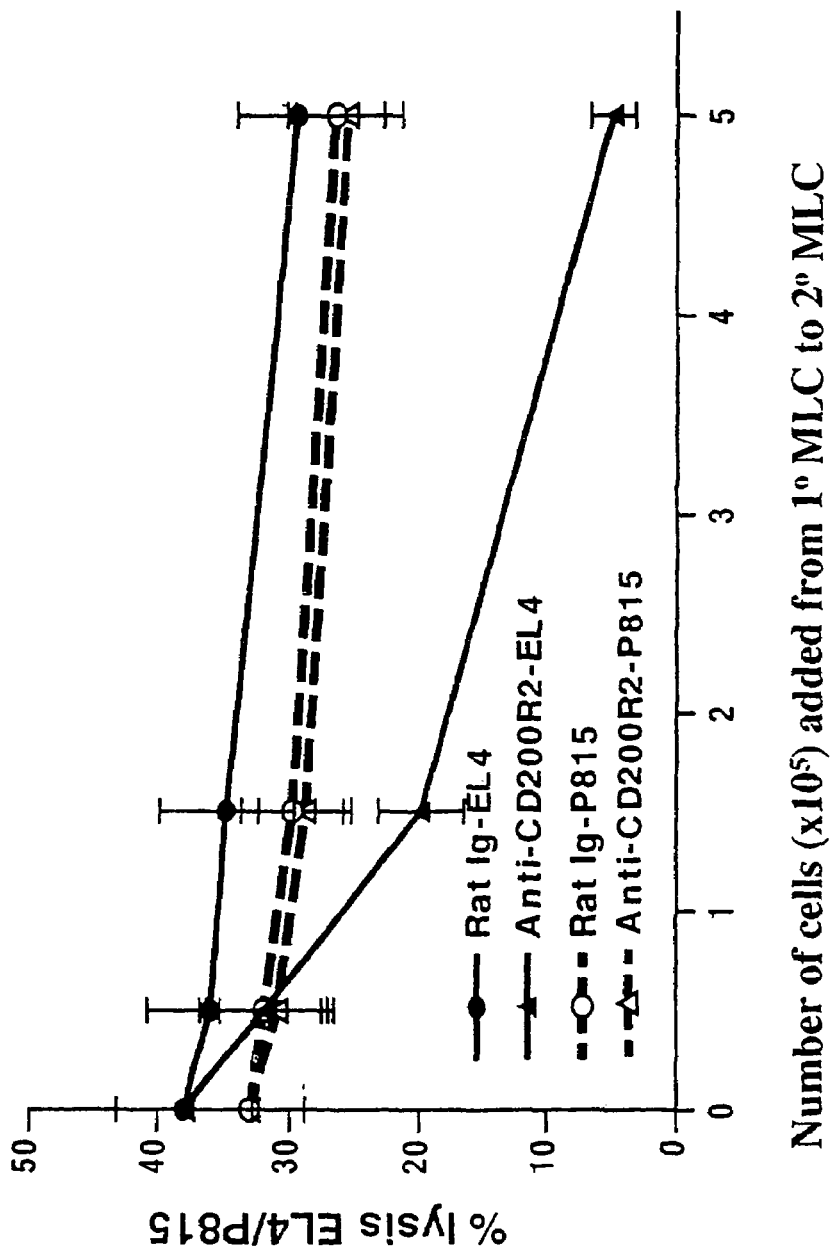
FIG. 36 is a graph showing generation of antigen-specific suppressor cells (active in 2° MLC cultures as defined by inhibition of CTL induction) in 1° MLC cultures using as DCs cells developing from bone marrow cells cultured in the presence of anti-CD200R2 mAb. All data represent means (±SD) of triplicate determinations, and show lysis of either EL4 or P815 tumor target cells, for 2° MLCs restimulated with C57BL/6 or BALB/c splenic DCs respectively. Varying numbers of cells from 1° MLCs were added (see abscissa) to cultures containing 1.0×10$^6$ C3H responder spleen cells and 3×10$^5$ C57BL/6 or BALB/c splenic DCs. C57BL/6 DCs for use in 1° MLCs were obtained following bone marrow culture in the presence of normal rat Ig or anti-CD200R2 (see FIG. 34). Testing of CTL activity (for EL4 targets) using cells harvested from these 1° MLCs (50:1, effector:target ratio) gave 33±4.1 or 4.2±1.8% lysis respectively.
Figure 37:
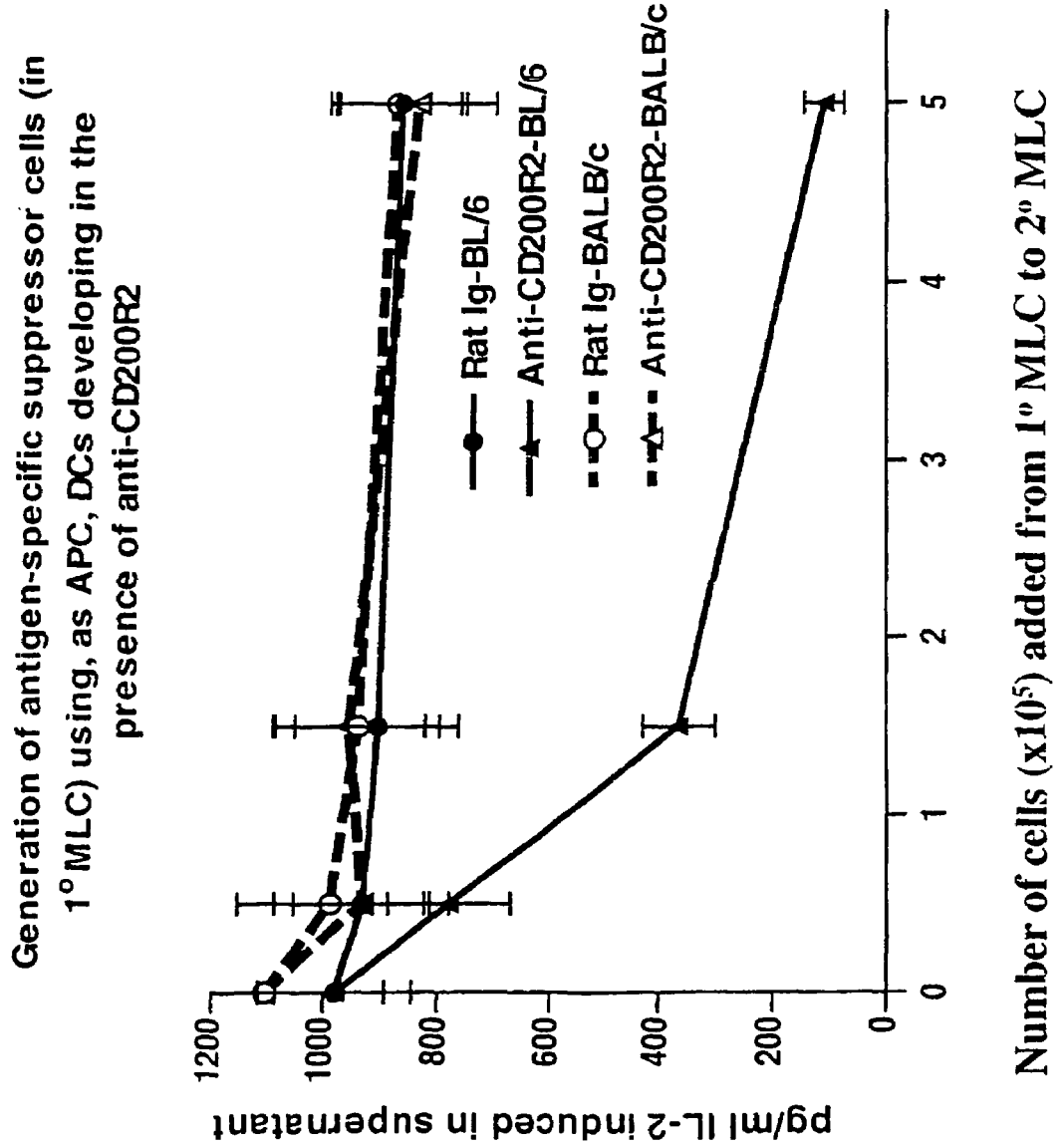
FIG. 37 is a graph showing as in FIG. 36, except that culture supernatants were harvested from secondary (2°) MLCs and tested for IL-2 activity at 40 hrs. Testing of IL-2 in supernatants harvested from the primary (1°) MLCs (using DCs derived from bone marrow incubated with/without anti-CD200R2) gave 115±40 or 920±155 pg/ml activity respectively.

Suppression in 2° MLCs is Over-ridden by Inclusion of an Excess of Stimulatory DCs The inventors interpreted that data of FIGS. 36 and 37 as implying that BM-derived DCs harvested from cultures initiated in the presence of anti-CD200R2 were preferentially "tolerance-inducing" DCs, even though their FACS profile showed no obvious difference from control DCs (produced in the absence of anti-CD200R2–see FIG. 35). The inventors postulated therefore, that suppression induced by these DCs would be a dose dependent function of the DCs added (rather than the suppressor cells added, as in FIGS. 36 and 37), and might even be over-ridden or masked in the presence of a large excess of allostimulatory DCs. In order to investigate these questions the inventors performed studies equivalent to those shown in FIGS. 34-37, using $1 \times 10^6$ responder C3H spleen cells, and in this case varying numbers of C57BL/6 DCs harvested from marrow cultures set up in the presence/absence of anti-CD200R2 (from 0 to $5 \times 10^5$), with fresh C57BL/6 spleen DCs added to a total DC number/culture of $5 \times 10^5$. At day 5 of culture (1o MLC) cells were assayed for lysis of EL4 target cells. In addition varying numbers of cells (0.5 to $3 \times 10^5$) were added as suppressor cells to 2° MLCs stimulated with C57BL/6 splenic DCs, and CTL assayed in these cultures 5 days later (FIG. 39).

Figure 38:
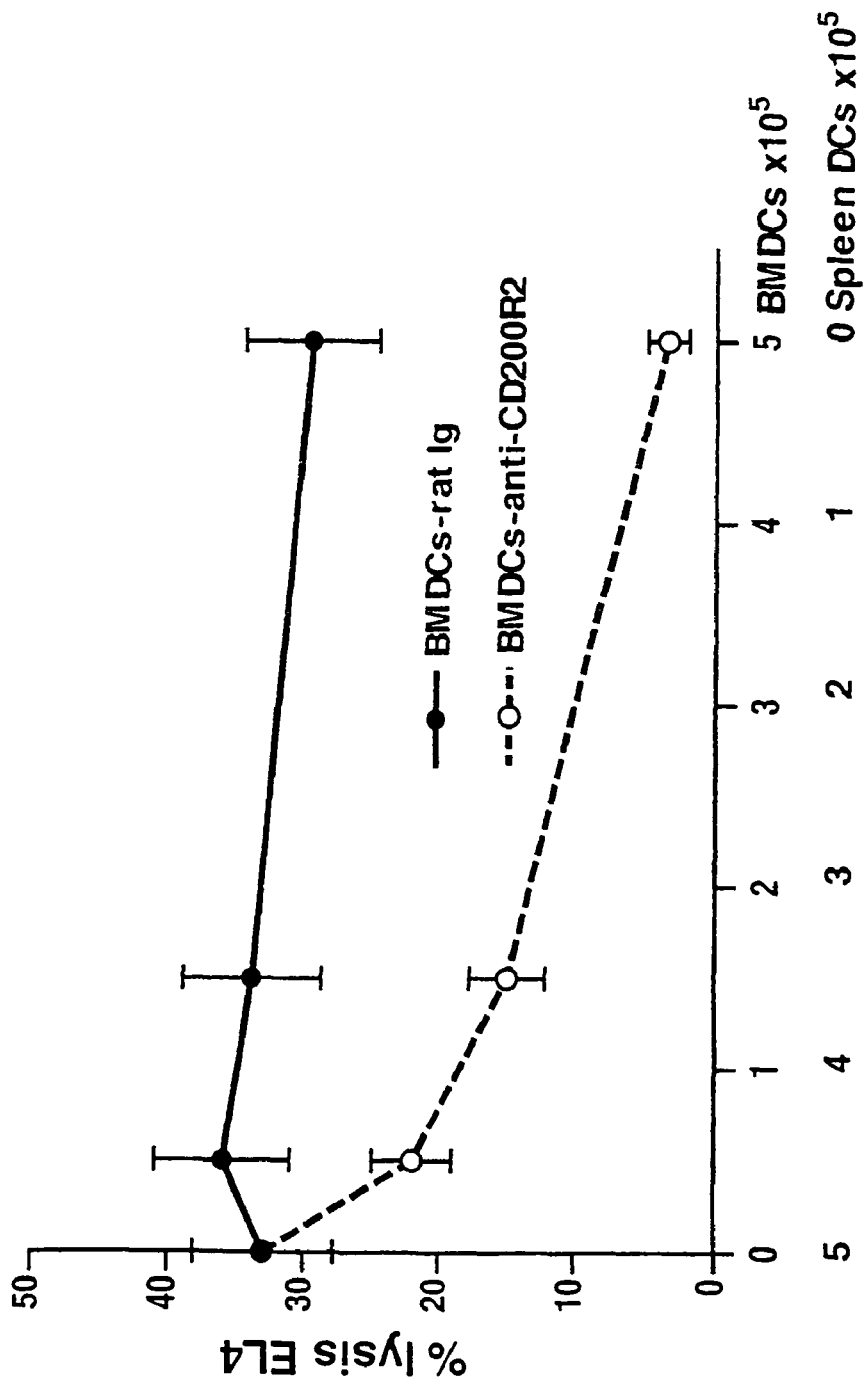
FIG. 38 is a graph showing excess allostimulatory DCs (from C57BL/6 spleen) can over-ride failure to stimulate CTL from C3H spleen cells in MLCs using bone-marrow derived DCs obtained from cells cultured in the presence of anti-CD200R2 mAb. Bars show arithmetic means (±SD) for triplicate cultures. CTL activity is expressed as % lysis of EL4 tumor target cells (50:1 effector:target). Data along the abscissa show the number/source of DCs added in the MLC (total in all cases 5×10$^5$). CTL activity in control cultures (no C57BL/6 DC stimulator cells) was 1.1±0.6%.
Figure 39:
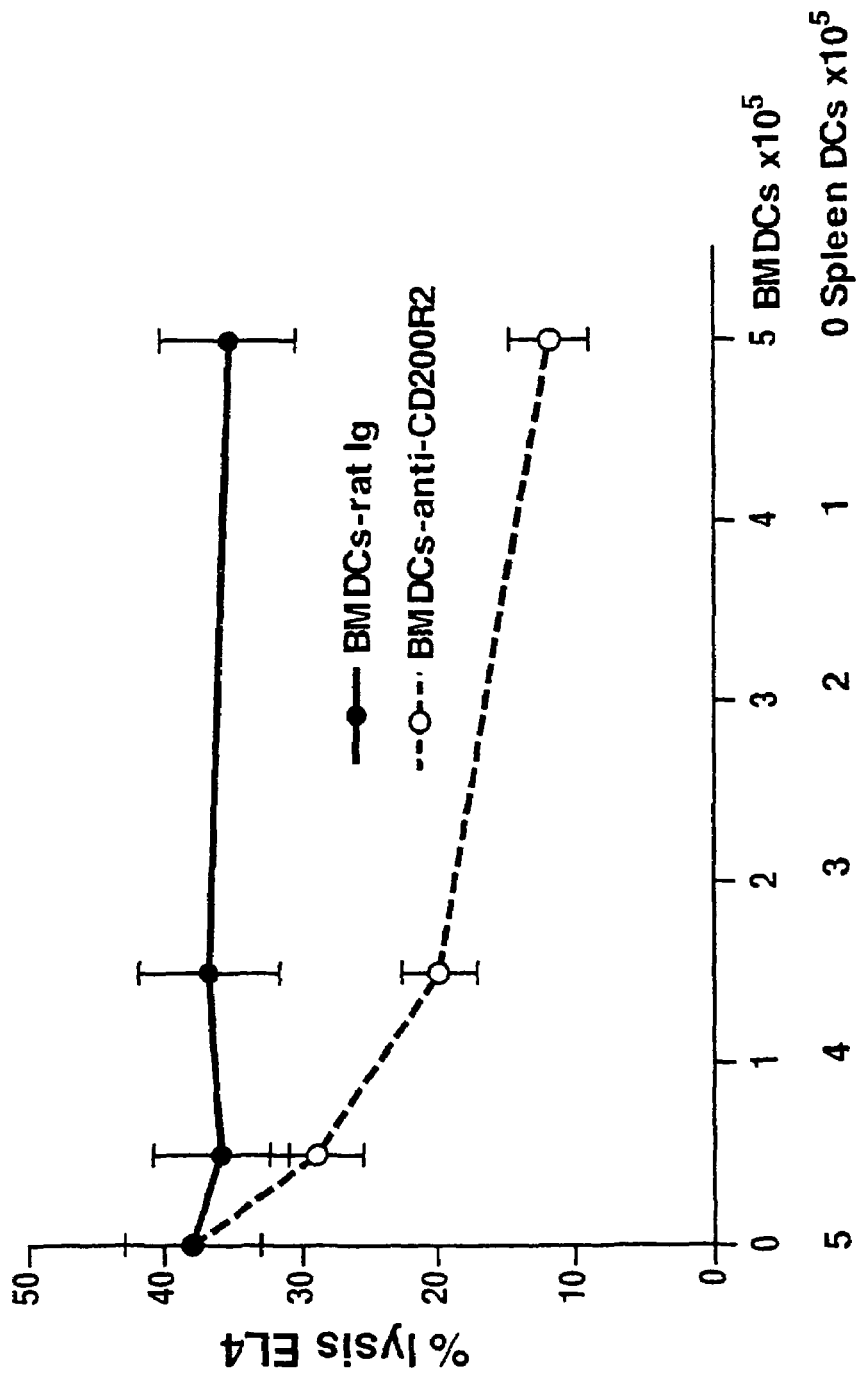
FIG. 39 is a graph showing excess allostimulatory DCs (from C57BL/6 spleen) can over-ride generation of suppressor cells (active in 2° MLC cultures as defined by inhibition of CTL induction) in 1° MLC cultures from FIG. 38, which used as DCs cells developing from bone marrow cells cultured in the presence of anti-CD200R2 mAb. All data represent means (±SD) of triplicate determinations, and show lysis of EL4 target cells for 2° MLCs restimulated with C57BL/6 splenic DCs. In all cases 2×10$^5$ suppressor cells from the 1° MLC (see FIGS. 36 and 38) were used in 2° MLC cultures containing 1.0×10$^6$ C3H responder spleen cells and 3×10⁵ C57BL/6 splenic DCs. In the 1° MLC, varying numbers of BMDCs were used in mixture with fresh C57BL/6 splenic DCs (see abscissa and FIG. 38—total DCs in culture 5×10⁵).

Data in FIGS. 38 and 39 show results from one of two studies of this type (the data in FIG. 39 are all from cultures using $2 \times 10^5$ suppressor cells harvested from 1° MLC with the different numbers of BMDCs shown). It is evident from these Figures that titration of excess stimulatory splenic DCs can over-ride both the failure to induce CTLs in 1° MLC, and the induction of suppressor cells (for 2√MLCs) in these 1° cultures, which is seen using as DCs cells derived from bone marrow cultures grown in the presence of anti-CD200R. These data imply a competition for T cell activation between APCs with allostimulatory capacity, and those with tolerance-inducing capacity, the latter being those DCs derived from anti-CD200R2 cultures.

Figure 40:
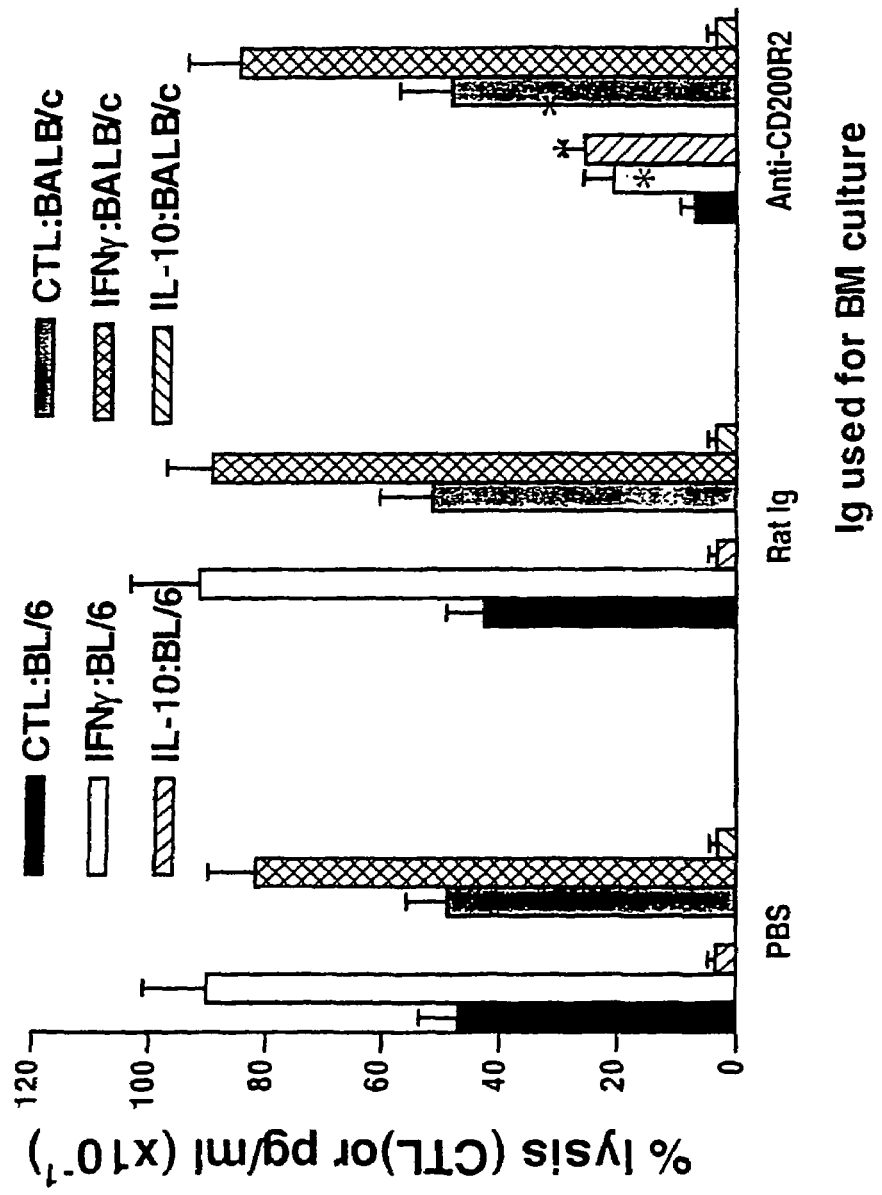
FIG. 40 is a bar graph showing induction of specific tolerance in vivo by BM-derived DCs (grown in the presence of anti-CD200R2), defined by failure to induce CTL or IFNγ from C3H spleen cells in MLCs using fresh splenic DCs (BL/6 or BALB/c) as in vitro stimulator. BM-derived DCs were from C57BL/6 cultures, and mice were challenged in vivo with BL/6 or BALB/c skin grafts for 14 days before sacrifice. Data show arithmetic mean (±SD) for triplicate cultures, each derived from measurements using 3 mice/group. *, $p<0.05$ compared with PBS control.

BM-derived DCs Cultured in the Presence of Anti-CD200R2 Induce Prolongation of Skin Graft Survival and Allo-tolerance Following Infusion in Vivo In order to examine the potential in vivo immunoregulatory role of BM-derived DCs cultured in the presence of anti-CD200R2, the inventors performed the following study. C57BL/6 bone marrow cells were cultured as described above (see FIG. 34) with (IL-4+GM-CSF), in the presence/absence of anti-CD200R2. At day 8 of culture cells were harvested, washed and $5 \times 10^6$ cells were infused intravenously into groups of 18 C3H mice. A control group received PBS only. Thereafter 9 mice/group received skin grafts of BALB/c or C57BL/6 origin. 3 mice/group were sacrificed at 14 days post transplantation, and spleen cells used in MLCs in vitro as responder cells, stimulated with C57BL/6 or BALB/c splenic DCs. CTL were assayed at day 5, and IFNγ and IL-10 assayed in culture supernatants measured by ELISA at 40 hrs (FIG. 40). Skin graft survival was followed daily for the remaining members of each group (see FIG. 41).

Figure 41:
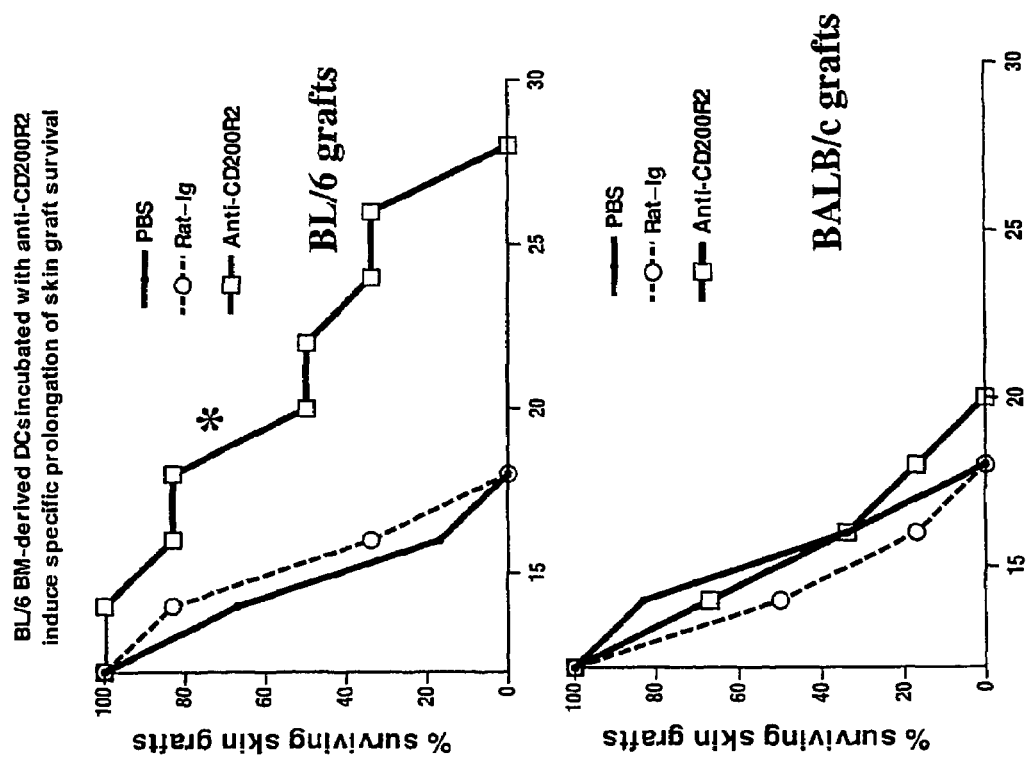
FIG. 41 is a graph showing skin graft survival (BL/6, upper panel; BALB/c, lower panel) in C3H mice receiving iv injections with BM-derived DCs grown in the presence/absence of anti-CD200R2. Data are for 6 mice/group. *, $p<0.05$ compared with PBS control, Mann-Whitney U-test.

The data shown in these Figures indicates that BM-derived DCs from anti-CD200R2 cultures induce allo-specific unresponsiveness in vivo, as defined both by failure to induce CTL or type-1 cytokines in vitro using spleen cells from recipient mice (FIG. 40), or by prolongation of skin graft survival (FIG. 41). Equivalent (reciprocal) data were obtained in repeat studies where BALB/c mice were used as BM-DC donors to provide a tolerizing cell population.

Discussion

In the studies reported in this example, the inventors have investigated whether one mechanism for a CD20R-induced immunoregulation involves an altered differentiation/development of DCs themselves, such that the population of cells delivering APC signals to T cells is intrinsically altered, with resultant development of Tr subsets. Data in FIGS. 34 and 41 indicate that indeed BM-derived DCs from cultures differentiating in the presence of anti-CD200R mAbs are unable to stimulate CTL or the type-1 cytokine IFNγ in vitro, and can suppress graft rejection in vivo on adoptive transfer intravenously in mice. While the data shown are, in general, from experiments using anti-CD200R2 only, the inventors have obtained equivalent results using anti-CD200R1 and R2 antibodies (see, for instance, FIG. 34).

MLC cultures activated in the presence of DCs grown in the presence of anti-CD200R develop an antigen-specific suppressor cell population capable of inhibiting development of CTL and type-1 (but not type-2) cytokine producing cells on adoptive transfer (FIGS. 36 and 37). FACS profiles of the DCs grown in the presence/absence of anti-CD200R did not indicate any clear phenotypic difference between the DC subsets, a phenomenon reported elsewhere also for $CD8\alpha^+/CD8\alpha^-$ subsets with/without exposure to maturation stimuli (123, 135), suggesting that the functional differences are not easily interpreted in terms of subtle differences in maturation states of the DCs derived under these conditions. Interestingly, and as seen by O'Connell using splenic DC subpopulations, the "tolerogenic" effect of DCs isolated from anti-CD200R cultures was overcome by inclusion of stimulatory DCs (see FIGS. 38 and 39).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

A slow-sedimenting (3-4.5 mm/hour) LPS stimulated spleen cell population is stimulated in the presence of CD200:Fc to inhibit CTL and type-1 cytokine production in vitro

| LPS-stimulated[a] cells added | CD200:Fc added | Percent lysis $^{51}$Cr targets[b] and LU20 (% inhibition) | | Cytokines in culture (% inhibition)c | |
|---|---|---|---|---|---|
| | | | | IL-2 | IFNγ |
| NONE | − | 44 ± 6.7 | 821 | 1180 ± 210 | 940 ± 100 |
| NONE | + | 13 ± 3.6* | 139 | 360 ± 75* | 45 ± 40* |
| | | (83) | | (69) | (74) |
| (3-4.5 mm/hr) | − | 36 ± 6.1 | 446 | 1135 ± 190 | 870 ± 120 |
| (3-4.5 mm/hr) | + | 3.2 ± 2.0** | 33 | 140 ± 50** | 100 ± 40** |
| | | (96) | | (88) | (89) |
| (4.5-6 mm/hr) | − | 42 ± 5.6 | 545 | 1215 ± 220 | 940 ± 110 |
| (4.5-6 mm/hr) | + | 16 ± 3.9* | 174 | 335 ± 110* | 270 ± 60* |
| | | (68) | | (72) | (71) |
| (>6 mm/hr) | − | 19 ± 4.2* | 211 | 505 ± 130* | 400 ± 90* |
| (>6 mm/hr) | + | 8.4 ± 2.9* | 82 | 275 ± 70* | 210 ± 60* |
| | | (90) | | (46) | (47) |

Footnotes:

[a]$5 \times 10^6$ responder C3H spleen cells, pooled from 38-week donors, were cultured in triplicate with $2.5 \times 10^6$ mitomycin-c treated C57BL/6 DC, in the presence/absence of $1 \times 10^6$ cells from one of 3 pools of velocity-sedimented, LPS stimulated, T-depleted, spleen cells (see text and legend to FIG. 3 for more details). Cultures received additional CD200:Fc protein as shown.

[b]Percent lysis (50:1, effector:target) at 5 days using $1 \times 10^4$ $^{51}$Cr C57BL/6 spleen ConA targets. LU20 are defined as the LU/$10^6$ cells, where 1 LU lyses 20% of targets in 4 hrs. Data in parentheses represents % inhibition of control response (no added cells, no CD200:FC-see first row).

cCytokines in pg/ml in culture supernatants harvested at 40 hrs. Data in parentheses represents % inhibition of response in control cultures (first row).

*$p < 0.05$ compared with control cultures in first row (ANOVA followed by pair wise t-test);

**$p < 0.05$ compared with all other groups (pair wise t-test).

TABLE 2

F4/80$_+$, slow-sedimenting (3-4.5 mm/hr) LPS stimulated spleen cells stimulated in the presence of CD200:Fc provide optimal inhibition of CTL and type-1 cytokine production in vitro

| LPS-stimulated cells added | CD200:Fc added | 51Cr targetsb (50:1, effector:target) Percent lysis | Cytokines in culture (pg/ml)c | |
|---|---|---|---|---|
| | | | IL-2 | IFNγ |
| NONE | − | 31 ± 4. | 910 ± 160 | 1060 ± 150 |
| NONE | + | 17 ± 3.2* | 460 ± 70* | 510 ± 90 |
| (3-4.5 mm/hr): Unfx | − | 30 ± 4.1 | 915 ± 150 | 1040 ± 140 |
| (3-4.5 mm/hr): Unfx | + | 6.9 ± 2.3** | 240 ± 55** | 230 ± 45** |
| (3-4.5 mm/hr): F4/80+ | − | 28 ± 5.3 | 935 ± 160 | 1050 ± 160 |
| (3-4.5 mm/hr): F4/80+ | + | 3.0 ± 1.7** | 90 ± 30** | 105 ± 35** |
| (3-4.5 mm/hr): F4/80− | − | 27 ± 4.8 | 915 ± 150 | 990 ± 145 |
| (3-4.5 mm/hr): F4/80− | + | 16 ± 3.2* | 380 ± 50* | 390 ± 40* |

TABLE 2-continued

F4/80+, slow-sedimenting (3-4.5 mm/hr) LPS stimulated spleen cells stimulated in the presence of CD200:Fc provide optimal inhibition of CTL and type-1 cytokine production in vitro

| LPS-stimulated cells added | CD200:Fc added 51Cr targetsb (50:1, effector:target) | Percent lysis | Cytokines in culture (pg/ml)c IL-2 | IFNγ |
|---|---|---|---|---|
| (>6 mm/hr) | − | 14 ± 3.7* | 310 ± 80* | 390 ± 85* |
| (>6 mm/hr) | + | 8.6 ± 2.9* | 270 ± 75* | 230 ± 55* |

Footnotes:
a-c as for Table 1. $5 \times 10^6$ responder C3H spleen cells, pooled from 38-week donors, were cultured in triplicate with $2.5 \times 10^6$ mitomycin-c treated C57BL/6 DC, in the presence/absence of $1.5 \times 10^6$ (or $3 \times 10^5$ for the F4/80+ pool) cells from velocity-sedimented, LPS stimulated, T-depleted, spleen cells. Cultures received additional CD200:Fc protein as shown. Further separation of small cells into F4/80+ and F4/80− populations used an anti-PE column and PE-anti-F4/80 (see Materials and Methods). Total recovery was 80%, and recovery of the F4/80+ population (10% of the 3-4.5 mm/hr pool) was 70%.
*$p < 0.05$ compared with control cultures in first row (ANOVA followed by pair wise t-test);
**,$p < 0.05$ compared with all other * groups (pair wise t-test).

TABLE 3

Inhibition of CTL induction by slow-sedimenting (3-4.5 mm/hr) LPS stimulated spleen cells in the presence of CD200:Fc depends upon their being MHC-matched with allo-stimulatory DC.

| | | Percent lysis 51Cr targets (50:1 E:T ratio)b | | |
|---|---|---|---|---|
| LPS-stimulated cells added | CD200:Fc added | B10.BR anti-B10.Sgn | B10.Sgn anti-B10.BR | B10.BR anti-B10.D2 |
| NONE | − | 40 ± 5.3 | 43 ± 5.5 | 52 ± 6.3 |
| NONE | + | 12 ± 3.2* | 13 ± 3.3 | 17 ± 4.4* |
| (3-4.5 mm/hr) | − | 37 ± 6.4 | 42 ± 6.0 | 49 ± 5.9 |
| (3-4.5 mm/hr) | + | 4.6 ± 2.2** | 12 ± 3.4* | 16 ± 4.2* |
| (4.5-6 mm/hr) | − | 39 ± 6.3 | 40 ± 4.9 | 44 ± 5.6 |
| (4.5-6 mm/hr) | + | 13 ± 3.4* | 13 ± 2.9* | 15 ± 4.0* |
| (>6 mm/hr) | − | 17 ± 4.3* | 32 ± 4.4* | 28 ± 4.9* |
| (>6 mm/hr) | + | 7.2 ± 2.4* | 10 ± 2.3* | 13 ± 3.8* |

Footnotes:
a. $5 \times 10^6$ responder spleen cells were pooled from 3, 8-week B10.BR (anti-B10, anti-B10.D2 response) or B10.Sgn (anti-B10.BR response) donors. Cells were cultured in triplicate with $2.5 \times 10^6$ mitomycin-C treated allogeneic DC, in the presence/absence of $1 \times 10^6$ cells from one of 3 pools of velocity-sedimented, LPS stimulated, T-depleted, B10.Sgn spleen cells (see text and footnotes to Table 1). Some cultures received additional CD200:Fc protein as described in Materials and Methods.
bPercent lysis (50:1, effector:target) at 5 days using $1 \times 10^4$ 51Cr spleen ConA targets.
*$p < 0.05$ compared with control cultures in first row (ANOVA followed by pair wise t-test);
**, $p < 0.05$ compared with all other groups (pair wise t-test).

TABLE 4

CD200R+ T cells, preferably γδ-TCR+ cells, are stimulated in the presence of CD200:Fc to inhibit Cytotoxic T Lymphocytes (CTL) and type-1 cytokine production in vitro. CTL activity is expressed as a % specific lysis (of target cells). Cytokine levels were measured 48 hours after incubation.

| Cells added for inhibition | CD200:Fc added | % lysis | Cytokines in Supernatent (pg/ml) IL-2 | IL-10 |
|---|---|---|---|---|
| NONE | − | 31 | 1120 | 145 |
| NONE | + | 19 | 475 | 190 |
| Thymic Con A blasts | − | 20 | 825 | 150 |
| Thymic ConA blasts | + | 12.5 | 315 | 255 |
| Peyers Patch (gamma/delta) | − | 33 | 1050 | 135 |
| Peyers Patch (gamma/delta) | + | 5.1 | 130 | 490 |

TABLE 5

LPS stimulated CD200R+ cells augment inhibition of type-1 cytokine production by CD200

| CD200R+ cellsa | CD200Fcb | CD200+ DCc | Cytokines in culture (pg/ml)d IL-2 | IL-4 | IFNγ | IL-10 |
|---|---|---|---|---|---|---|
| NONE | NONE | − | 1150 ± 190 | 55 ± 15 | 910 ± 180 | 45 ± 10 |

TABLE 5-continued

LPS stimulated CD200R+ cells augment inhibition of type-1 cytokine production by CD200

| CD200R+ cells[a] | CD200Fc[b] | CD200+ DC[c] | Cytokines in culture (pg/ml)[d] | | | |
|---|---|---|---|---|---|---|
| | | | IL-2 | IL-4 | IFNγ | IL-10 |
| NONE | + | − | 460 ± 105* | 155 ± 30* | 395 ± 90* | 100 ± 20* |
| + | NONE | − | 1135 ± 195 | 60 ± 20 | 870 ± 160 | 55 ± 15* |
| + | + | − | 190 ± 60** | 270 ± 55** | 185 ± 45** | 195 ± 30** |
| NONE | NONE | + | 405 ± 95* | 160 ± 30* | 370 ± 85* | 95 ± 25* |
| + | NONE | + | 160 ± 50** | 255 ± 60** | 145 ± 50** | 225 ± 40** |

Footnotes:
[a] $5 \times 10^5$ C3H splenocytes were stimulated with $2 \times 10^5$ unfractionated, LPS treated, C57BL/6 DC (<10% CD200+-see FIG. 1). $1 \times 10^5$ CD200R+ cells were derived from velocity sedimentation of 48 hr LPS-stimulated C57BL/6 splenic cells (>30% positive with anti-CD200R mAb)[21].
[b] Exogenous CD200Fc was added at a concentration of 100 ng/ml; control IgG2a (at >1 μg/ml) produced no effect alone, or with CD200R+ cells (see [8]).
[c] Additional CD200+ C57BL/6 DC ($1 \times 10^5$/culture) were obtained as the slow sedimenting pool of LPS stimulated cells (see FIG. 1—Fx 1; ~30% CD200+).
[d] Cytokines in culture supernatant at 40 hrs.
*$p < 0.05$ compared with first row;
**$p < 0.05$ compared with all other groups.

TABLE 6

F(ab')₂ anti-CD200 or anti-CD200R block inhibition of type-1 cytokine production by CD200:CD200R interaction

| CD200R+ cells[a] | CD200+ DC[b] | F(ab')₂ mAb[c] | Whole Ig mAb[d] | Cytokines in culture (pg/ml)[e] | |
|---|---|---|---|---|---|
| | | | | IL-2 | IFNγ |
| NONE | NONE | − | − | 1210 ± 210 | 1010 ± 190 |
| NONE | + | − | − | 410 ± 115* | 380 ± 95* |
| NONE | + | Anti-CD200 | − | 1165 ± 190 | 1070 ± 180 |
| NONE | + | Anti-CD200R | − | 985 ± 195 | 970 ± 190 |
| NONE | + | − | Anti-CD200 | 1080 ± 170 | 1010 ± 160 |
| NONE | + | − | Anti-CD200R | 385 ± 105* | 320 ± 90* |
| + | NONE | − | − | 1190 ± 160 | 1085 ± 195 |
| + | + | − | − | 165 ± 55** | 170 ± 40** |
| + | + | Anti-CD200 | − | 860 ± 170 | 945 ± 150 |
| + | + | Anti-CD200R | − | 910 ± 150 | 895 ± 175 |
| + | + | − | Anti-CD200 | 980 ± 150 | 910 ± 130 |
| + | + | − | Anti-CD200R | 125 ± 45* | 155 ± 50* |

Footnotes:
[a],[b] and [e] as for Table 1(a, b and d).
[c] and [d] Undigested or F(ab')₂ mAbs (column c) were added at a final concentration of 5 μg/ml.

TABLE 7

Anti-CD200R, but not anti-CD200 or F(ab')₂ fragments of anti-CD200R, induces inhibition of cytokine production in an IL-6 inhibitable fashion

| CD200R+ cells[a] | mAb[b] | Anti-IL-6 mAb[c] | Cytokines in culture (pg/ml)[d] | |
|---|---|---|---|---|
| | | | IL-2 | IFNγ |
| NONE | − | − | 1075 ± 170 | 1065 ± 170 |
| NONE | Anti-CD200 | − | 1115 ± 190 | 1120 ± 180 |
| NONE | Anti-CD200R | − | 585 ± 145* | 520 ± 140* |
| NONE | F(ab')₂anti-CD200R | − | 990 ± 165 | 990 ± 160 |
| NONE | Anti-CD200 | + | 1090 ± 165 | 1040 ± 160 |
| NONE | Anti-CD200R | + | 955 ± 145 | 920 ± 140 |
| NONE | F(ab')₂anti-CD200R | + | 825 ± 165 | 820 ± 140 |
| + | − | − | 1015 ± 150 | 1005 ± 190 |
| + | Anti-CD200 | − | 935 ± 150 | 970 ± 150 |
| + | Anti-CD200R | − | 225 ± 55* | 190 ± 60* |
| + | F(ab')₂anti-CD200R | − | 965 ± 155 | 955 ± 150 |
| + | Anti-CD200 | + | 1000 ± 150 | 930 ± 145 |
| + | Anti-CD200R | + | 585 ± 65** | 555 ± 60** |
| + | F(ab')₂anti-CD200R | + | 955 ± 155 | 950 ± 150 |

Footnotes:
[a] and [d] As for Table 1
[b] and [c] mAbs were used at a 5 μg/ml final concentration in the culture medium; where shown, a F(ab')₂ digest of anti-CD200R was also used (see Table 2 and FIG. 2).
*$p < 0.05$ compared with control (first row);
**$p < 0.05$ compared with equivalent group lacking IL-6.

TABLE 8

Composite of FACS staining profile for cells in different tissues

| Anti-CD200R | % positive stained cells in | | | |
|---|---|---|---|---|
| | Spleen | Bone marrow | PBL | Thymus |
| Rabbit/rat heteroantibodies (4/group) | | | | |
| FITC-control | 1.8 ± 0.8 | 1.4 ± 0.5 | 1.4 ± 0.7 | 3.1 ± 0.9 |
| Anti-CD200R1 | 6.5 ± 1.3 | 6.5 ± 1.8 | 13 ± 2.2 | 27 ± 5.5 |
| Anti-CD200R2a | 2.8 ± 1.1 | 25 ± 4.3 | 3.4 ± 1.3 | 3.0 ± 0.6 |
| Anti-CD200R2b | 3.9 ± 1.0 | 31 ± 4.8 | 5.3 ± 1.9 | 2.9 ± 0.5 |
| Anti-CD200R3a | 3.0 ± 1.0 | 22 ± 3.9 | 3.5 ± 1.2 | 3.1 ± 0.8 |
| Anti-CD200R3b | 4.2 ± 0.9 | 35 ± 4.8 | 6.0 ± 1.5 | 3.3 ± 0.5 |
| Rat monoclonal antibodies (>5/group) | | | | |
| YB2/0-control | 1.0 ± 0.2 | 1.0 ± 0.3 | 1.2 ± 0.3 | 1.4 ± 0.2 |
| Anti-CD200R1 | 5.2 ± 1.5 | 8.3 ± 1.5 | 11 ± 3.3 | 20 ± 4.9 |
| Anti-CD200R2a | 2.2 ± 1.3 | 22 ± 5.9 | 3.2 ± 1.2 | 1.3 ± 0.3 |
| Anti-CD200R2b | 4.4 ± 1.5 | 35 ± 7.2 | 4.7 ± 1.5 | 2.0 ± 0.4 |
| Anti-CD200R3a | 2.8 ± 1.4 | 20 ± 5.9 | 2.7 ± 1.4 | 1.8 ± 0.4 |
| Anti-CD200R3b | 4.8 ± 0.7 | 37 ± 6.9 | 6.5 ± 2.3 | 2.0 ± 0.3 |

Footnotes:
aRabbit or rat heteroantisera (top 5 rows) or rat mAbs to different CD200R isoforms (last 5 rows) were used in FACS analysis with cells from the tissues shown. LPS spleen (or ConA thymus) cells were obtained following overnight culture of cells at 1 × 10$^6$/ml with mitogen at 5 mg/ml.
b% positive cells (arithmetic mean ± SD) of 3 determinations; in the case of the mAbs, data are pooled from triplicate assays of at least 5 independent mAbs/group.

TABLE 9

Induction of TNFα and/or IL-6 in spleen cells using antibodies to CD200R isoforms

| Anti-CD200R | Cytokine concentration assayed in culture supernatant (pg/ml) | |
|---|---|---|
| serum tested | TNFα | IL-6 |
| NONE | 60 ± 15 | 55 ± 10 |
| Rabbit anti-R1 | 350 ± 75 | 550 ± 170 |
| Rabbit anti-R2a | 110 ± 25 | 100 ± 15 |
| Rabbit anti-R2b | 190 ± 40 | 220 ± 65 |
| Rabbit anti-R3a | 95 ± 20 | 110 ± 20 |
| Rabbit anti-R3b | 240 ± 55 | 255 ± 75 |
| mAbs R1 | 440 ± 105 | 655 ± 135 |
| mAbs R2a | 140 ± 35 | 155 ± 25 |
| mAbs R2b | 270 ± 55 | 315 ± 45 |
| mAbs R3a | 120 ± 25 | 185 ± 45 |
| mAbs R3b | 290 ± 55 | 355 ± 65 |

Footnotes:
aRabbit heteroantisera or rat mAbs to different CD200R isoforms were used to stimulate spleen cells for 24 hrs in culture. Thereafter supernatants were tested in ELISA for production of TNFα/IL-6. Control groups contained no antibody, or antibody pre-screened and not showing FACS staining using CHO cells transduced with CD200Rs.
b% positive cells (arithmetic mean ± SD) in triplicate assays each with 2 independent rabbit sera; in the case of the mAbs, data are pooled from triplicate assays of a minimum of 5 independent mAbs/group.

FULL CITATIONS FOR REFERENCES REFERRED TO IN THE SPECIFICATION

1. Gorczynski, R. M., M. S. Cattral, Z. G. Chen, J. A. Hu, J. Lei, W. P. Min, G. Yu, and J. Ni. 1999. An immunoadhesin incorporating the molecule CD200 is a potent immunosuppressant that prolongs allo- and xenograft survival. *J Immunol* 163:1654.

2. Gorczynski, R. M., and W. Holmes. 1991. Specific manipulation of immunity to skin grafts bearing multiple minor histocompatibility differences. *Immunology Letters* 27:163.

3. Gorczynski, R. M., Z. Chen, S. Chung, Z. Cohen, G. Levy, B. Sullivan, and X.-M. Fu. 1994. Prolongation of rat small bowel or renal allograft survival by pretransplant transfusion and/or by varying the route of allograft venous drainage. *Transplantation* 58:816.

4. Gorczynski, R. M., Z. Chen, X. M. Fu, and H. Zeng. 1998. Increased expression of the novel molecule CD200 is involved in prolongation of murine renal allograft survival. *Transplantation* 65:1106.

5. Barclay, A. N. 1981. Different reticular elements in rat lymphoid tissue identified by localization of Ia, Thy-1 and MRC CD200 antigens. *Immunology* 44:727.

6. Gorczynski, R. M., Z. Cohen, X. M. Fu, and J. Lei. 1999. Anti-rat CD200 blocks increased small intestinal transplant survival after portal vein immunization. *Transpl. Proc.* 31:577.

7. Gorczynski, L., Z. Chen, J. Hu, G. Kai, V. Ramakrishna, and R. M. Gorczynski. 1999. Evidence that an CD200 positive cell can inhibit the stimulation of type-1 cytokine production by bone-marrow-derived B7-1 (and B7-2) positive dendritic cells. *J. Immunol.* 162:774.

8. Forster, E., W. Krenger, J. Joergensen, R. Hof, R. S. Geha, and G. A. Hollander. 1999. Contribution of CD40-CD154-mediated costimulation to an alloresponse in vivo. *Transplantation* 67:1284.

9. Lespagnard, L., P. Mettens, T. DeSmedt, H. Bazin, J. Urbain, O. Leo, and M. Moser. 1998. The immune response induced in vivo by dendritic cells is dependent on B7-1 or B7-2, but the inhibition of both signals does not lead to tolerance. *Int Immunol* 10:295.

10. Walunas, T. L., and J. A. Bluestone. 1998. CTLA-4 regulates tolerance induction and T cell differentiation in vivo. *J Immunol* 160:3855.

11. Walunas, T. L., A. I. Sperling, R. Khattri, C. B. Thompson, and J. A. Bluestone. 1996. CD28 expression is not essential for positive and negative selection of thymocytes or peripheral T cell tolerance. *Journal of Immunology* 156:1006.

12. Hancock, W. W., M. H. Sayegh, X. G. Zheng, R. Peach, P. S. Linsley, and L. A. Turka. 1996. Costimulatory function and expression of CD40 ligand, CD80, and CD86 in vascularized murine cardiac allograft rejection. *Proc Natl Acad Sci USA* 93:13967.

13. Freeman, G. J., V. A. Boussiotis, A. Anumanthan, G. M. Bernstein, X. Y. Ke, P. D. Rennert, G. S. Gray, J. G. Gribben, and L. M. Nadler. 1995. B7-1 and B7-2 do not deliver identical costimulatory signals, since B7-2 but not B7-1 preferentially costimulates the initial production of IL-4. *Immunity* 2:523.

14. Kuchroo, V. K., M. P. Das, J. A. Brown, A. M. Ranger, S. S. Zamvil, A. Sobel, H. L. Weiner, N. Nabavi, and L. H. Glimcher. 1995. B7-1 and B7-2 costimulatory molecules activate differentially the Th1/Th2 developmental pathways: application to autoimmune disease therapy. *Cell* 80:707.

15. Emtage, P. C. R., Y. H. Wan, J. L. Bramson, F. L. Graham, and J. Gauldie. 1998. A double recombinant adenovirus expressing the costimulatory molecule B7-1 (murine) and human IL-2 induces complete tumor regression in a murine breast adenocarcinoma model. *J Immunol* 160:2531.

16. Imro, M. A., P. Dellabona, S. Manici, S. Heltai, G. Consogno, M. Bellone, C. Rugarli, and M. P. Protti. 1998.

Human melanoma cells transfected with the B7-2 costimulatory molecule induce tumor-specific CD8(+) cytotoxic T lymphocytes in vitro. *Hum Gene Ther* 9:1335.
17. Osman, G. E., S. Cheunsuk, S. E. Allen, E. M. Chi, H. D. Liggitt, L. E. Hood, and W. C. Ladiges. 1998. Expression of a type II collagen-specific TCR transgene accelerates the onset of arthritis in mice. *Int Immunol* 10:1613.
18. Preston, S., G. J. Wright, K. Starr, A. N. Barclay, and M. H. Brown. 1997. The leukocyte/neuron cell surface antigen CD200 binds to a ligand on macrophages. *Eur j Immunol* 27:1911.
19. Ragheb, R., Abrahams, S., Beecroft, R., Hu, J., Ni, J., Ramakrishna, V., Yu, G. and Gorczynski, R. M. 1999. Preparation and functional properties of monoclonal antibodies to human, mouse and rat CD200. *Immunology Letters* 68:311.
20. Gorczynski, R. M. 1994. Adoptive transfer of unresponsiveness to allogeneic skin grafts with hepatic γδ+ T cells. *Immunology* 81:27.
21. McLaren, A. J., S. E. Marshall, N. A. Haldar, C. G. Mullighan, S. V. Fuggle, P. J. Morris, and K. I. Welsh. 1999. Adhesion molecule polymorphisms in chronic renal allograft failure. *Kidney Int* 55:1977.
22. Fabrega, E., J. Crespo, F. Casafont, J. Delapena, G. Delasheras, J. A. Amado, and F. Ponsromero. 1995. Endothelin-1 and vascular complications in liver transplantation. *Transplantation* 59:1748.
23. Gorczynski, R. M. 1992. Immunosuppression induced by hepatic portal venous immunization spares reactivity in IL-4 producing T lymphocytes. *Immunology Letters* 33:67.
24. Miller, R. G., and R. A. Phillips. 1969. The separation of cells by velocity sedimentation. *Journal of cellular and comparative physiology* 73:191.
25. Chen, Z., H. Zeng, and R. M. Gorczynski. 1997. Cloning and characterization of the murine homologue of the rat/human MRC CD200 gene. *Bba Mol Basis Dis* 1362:6.
26. Streilein, J. W., M. Takeuchi, and A. W. Taylor. 1997. Immune privilege, T-cell tolerance, and tissue-restricted autoimmunity. *Hum Immunol* 52:138.
27. Gorczynski, R. M., N. Hozumi, S. W. Wolfe, and Z. Chen. 1995. Interleukin-12, in combination with anti-interleukin-10, reverses graft prolongation after portal venous immunization. *Transplantation* 60:1337-1341.
28. Schwartz, R. H. 1996. Models of T cell anergy: Is there a common molecular mechanism? *J Exp Med* 184:1.
29. Borriello, F., J. Lederer, S. Scott, and A. H. Sharpe. 1997. MRC CD200 defines a novel T cell costimulatory pathway. *J. Immunol.* 158:4549.
30. Salomon, B., J. L. Cohen, C. Masurier, and D. Klatzmann. 1998. Three populations of mouse lymph node dendritic cells with different origins and dynamics. *Journal of Immunology* 160:708.
31. Leenen, P. J. M., K. Radosevic, J. S. A. Voerman, B. Salomon, N. vanRooijen, D. Klatzmann, and W. vanEwijk. 1998. Heterogeneity of mouse spleen dendritic cells: In vivo phagocytic activity, expression of macrophage markers, and subpopulation turnover. *J Immunol* 160:2166.
32. Larsen, C. P., S. C. Ritchie, R. Hendrix, P. S. Linsley, K. S. Hathcock, R. J. Hodes, R. P. Lowry, and T. C. Pearson. 1994. Regulation of immunostimulatory function and costimulatory molecule (B7-1 and B7-2) expression on murine dendritic cells. *Journal of Immunology* 152:5208.
33. Lenschow, D. J., T. L. Walunas, and J. A. Bluestone. 1996. CD28/B7 system of T cell costimulation. *Annu Rev Immunol* 14:233.
34. Larsen, C. P., and T. C. Pearson. 1997. The CD40 pathway in allograft rejection, acceptance, and tolerance. *Curr Opin Immunol* 9:641.
35. Vremec, D., J. Pooley, H. Hochrein, L. Wu, and K. Shortman. 2000. CD4 and CD* expression by dendritic cell subtypes in mouse thymus and spleen. *J. Immunology* 164:2978.
36. Gorczynski R M, Yu K, Clark D. 2000. Receptor engagement on cells expressing a ligand for the tolerance-inducing molecule OX2 induces an immunoregulatory population that inhibits alloreactivity in vitro and in vivo. *J Immunol* 2000; 165: 4854-4860.
37. Brady, M. S., Lee, F., Eckels, D. D., Ree, S. Y., Latouche, J. B. and Lee, J. S. (2000) J Immunother 23, 353-361.
38. Jung, D., Hilmes, C., Knuth, A., Jaeger, E., Huber, C. and Seliger, B. (1999) Scand J Immunol 50, 242-249.
39. Freund, Y. R., Mirsalis, J. C., Fairchild, D. G., Brune, J., Hokama, L. A., SchindlerHorvat, J., Tomaszewski, J. E., Hodge, J. W., Schlom, J., Kantor, J. A., Tyson, C. A. and Donohue, S. J. (2000) Int J Cancer 85, 508-517.
40. MartinFontecha, A., Moro, M., Crosti, M. C., Veglia, F., Casorati, G. and Dellabona, P. (2000) J Immunol 164, 698-704.
41. Blazar, B. R., Taylor, P. A., Boyer, M. W., PanoskaltsisMortari, A., Allison, J. P. and Vallera, D. A. (1997) J Immunol 159, 3460-3473.
42. Imamura, M., Hashino, S. and Tanaka, J. (1996) Leuk Lymphoma 23, 477-492.
43. Blazar, B. R., Taylor, P. A., PanoskaltsisMortari, A., Sharpe, A. H. and Vallera, D. A. (1999) 1 Immunol 162, 6368-6377.
44. Champlin, R., Khouri, I., Kornblau, S., Marini, F., Anderlini, P., Ueno, N. T., Molldrem, J. and Giralt, S. (1999) Hematol Oncol Clin N Amer 13, 1041+.
44. Gorczynski, R. M., Adoptive transfer of unresponsiveness to allogeneic skin grafts with hepatic gd+ T cells. Immunology 1994. 81: 27-35.
45. Gorczynski, R. M., Regulation of IFNγ and IL-10 synthesis in vivo, as well as continuous antigen exposure, is associated with tolerance to murine skin allografts. Cell. Immunol. 1995. 160: 224-231.
46. Gorczynski, R. M., Chen, Z., Fu, X. M. and Zeng, H., Increased expression of the novel molecule OX-2 is involved in prolongation of murine renal allograft survival. Transplantation 1998. 65: 1106-1114.
47. Barclay, A. N., Different reticular elements in rat lymphoid tissue identified by localization of Ia, Thy-1 and MRC OX-2 antigens. Immunology 1981.44: 727-736.
48. Gorczynski, L., Chen, Z., Hu, J., Kai, G., Ramakrishna, V. and Gorczynski, R. M., Evidence that an OX-2 positive cell can inhibit the stimulation of type-1 cytokine production by bone-marrow-derived B7-1 (and B7-2) positive dendritic cells. J. Immunol. 1999. 162: 774-781.
49. Wright, G. J., Puklavec, M. J., Hoek, R. M., Sedgewick, J. D., Brown, M. H. and Barclay, A. N., Lymphoid/neuronal cell surface OX2 glycoprotein recognizes a novel receptor on macrophages implicated in the control of their function. Immunity 2000. 13: 233-242.
50. Gorczynski, R. M., Cohen, Z., Fu, X. M. and Lei, J., Anti-rat OX-2 blocks increased small intestinal transplant survival after portal vein immunization. Transpl. Proc. 1999. 31: 577-578.
51. Gorczynski, R. M., Cattral, M. S., Chen, Z. G., Hu, J. A., Lei, J., Min, W. P., Yu, G. and Ni, J., An immunoadhesin incorporating the molecule OX-2 is a potent immunosuppressant that prolongs allo- and xenograft survival. J Immunol 1999.163: 1654-1660.

52. Forster, E., Krenger, W., Joergensen, J., Hof, R., Geha, R. S. and Hollander, G. A., Contribution of CD40-CD154-mediated costimulation to an alloresponse in vivo. Transplantation 1999. 67: 1284-1287.
53. Lespagnard, L., Mettens, P., DeSmedt, T., Bazin, H., Urbain, J., Leo, O. and Moser, M., The immune response induced in vivo by dendritic cells is dependent on B7-1 or B7-2, but the inhibition of both signals does not lead to tolerance. Int Immunol 1998. 10: 295-304.
54. Walunas, T. L. and Bluestone, J. A., CTLA-4 regulates tolerance induction and T cell differentiation in vivo. J Immunol 1998. 160: 3855-3860.
55. Walunas, T. L., Sperling, A. I., Khattri, R., Thompson, C. B. and Bluestone, J. A., CD28 expression is not essential for positive and negative selection of thymocytes or peripheral T cell tolerance J. Immunol. 1996. 156: 1006-1013.
56. Hancock, W. W., Sayegh, M. H., Zheng, X. G., Peach, R., Linsley, P. S. and Turka, L. A., Costimulatory function and expression of CD40 ligand, CD80, and CD86 in vascularized murine cardiac allograft rejection. Proc Natl Acad Sci USA 1996.93: 13967-13972.
57. Freeman, G. J., Boussiotis, V. A., Anumanthan, A., Bernstein, G. M., Ke, X. Y., Rennert, P. D., Gray, G. S., Gribben, J. G. and Nadler, L. M., B7-1 and B7-2 do not deliver identical costimulatory signals, since B7-2 but not B7-1 preferentially costimulates the initial production of IL-4. Immunity 1995. 2: 523-532.
58. Kuchroo, V. K., Das, M. P., Brown, J. A., Ranger, A. M., Zamvil, S. S., Sobel, A., Weiner, H. L., Nabavi, N. and Glimcher, L. H., B7-1 and B7-2 costimulatory molecules activate differentially the Th1/Th2 developmental pathways: application to autoimmune disease therapy. Cell 1995. 80: 707-718.
59. Emtage, P. C. R., Wan, Y. H., Bramson, J. L., Graham, F. L. and Gauldie, J., A double recombinant adenovirus expressing the costimulatory molecule B7-1 (murine) and human IL-2 induces complete tumor regression in a murine breast adenocarcinoma model. J. Immunol 1998. 160: 2531-2538.
60. Imro, M. A., Dellabona, P., Manici, S., Heltai, S., Consogno, G., Bellone, M., Rugarli, C. and Protti, M. P., Human melanoma cells transfected with the B7-2 co-stimulatory molecule induce tumor-specific CD8(+) cytotoxic T lymphocytes in vitro. Hum Gene Ther 1998. 9: 1335-1344.
61. Osman, G. E., Cheunsuk, S., Allen, S. E., Chi, E. M., Liggitt, H. D., Hood, L. E. and Ladiges, W. C., Expression of a type II collagen-specific TCR transgene accelerates the onset of arthritis in mice. Int Immunol 1998. 10: 1613-1622.
62. Barclay, A. N. and Ward, E., Purification and chemical characterization of membrane glycoproteins from rat thymocytes and brain, recognized by monoclonal antibody MRC OX-2. Eur. J. Biochem. 1982. 129: 447-452.
63. Preston, S., Wright, G. J., Starr, K., Barclay, A. N. and Brown, M. H., The leukocyte/neuron cell surface antigen OX2 binds to a ligand on macrophages. Eur J Immunol 1997. 27: 1911-1918.
64. Gorczynski, R. M., Yu, K. and Clark, D., Receptor engagement on cells expressing a ligand for the tolerance-inducing molecule OX2 induces an immunoregulatory population that inhibits alloreactivity in vitro and in vivo. J Immunol 2000. 165: 4854-4860.
65. Gorczynski, R. M., Chen, Z., Kai, Y. and Lei, J., Evidence for persistent expression of OX2 as a necessary component of prolonged renal allograft survival following portal vein immunization. Clin Immunol 2000. 97: 69-78.
66. Rincon, M., Anguita, J., Nakamura, T., Fikrig, E. and Flavell, R. A., Interleukin (IL)-6 directs the differentiation of IL-4-producing CD4+ T cells. J. Exp. Med. 1997.185: 461-469.
67. Gorczynski, R. M., Cinader, B., Ramakrishna, V., Terzioglu, E., Waelli, T. and Westphal, O., Anti IL-6 reverses age-associated cytokine changes. Immunology 1997. 92: 1-6.
68. Gorczynski, R. M., Immunosuppression induced by hepatic portal venous immunization spares reactivity in IL-4 producing T lymphocytes. Immunol. Lett. 1992. 33: 67-77.
69. Gorczynski, R. M., Hozumi, N., Wolfe, S. W. and Chen, Z., Interleukin-12, in combination with anti-interleukin-10, reverses graft prolongation after portal venous immunization. Transplantation 1995. 60: 1337-1341.
70. Schwartz, R. H., Models of T cell anergy: Is there a common molecular mechanism? J Exp Med 1996. 184: 1-8.
71. Ragheb, R., Abrahams, S., Beecroft, R., Hu, J., Ni, J., Ramakrishna, V., Yu, G. and Gorczynski, R. M., Preparation and functional properties of monoclonal antibodies to human, mouse and rat OX-2. Immunol. Lett. 1999. 68: 311-315.
72. Hoek, R. M., Ruuls, S. R., Murphy, C. A., Wright, G. J., Goddard, R., Zurawski, S. M., Blom, B., Homola, M. E., Streit, W. J., Brown, M. H., Barclay, A. N. and Sedgwick, J. D., Down-regulation of the macrophage lineage through interaction with OX2 (CD200). Science 2000. 290: 1768-1771.
73. Gilchrest, B. A. and Bohr, V. A., Aging processes, DNA damage, and repair. FASEB J 1997. 11: 322-330.
74. Fabrega, E., Crespo, J., Casafont, F., Delapena, J., Delasheras, G., Amado, J. A. and Ponsromero, F., Endothelin-1 and vascular complications in liver transplantation. Transplantation 1995. 59: 1748-1751.
75. Gotoh M, Maki T, Kiyoizumi T, Satomi S, Monaco A P. An improved method for isolation of mouse pancreatic islets. *Transplantation* 1985; 40: 437.
76. Thomas F, Pittman K, Berzina P, Contreras J. Role of NK cells in primary nonfunction (PNF) and acute rejection (AR) of pig islet xenografts. *Cell Transplant* 1996; 15: 34.
77. Auchindoss H, Sachs D H. Xenogeneic transplantation. Annu Rev Immunol 1998; 16:433.
78. Morris P J. Xenotransplantation. *Brit Med Bull* 1999; 55: 446.
79. Shimizu A, Meehan S M, Kozlowski T, et al. Acute humoral xenograft rejection: Destruction of the microvascular capillary endothelium in pig-to-nonhuman primate renal grafts. *Lab Invest* 2000; 80: 815.
80. Sankary H N, Yin D P, Chong A S F, et al. FK506 treatment in combination with leflunomide in hamster-to-rat heart and liver xenograft transplantation. *Transplantation* 1998; 66: 832.
81. McKenzie I F C, Koulmanda M, Mandel T E, Sandrin M S. Pig islet xenografts are susceptible to "anti-pig" but not Gal alpha(1,3)Gal antibody plus complement in gal o/o mice. *J Immunol* 1998; 161: 5116.
82. Gysemans C A, Waer B, Valckx D, et al. Early graft failure of xenogeneic islets in NOD mice is accompanied by high levels of interleukin-1 and low levels of transforming growth factor-beta mRNA in the grafts. *Diabetes* 2000; 49: 1992.

83. Wu G S, Korsgren O, Zhang J G, Song Z S, vanRooijen N, Tibell A. Pig islet xenograft rejection is markedly delayed in macrophage-depleted mice: a study in streptozotocin diabetic animals. *Xenotransplantation* 2000; 7: 214.
84. Benda B, Lycke N, Holstad M, Korsgren O. Delayed type hypersensitivity-associated cytokines in islet xenotransplantation: limited efficacy of interleukin-2-and tumor necrosis factor-alpha-blockade in interferon-gamma receptor-deficient mice. *Xenotransplantation* 2000; 7: 206.
85. Friedman T, Smith R N, Colvin R B, Iacomini J. A critical role for human CD4(+) T-cells in rejection of porcine islet cell xenografts. *Diabetes* 1999; 48: 2340.
86. Gordon E J, Markees T G, Phillips N E, et al. Prolonged survival of rat islet and skin xenografts in mice treated with donor splenocytes and anti-CD154 monoclonal antibody. *Diabetes* 1998; 47: 1199.
87. Shapiro A M J, Lakey J R T, Ryan E A, et al. Islet Transplantation in Seven Patients with Type 1 Diabetes Mellitus Using a Glucocorticoid-free Immunosuppressive Regimen. *New Engl J Med* 2000; 343: 230.
88. Suzuki K, Bonner-Weir S, Trivedi N. Function and survival of macroencapsulated syngeneic islets transplanted into streptozotocin-diabetic mice. *Transplantation* 1998; 66: 21.
89. Gorczynski R M, Chen Z, Yu K, Hua J. CD200 immunoadhesin suppresses collagen-induced arthritis in mice. *Clin Immunol* 2001; in press:.
90. Pincus, T., and Callahan, L. F. Taking mortality in rheumatoid arthritis seriously-predictive markers, socioeconomic status and comorbidity. *J. Rheumatol.* 13:841-845, 1986
91. Scott, D. L., Symmons, D. P., Coulton, B. L., and Popert, A. J. Long-term outcome of treating rheumatoid arthritis: results after 20 years. *Lancet* 1:1108-1111, 1987
92. Choy, E. H., and Panayi, G. S. Cytokine pathways and joint inflammation in rheumatoid arthritis. *New Engl. J. Med.* 344:907-916,2001
93. Moreland, L. W., Schiff, M. H., and Baumgartner, S. W. Etanercept therapy in rheumatoid arthritis: a randomized control trial. *Ann. Intern. Med.* 130:478-486, 1999
94. Maini, R., St. Clair, E. W., and Breedveld, F. INfliximab (chimeric tumor necrosis factor a monoclonal antibody) versus placebo in rheumatoid arthritis patients receiving concomitant methotrexate: a randomized phase III trial. *Lancet* 354:1932-1939, 1999
95. Keane, J., Gershon, S., Wise, R. P., Mirabile-Levens, E., Kasznica, J., Schweiterman, W. D., Siegel, J. N., and Braun, M. M. Tuberculosis associated with infliximab, a tumor necrosis factor α-neutralizing agent. *New Engl. J. Med.* 345:1098-1104, 2001
96. Ortmann, R. A., and Shevach, E. M. Susceptibility to collagen-induced arthritis:cytokine-mediated regulation. *Clin. Immunol.* 98:109-118,2001
97. Courtenay, J. S., Dallman, M. J., Dayan, A. D., Martin, A., and Mosedale, B. Immunization against heterologous type II collagen induces arthritis in mice. *Nature* 283: 666-668, 1980.
98. Boissier, M. C., Chiocchia, G., Bessis, N., Hajnal, J., Garotta, G., Nocoletti, F., and Fournier, C. Biphasic effect of interferon-gamma in murine collagen-induced arthritis. *Eur. J. Immunol.* 25:1184-1190, 1995/
99. McIntyre, K. W., Shuster, DJ., Gillooly, K. M., Warrier, R. R., Connaughton, S. E., Hall, L. B., Arp, L. H., Gately, M. K., and Magram, J. Reduced incidence of collagen-induced arthritis in interleukin-12-deficient mice. *Eur. J. Immunol.* 26:2933-2938, 1996.
100. Matthys, P., Vermeire, K., Heremans, H., and Billiau, A. The protective effect of IFN-gamma in experimental autoimmune diseases: a central role of mycobacterial adjuvant-induced myelopoiesis. *J. Leuk. Biol.* 68:447-454,2000.
101. Nakajima, H., Takamori, H., Hiyama, Y., and Tsukada, W. The effect of treatment with interferon-gamma on type II collagen-induced arthritis. *Clin. Exp. Immunol.* 81:441-445, 1990.
102. Mattys, P., Vermeire, K., and Billiau, A. Mac-1+ myelopoiesis induced by CFA: a due to the paradoxical effects of IFNγ in autoimmune disease models. *TRENDS in Immunol.* 22:367-371, 2001.
103. Gorczynski, R. M. Transplant tolerance modifying antibody, to CD200 receptor, but not CD200, alters cytokine production profile from stimulated macrophages. Eur J Immunol 31:2331-2337, 2001.
104. Banchereau, J., Briere, F., Caux, C., Davoust, J., Lebecque, S., Liu, Y. T., Pulendran, B., and Palucka, K. Immunobiology of dendritic cells. Annu Rev Immunol 18:767+, 2000.
105. Almeida, J., Bueno, C., Alguero, M. C., Sanchez, M. L., deSantiago, M., Escribano, L., DiazAgustin, B., Vaquero, J. M., Laso, F. J., SanMiguel, J. F., and Orfao, A. Comparative analysis of the morphological, cytochemical, immunophenotypical, and functional characteristics of normal human peripheral blood lineage (−)/CD16(+)/HLA-DR+/CD14(−/lo) cells, CD14(+) monocytes, and CD16(−) dendritic cells. Clin Immunol 100:325-338, 2001.
106. Gorczynski, R. M., Cohen, Z., Fu, X. M., Hua, Z., Sun, Y. L., and Chen, Z. Q. Interleukin-13, in combination with anti interleukin-12, increases graft prolongation after portal venous immunization with cultured allogeneic bone marrow-derived dendritic cells. Transplantation 62:1592-1600, 1996.
107. Gorczynski, R. M., Gulay, Z., and Wojcik, D. Differential sensitivity to anti-LFA-1 inhibition of Th1 vs Th2 anti-minor histocompatibility antigen immune T cells after restimulation with antigen on hepatic or splenic APCs. Transplantation Proceedings 25:807-808, 1993.
108. Metcalf, D. Murine hematopoietic stem cells committed to macrophage dendritic-cell formation:stimulation by Flk2 ligand with enhancement by regulators using the gp130 receptor chain. Proc. Natl. Acad. Sci. U.S.A. 94:11552-11556, 1997.
109. Ardavin, C. Thymic dendritic cells and T cells develop simultaneously in the thymus from a common precursor population. Nature 362:761-763, 1993.
110. Spits, H. Id2 and Id3 inhibit development of CD34+ stem cells into pre-dendritic cell (pre-DC)$_2$ but not into pre-DC1: evidence for a lymphoid origin of pre-DC2. J. Exp. Med. 192:1775-1783,2000.
111. Manz, M. G. Dendritic cell potentials of early lymphoid and myeloid progenitors. Blood 97:3333-3341, 2001.
112. Ardavin, C., Martinez del Hoyo, G., Martin, P., Anjuere, F., Arias, C. P., Marin, A. R., Ruiz, S., Parrillas, V., and Hernandez, H. Origin and differentiation of dendritic cells. Trends in Immunol. 22:691-700,2001.
113. Mayordomo, J. I. Bone marrow-derived dendritic cells pulsed with synthetic peptides elicit protective and therapeutic antitumor immunity. Nat. Med. 1:1297-1302, 1995.
114. Caux, C. GM-CSF and TNFα cooperate in the generation of dendritic Langerhans cells. Nature 360:258-261, 1992.

115. Maraskovsky, E., Brasel, K., Teepe, M., Roux, E. R., Lyman, S. D., Shortman, K., and McKenna, H. J. Dramatic increase in the numbers of functionally mature dendritic cells in Flt 3 Ligand-treated mice: multiple dendritic cell subpopulations identified. Journal of Experimental Medicine 184:1953-1962, 1996.

116. Saunders, D. Dendritic cell development in culture from thymic precursor cells in the absence of granulocyte-macrophage colony-stimulating factor. J. Exp. Med. 1384:2185-2196, 1996.

117. Borkowski, TA role for endogenous transforming growth factor b1 in Langerhans-cell biology: the skin of transforming growth factor b1 null mice is devoid of epidermal Langerhans cells. J. Exp. Med. 184:2417-2422, 1996.

118. denHaan, J. M. M., Lehar, S. M., and Bevan, M. J. CD8(+) but not CD8(−) dendritic cells cross-prime cytotoxic T cells in vivo. J Exp Med 192:1685-1695, 2000.

119. Kuwana, M., Kaburaki, J., Wright, T. M., Kawakami, Y., and Ikeda, Y. Induction of antigen-specific human CD4(+) T cell anergy by peripheral blood DC2 precursors. Eur J Immunol 31:2547-2557,2001.

120. MaldonadoLopez, R., DeSmedt, T., Michel, P., Godfroid, J., Pajak, B., Heirman, C., Thielemans, K., Leo, O., Urbain, J., and Moser, M. CD8 alpha(+) and CD8 alpha (−) subclasses of dendritic cells direct the development of distinct T helper cells in vivo. J Exp Med 189:587-592, 1999.

121. MaldonadoLopez, R., Maliszewski, C., Urbain, J., and Moser, M. Cytokines regulate the capacity of CD8 alpha (+) and CD8 alpha(−) dendritic cells to prime Th1/Th2 cells in vivo. J Immunol 167:4345-4350, 2001.

122. Pulendran, B., Smith, J. L., Caspary, G., Brasel, K., Pettit, D., Maraskovsky, E., and Maliszewski, C. R. Distinct dendritic cell subsets differentially regulate the class of immune responses in vivo. Proc. Natl. Acad. Sci. U.S.A. 96:1036-1041,1999.

123. O'Connell, P. J., Li, W., Wang, Z., Specht, S. M., Logar, A. J., and Thomson, A. W. Immature and mature CD8a+ dendritic cells prolong the survival of vascularized heart allografts. J. Immunol. 168:143-154,2002.

124. Denfeld, R. W., Hara, H., Tesmann, J. P., Martin, S., and Simon, J. C. UVB-irradiated dendritic cells are impaired in their APC function and tolerize primed Th1 cells but not naive CD4+ T cells. J Leukocyte Biol 69:548-554, 2001.

125. Corinti, S., Albanesi, C., la Sala, A., Pastore, S., and Girolomoni, G. Regulatory activity of autocrine IL-10 on dendritic cell functions. J. Immunol. 166:4312-4318, 2001.

126. Hackstein, H., Morelli, A. E., and Thomson, A. W. Designer dendritic cells for tolerance induction: guided not misguided missiles. Trends Immunol 22:437-442, 2001.

127. Sakaguchi, S., Sakaguchi, N., Shimizu, J., Yamazaki, S., Sakihama, T., Itoh, M., Kuniyasu, Y., Nomura, T., Toda, M., and Takahashi, T. Immunologic tolerance maintained by CD25(+) CD4(+) regulatory T cells: their common role in controlling autoimmunity, tumor immunity, and transplantation tolerance. Immunol Rev 182:18-32, 2001.

128. Levings, M. K., and Roncarolo, M. G. T-regulatory 1 cells: A novel subset of CD4(+)T cells with immunoregulatory properties. J Allerg Clin Immunol 106:S109-S112, 2000.

129. Lu, L., Bonham, C. A., Liang, X., Chen, Z., Li, W., Wang, L., Watkins, S. C., Nalesnik, M. A., Schlissel, M. S., and Demetris, A. J. Liver-derived DEC205+B220+ CD19− dendritic cells regulate T cell responses. J. Immunol. 166:7042-7048,2001.

130. Lu, L., Li, W., Zhong, C. P., Qian, S. G., Fung, J. J., Thomson, A. W., and Starzl, T. E. Increased apoptosis of immunoreactive host cells and augmented donor leukocyte chimerism, not sustained inhibition of B7 molecule expression are associated with prolonged cardiac allograft survival in mice preconditioned with immature donor dendritic cells plus anti-CD40L mAb. Transplantation 68:747-757,1999.

131. Lu, L., McCaslin, D., Starzl, T. E., and Thomson, A. W. Bone marrow-derived dendritic cell progenitors (NLDC 145+, MHC class 11+, B7-1dim, B7−2−) induce alloantigen-specific hyporesponsiveness in murine T lymphocytes. Transplantation 60:1539-1567, 1995.

132. Lutz, M. B., Kukutsch, N. A., Menges, M., Rossner, S., and Schuler, G. Culture of bone marrow cells in GM-CSF plus high doses of lipopolysaccharide generates exclusively immature dendritic cells which induce alloantigen-specific CD4 T cell anergy in vitro. Eur J Immunol 30:1048-1052,2000.

133. Zhang, Y. Transforming growth factor β1 polarizes murine hematopoietic progenitor cells to generate Langerhans-cell-like dendritic cells through a monocyte/macrophage differentiation pathway. Blood 93:1208-1220, 1999.

134. Gorczynski, R. M., Hu, J., Chen, Z., Kai, Y., and Lei, J. A CD200Fc immunoadhesin prolongs rat islet xenograft survival in mice. Transplantation in press, 2002.

135. DeSmedt, T., Butz, E., Smith, J., MaldonadoLopez, R., Pajak, B., Moser, M., and Maliszewski, C. CD8 alpha(−) and CD8 alpha(+) subclasses of dendritic cells undergo phenotypic and functional maturation in vitro and in vivo. J Leukocyte Biol 69:951-958, 2001.

136. Jonuleit, H., Schmitt, E., Steinbrink, K., and Enk, A. H. Dendritic cells as a tool to induce anergic and regulatory T cells. Trends Immunol 22:394-400, 2001.

137. Rissoan, M., Soumelis, C. V., Kadowaki, N., Grouard, G., Briere, P., de Waal Malefyt, R., and Liu, Y. J. Reciprocal control of T helper cell and dendritic cell differentiation. Science 283:1183-1186, 1999.

138. Dhodapkar, M. V., Steinman, R. M., Krasovsky, J., Munz, C., and Bhardwaj, N. Antigen-specific inhibition of effector T cell function in humans after injection of immature dendritic cells. J. Exp. Med. 193:233-240, 2001.

139. Jonuleit, H., Schmitt, E., Schuler, G., Knop, J., and Enk, A. H. Induction of interleukin 10-producing, non-proliferating CD4(+) T cells with regulatory properties by repetitive stimulation with allogeneic immature human dendritic cells. J Exp Med 192:1213-1222,2000.

140. Wang, Y., Newton, D. C., Robb, G. B., Kau, C-L., Miller, T. L., Cheung, A. H., Hall, A. V., Wilcox, J. N., Marsden, P. A. RNA diversity has profound effects on the translation of neuronal nitric oxide synthase. *Proc. Natl. Acad. Sci. USA* 96:12150-12155, 1999.

141. Marsden, P. A., Heng, H. H. Q., Scherer, S. W., Stewart, R. W., Hall, A. V., Shi, X., Tsui, L-C., Schappert, K. T. Structural organization and chromosomal localization of the human endothelial constitutive nitric oxide synthase gene. *J. Biol. Chem.* 268: 17478-17488, 1993.

142. Osoegawa, K. et al. Bacterial artificial chromosome libraries for mouse sequencing and functional analysis. *Genome Research* 10: 116-128,2000.

143. Bitzan, M. M., Wang, Y., Lin, L., Marsden, P. A. Verotoxin and ricin have novel effects on preproendothelin-1 expression but fail to modify nitric oxide synthase (NOS) expression and NO production in vascular endothelium. *J. Clin. Invest.*, 101:372-382, 1998.

We claim:

1. An isolated CD200R2a protein comprising an amino acid sequence shown in FIG. 4 (SEQ ID NO:2).

2. An isolated CD200R2b protein comprising an amino acid sequence shown in FIG. 5 (SEQ ID NO:4).

3. A fragment of an isolated CD200R2a protein comprising amino acids 1 to 216 in SEQ ID NO:2, wherein the fragment can bind CD200.

4. A fragment of an isolated CD200R2b protein comprising amino acids 1 to 259 in SEQ ID NO:4, wherein the fragment can bind CD200.

5. A fusion protein comprising the CD200R2a protein according to claim 1.

6. A fusion protein comprising the CD200R2b protein according to claim 2.

7. A fusion protein comprising the CD200R2a protein fragment according to claim 3.

8. A fusion protein comprising the CD200R2b protein fragment according to claim 4.

9. The fusion protein according to claim 7 wherein the CD200R2a fragment is linked to an immunoglobulin (Ig) Fc region.

10. A fusion protein according to claim 8 wherein the CD200R2b fragment is linked to an immunoglobulin (Ig) Fc region.

* * * * *